US012741023B2

(12) United States Patent
Wang et al.

(10) Patent No.: US 12,741,023 B2
(45) Date of Patent: Sep. 22, 2026

(54) PREPARATION COMPRISING ANTI-PCSK9 ANTIBODY AND USE THEREOF

(71) Applicant: INNOVENT BIOLOGICS (SUZHOU) CO., LTD., Suzhou (CN)

(72) Inventors: Yinjue Wang, Suzhou (CN); Xiaolin Liu, Suzhou (CN); Ruixia Xie, Suzhou (CN)

(73) Assignee: INNOVENT BIOLOGICS (SUZHOU) CO., LTD., Suzhou (CN)

( * ) Notice: Subject to any disclaimer, the term of this patent is extended or adjusted under 35 U.S.C. 154(b) by 1421 days.

(21) Appl. No.: 17/050,179

(22) PCT Filed: May 10, 2019

(86) PCT No.: PCT/CN2019/086388
§ 371 (c)(1),
(2) Date: Oct. 23, 2020

(87) PCT Pub. No.: WO2019/214707
PCT Pub. Date: Nov. 14, 2019

(65) Prior Publication Data

US 2022/0062416 A1 Mar. 3, 2022

(30) Foreign Application Priority Data

May 11, 2018 (CN) ......................... 201810450088.5

(51) Int. Cl.
*A61K 39/395* (2006.01)
*A61K 39/00* (2006.01)
(Continued)

(52) U.S. Cl.
CPC ...... *A61K 39/39591* (2013.01); *A61K 47/183* (2013.01); *A61K 47/26* (2013.01);
(Continued)

(58) Field of Classification Search
CPC ............ A61K 39/39591; A61K 47/183; A61K 47/26; A61K 2039/505; A61K 2039/54;
(Continued)

(56) References Cited

U.S. PATENT DOCUMENTS 5,648,237 A 7/1997 Carter
5,789,199 A 8/1998 Joly et al.
(Continued)

FOREIGN PATENT DOCUMENTS

AU 2009212282 B2 8/2014
CA 3047049 A1 6/2018
(Continued)

OTHER PUBLICATIONS

Chiu M. et al, Antibody Structure and Function: The Basis for Engineering Therapeutics. Antibodies 8(4), 55, 2019 (Year: 2019).*
(Continued)

*Primary Examiner* — Joanne Hama
*Assistant Examiner* — Matthew Curran Metcalf
(74) *Attorney, Agent, or Firm* — LEASON ELLIS LLP

(57) ABSTRACT

The present invention relates to a preparation comprising an anti-PCSK9 antibody and use thereof, and in particular to a pharmaceutical preparation comprising an antibody and/or an antibody fragment specifically binding to proprotein convertase subtilisin/kexin type 9 (PCSK9), a buffer, a viscosity inhibitor, and a surfactant. The present invention also relates to an anti-PCSK9 antibody. Furthermore, the present invention relates to therapeutic and diagnostic use of the preparation or the antibody.

21 Claims, 12 Drawing Sheets

Specification includes a Sequence Listing.

(51) Int. Cl.
*A61K 47/18* (2017.01)
*A61K 47/26* (2006.01)
*A61P 3/06* (2006.01)
*C07K 16/40* (2006.01)

(52) U.S. Cl.
CPC ................ *A61P 3/06* (2018.01); *C07K 16/40* (2013.01); *A61K 2039/505* (2013.01); *C07K 2317/92* (2013.01)

(58) Field of Classification Search
CPC . A61K 9/0019; A61K 9/08; A61P 3/06; A61P 3/10; A61P 5/00; A61P 9/00; A61P 9/10; A61P 25/28; C07K 16/40; C07K 2317/92; C07K 2317/33; C07K 2317/565; C07K 2317/76
See application file for complete search history.

(56) References Cited

U.S. PATENT DOCUMENTS

| | | | | |
|---|---|---|---|---|
| 5,840,523 | A | 11/1998 | Simmons et al. | |
| 6,171,586 | B1 | 1/2001 | Lam et al. | |
| 6,267,958 | B1 | 7/2001 | Andya et al. | |
| 8,030,457 | B2 | 10/2011 | Jackson et al. | |
| 8,062,640 | B2 | 11/2011 | Sleeman et al. | |
| 8,080,243 | B2 | 12/2011 | Liang et al. | |
| 11,485,795 | B2 * | 11/2022 | Tsun | G01N 33/573 |
| 2009/0142352 | A1 | 6/2009 | Jackson et al. | |
| 2009/0246192 | A1 | 10/2009 | Condra et al. | |
| 2010/0166768 | A1 | 7/2010 | Sleeman et al. | |
| 2013/0189277 | A1 | 7/2013 | Walsh et al. | |
| 2015/0004174 | A1 | 1/2015 | Wasserman et al. | |
| 2017/0253666 | A1 * | 9/2017 | Gusarova | A61P 3/06 |
| 2020/0087416 | A1 | 3/2020 | Tsun et al. | |

FOREIGN PATENT DOCUMENTS

| | | | | |
|---|---|---|---|---|
| CN | 103717237 | A | 4/2014 | |
| CN | 105001336 | A | 10/2015 | |
| CN | 105348390 | A | 2/2016 | |
| CN | 105801701 | A | 7/2016 | |
| CN | 106084058 | A | 11/2016 | |
| CN | 107261139 | A | 10/2017 | |
| CN | 108239150 | A * | 7/2018 | A61K 39/395 |
| CN | 109563161 | A | 4/2019 | |
| EA | 028227 | B1 | 10/2017 | |
| EA | 201792336 | A2 | 6/2018 | |
| EP | 0404097 | A2 | 12/1990 | |
| JP | 2013-509194 | A | 3/2013 | |
| JP | 2014516953 | A | 7/2014 | |
| JP | 2014525915 | A | 10/2014 | |
| JP | 2016-528193 | A | 9/2016 | |
| JP | 2018-188430 | A | 11/2018 | |
| JP | 2019-504086 | A | 2/2019 | |
| JP | 2020506670 | A | 3/2020 | |
| TW | 201946659 | A | 12/2019 | |
| WO | 1993/01161 | A1 | 1/1993 | |
| WO | 2005/103081 | A2 | 11/2005 | |
| WO | 2006/044908 | A2 | 4/2006 | |
| WO | 2008/105797 | A2 | 9/2008 | |
| WO | 2009/026558 | A1 | 2/2009 | |
| WO | 2009/036379 | A2 | 3/2009 | |
| WO | 2009/100297 | A1 | 8/2009 | |
| WO | 2010/029513 | A2 | 3/2010 | |
| WO | 2010/077854 | A1 | 7/2010 | |
| WO | 2010/105256 | A1 | 9/2010 | |
| WO | 2012/009568 | A2 | 1/2012 | |
| WO | 2012/065072 | A2 | 5/2012 | |
| WO | WO-2012154999 | A1 * | 11/2012 | A61P 3/06 |
| WO | WO-2013016648 | A2 * | 1/2013 | A61K 39/3955 |
| WO | 2013/166448 | A1 | 11/2013 | |
| WO | 2013/188855 | A1 | 12/2013 | |
| WO | 2015/200438 | A1 | 12/2015 | |
| WO | 20170136433 | A1 | 8/2017 | |
| WO | 2018/067987 | A1 | 4/2018 | |
| WO | WO-2018113781 | A1 * | 6/2018 | A61K 39/395 |
| WO | 2018/156741 | A1 | 8/2018 | |
| WO | 2019173530 | A1 | 9/2019 | |
| WO | WO-2021207152 | A1 * | 10/2021 | |

OTHER PUBLICATIONS

Agarkhed, M., et al. Effect of Surfactants on Mechanical, Thermal, and Photostability of a Monoclonal Antibody. AAPS PharmSciTech 19, 79-92 (2018) (Year: 2018).*

Agarkhed, M., O'Dell, C., Hsieh, MC. et al. Effect of Surfactants on Mechanical, Thermal, and Photostability of a Monoclonal Antibody. AAPS PharmSciTech 19, 79-92 (2018). https://doi.org/10.1208/s12249-017-0845-7 (Year: 2017).*

Tomar et al. "Molecular basis of high viscosity in concentrated antibody solutions: Strategies for high concentration drug product development", MABS, 2016, vol. 8, No. 2, 216-228.

Examination Report No. 1 in Australian application No. 2017379048, dated Apr. 23, 2020.

Examination Report in Canadian application No. 3,047,049, dated Sep. 15, 2020.

Extended European Search Report in EP Application No. 17883464.4, dated Nov. 19, 2020.

Center For Drug Evaluation And Research: "Pharmacology Review: Repatha (evolocumab)", Aug. 20, 2015, pp. 1-80.

Manal Alkindi et al:"Monoclonal Antibodies for the Treatment of Hypercholesterolemia: Targeting PCSK9", Canadian Journal of Cardiology., vol. 32, No. 12, May 3, 2016, pp. 1552-1560.

Cormac Sheridan: "Phase 3 data for PCSK9 inhibitor wows", Nature Biotechnology, vol. 31, Dec. 6, 2013, pp. 1057-1058.

Rudikoff S et al : "Single amino acid substitution altering antigen-binding specificity", Proceedings of the National Academy of Sciences, National Academy of Sciences, vol. 79, No. 6, Mar. 1, 1982, pp. 1979-1983.

Stephan Duebel ED—Stefan Dubel: "Handbook of Therapeutic Antibodies Chapter 6", Jan. 1, 2007, Handbook Oftherapeutic Antibodies, Wiley-VCH. Weinheim, pp. 119-144.

S. Kuhnast et al: "Alirocumab inhibits atherosclerosis, improves the plaque morphology, and enhances the effects of a statin", Journal of Lipid Research, vol. 55, No. 10, Oct. 1, 2014, 2103-2112.

Toth Peter P ED, Chilton Robert: "Novel Therapies for Low Density Lipoprotein Cholesterol Reduction", American Journal of Cardiology, Cahners Publishing Co., Newton, MA, US, 2016, vol. 118, No. 6.

Zhao et al. Guidelines for the Prevention and Treatment of Dyslipidemia in Chinese Adults (2016 Revised Edition). Chinese Circulatory Journal, 2016, 31(10): 937-953.

Latimer et al. PCSK9 inhibitors in the prevention of cardiovascular disease. Journal of Thrombosis and Thrombolysis, 2016, 42(3):405-419.

Blom et al. PCSK9 inhibition in the management of hyperlipidemia: focus on evolocumab. Vascular Health and Risk Management, 2016, 12:185-197.

US prescribing information of Evolocumab dated Aug. 2015.

US prescribing information of Alirocumab dated Jul. 2015.

Zhang et al., "Pathogenic gene mutation in patients with familial hypercholesterolemia and premature coronary heart disease", Journal of Chinese Practical Diagnosis and Therapy, 2015, 29(6):549-552.

Zhang et al., "The Clinical Characteristics of Cardiovascular Involvement in Patients With Familial Hypercholesterolemia", Chinese Circulation Journal 2015, 29(5):327-330.

Hu et al., "The status of Chinese prevention and treatment of dyslipidemia", Chinese Journal of Internal Medicine, 2009, 29(1):2-4.

Li et al, "The levels and distribution of the serum lipids in Chinese adults, 2010". China J. of Prev. Med. 2012, 46(7):607-612.

Li et al, "Epidemologic characteristics of dyslipidemia in Chinese adults, 2010", China J. of Prev. Med. 2012, 46(5):414-418.

(56) References Cited

OTHER PUBLICATIONS

Li et al, "Awareness rate, treatment rate and control rate of dyslipidemia in Chinese adults, 2010", China J. of Prev. Med. 2012, 46(8):687-691.
Report on Cardiovascular Diseases in China (2014) National Center for Cardiovascular Diseases, China.
Neil et al. "Reductions in all-cause, cancer, and coronary mortality in statin-treated patients with heterozygous familial hypercholesterolaemia: a prospective registry study". European Heart Journal. 2008, 29(21):2625-2633.
Raal et al. "Expanded-dose simvastatin is effective in homozygous familial hypercholesterolaemia". Atherosclerosis. 1997, 135(2):249-256.
Watts et al. "Integrated guidance on the care of familial hypercholesterolaemia from the International FH Foundation". International Journal of Cardiology. 2014, 171(3):309-325.
Nordestgaard et al. "Familial hypercholesterolaemia is underdiagnosed and undertreated in the general population guidance for clinicians to prevent coronary heart disease". European Heart Journal. 2013, 34(45):3478a-3490a.
Careskey et al. "Atorvastatin increases human serum levels of proprotein convertase subtilisin/kexin type 9". Journal of Lipid Research, 2008, 49(2):394-398.
World Preview 2014, Outlook to 2020. EvaluatePharma 2014.
Partial European Search Report in EP Application No. 17883464.4, dated Jul. 17, 2020.
International Search Report and Written Opinion in PCT/CN2019/086388, mailed on Aug. 15, 2019.
Vajdos et al., Comprehensive Functional Maps of the Antigen-binding Site of an Anti-Erb82 Antibody Obtained with Shotgun Scanning Mutagenesis, J Mol Biol. 2002; 320 (2):415-28.
Brown et al., Tolerance to Single, but Not Multiple, Amino Acid Replacements in Antibody VH CDR2, J Immunol. 1996, 156(9): 3285-91.
Mateu et al., Non-additive effects of multiple amino acid substitutions on antigen-antibody recognition, Eur J Immunol. 1992; 22(6): 1385-9.
Greenspan et al., Defining epitopes: It's not as easy as it seems. Nat Biotechnol. 1999; 17(10):936-7.
U.S. Appl. No. 17/642,978, filed Mar. 15, 2022.
International Search Report and Written Opinion of PCT/CN2020/116245, mailed on Dec. 16, 2020.
Viola, Margarida et al: "Subcutaneous delivery of monoclonal antibodies: How do we get there?", Journal of Controlled Release, Elsevier, Amsteroam, NL, vol. 286, 2018, pp. 301-314.
Dondelinger et al., "Understanding the Significance and Implications of Antibody Numbering and Antigen-Binding Surface/Residue Definition", Front Immunol. 2018, v.9, No. 2278, p. 1-15 [15 pages].
Herold et al. "Determinants of the assembly and function of antibody variable domains", Sci. Rep., 2017, 7:12276, pp. 1-17. [17 pages].
Janda et.al. "Ig Constant Region Effects on Variable Region Structure and Function", Frontiers in Janda et al. "Ig Constant Region Effects on Variable Region Structure and Function", Frontiers in Microbiology. 2016, v.7, n.22, pp. 1-10. [10 pages].
Su et al. "The role of Antibody Vk Framework 3 region towards Antigen binding: Effects on recombinant production and Protein L binding", Scientific Reports, 2017, 7:3766, pp. 1-7. [7 pages].
Waters et al., Lipid Treatment Assessment Project 2: a multinational survey to evaluate the proportion of patients achieving low-density lipoprotein cholesterol goals. Circulation. 120(1):28-34, 2009.
Libby P., The forgotten majority: unfinished business in cardiovascular risk reduction. Journal of the American College of Cardiology. 46(7):1225-1228, 2005.
Duff CJ., et al., Antibody-mediated disruption of the interaction between PCSK-9 and the low-density lipoprotein receptor. The Biochemical Journal. 419(3):577-584, 2009.
Lambert G., et al., Molecular basis of PCSK-9 function. Atherosclerosis. 203(1):1-7, 2009.
George M, et al., Looking into the crystal ball-upcoming drugs for dyslipidemia. Journal of Cardiovascular Pharmacology and Therapeutics. 20(1):11-20, 2016.
Zhang Y., et al., Dysregulation of the low-density lipoprotein receptor pathway is involved in lipid disorder-mediated organ injury. International Journal of Biological Sciences. 12(5):569-579, 2016.
Burke AC., et al.PCSK-9: regulation and target for drug development for dyslipidemia. Annual Review of Pharmacology and Toxicology. 13(3), 2016.
Abifadel M., et al., Mutations in PCSK-9 cause autosomal dominant hypercholesterolemia. Nature Genetics. 34(2):154-156, 2003.
Cohen JC., et al., Sequence variations in PCSK-9, low LDL, and protection against coronary heart disease. New England Journal of Medicine. 54(12):1264-1272, 2006.
Zhao Z., et al., Molecular characterization of loss of function mutations in PCSK-9 and identification of a compound heterozygote. American Journal of Human Genetics. 79(3):514-523, 2006.
Lagace TA., et al., Secreted PCSK-9 decreases the number of LDL receptors in hepatocytes and in livers of parabiotic mice. Journal of Clinical Investigation. 116(11):2995-3005, 2006.
Rashid S., et al., Decreased plasma cholesterol and hypersensitivity to statins in mice lacking PCSK-9. Proceedings of the National Academy of Sciences of the United States of America. 102(15):5374-5379, 2005.
Law et al: Quantifying effect of statins on low density lipoprotein cholesterol, ischaemic heart disease, and stroke: systematic review and meta-analysis, BMJ, 2003, 326:1423-1427.
Hudson et al: Engineered Antibodies: Nat. Med., 9:129-134 (2003).
Hollinger et al: "Diabodies": Small bivalent and bispecific antibody fragments, Proc. Natl. Acad. Sci. (USA) 90: 6444-6448 (1993).
Clackson et al: Making antibody fragments using phage display libraries: Nature 352:624-628 (1991).
Shields et al: Lack of Fucose on Human IgG1 N-Linked Oligosaccharide Improves Binding to Human FcyRIII and Antibody-dependent Cellular Toxicity: J. Biol. Chem. (2002) 277:26733.
Almagro JC et al: Humanization of Antibodies: Frontiers inBioscience, (2008) 13:1619-1633.
Lonberg, Fully Human Antibodies from transgenic mouse and phage display platforms: Curr. Opin. Immunol. 20:450-459 (2008).
McCafferty et al: Phage antibodies: filamentous phage displaying antibody variable domains: Nature, 1990, 348:552-554.
Marks et al: By-passing Immunization Human Antibodies from V-gene Libraries Displayed on Phage: J. Mol. Biol. 222:581-597(1992).
Sidhu et al: Phage-displayed Antibody Libraries of Synthetic Heavy Chain Complementarity Determining Regions, J. Mol. Biol. 338(2): 299-310 (2004).
Lee et al: High-affinity Human Antibodies from Phage-displayed Synthetic Fab Libraries with a Single Framework Scaffold, J. Mol. Biol. 340(5): 1073-1093 (2004).
Fellouse: Synthetic antibodies from a four-amino-acid code: A dominant role for tyrosine in antigen recognition, Proc. Natl. Acad. Sci. USA, 101(34): 12467-12472 (2004).
Lee et al: Bivalent antibody phage display mimics natural immunoglobulin, J. Immunol. Methods, 284(1-2): 119-132 (2004).
Graham et al: Characteristics of a Human Cell Line Transformed by DNA from Human Adenovirus Type 5, J. Gen. Virol. 36: 59 (1977).
Urlaub et al: Isolation of Chinese hamster cell mutants deficient in dihydrofolate reductase activity, Proc. Natl. Acad. Sci. USA, 77: 216 (1980).
Estep, P et al: High throughput solution Based measurement of antibody-antigen affinity and epitope binning. MAbs, 2013, 5(2): 270-8.
Xu et al., Addressing polyspecificity of antibodies selected froman in vitro yeast presentation system: a FACS-based, high-throughput selection and analytical tool, Protein Engineering, Design & Selection, vol. 26 No. 10, pp. 663-670, 2013.
International search report and Written Opinion of corresponding International Application PCT/CN2017/118050, mailed on Mar. 27, 2018, with English translation.
Ballantyne et al, "Results of Bococizumab, A Monoclonal Antibody Against Proprotein Convertase Subtilisin/Kexin Type 9, from a

(56) References Cited

OTHER PUBLICATIONS

Randomized, Placebo-Controlled, Dose-Ranging Study in Statin-Treated Subjects With Hypercholesterolemia." American Journal of Cardiology, vol. 115, No. 9, 2015, pp. 1212-1221.
Kastelein et al., "Safety and efficacy of LY3015014, a new monoclonal antibody to proprotein convertase subtilisin/kexin type 9 (pcsk9) with an inherently longer duration of action, in patients with primary hypercholesterolemia: a randomized, placebo-controlled, dose-ranging, phase 2 study", Journal of the American College of Cardiology, vol. 65, No. 10, 2015.
Ito et al., "PCSK9 Inhibition with Monoclonal Antibodies: Modern Management of Hypercholesterolemia : PSCK9 in Management of Hypercholesterolemia", The Journal of Clinical Pharmacology, vol. 57, No. 1, 2017, pp. 7-32.
McKenney J., "Understanding PCSK9 and anti-PCSK9 therapies", Journal of Clinical Lipidology, vol. 9, No. 2, 2015, pp. 170-186.
Cooper et al., Role of heavy chain constant domains in antibody-antigen interaction. Apparent specificity differences among streptococcal IgG antibodies expressing identical variable domains. J. Immunol. 1993, 150 (6):2231-2242. (12 pages).
Liang et al., Dramatic activation of an antibody by a single amino acid change in 7 framework. Scientifc Reports, 2021, v.11, No. 22365, p. 1-9. (9 pages).
Bates et al., (2019). David vs. Goliath: The Structure, Function, and Clinical Prospects of Antibody Fragments. Antibodies, 8(2), 28, p. 1-31. (31 pages).
Kastelein et al.: "Safety and efficacy of LY3015014, a monoclonal antibody to proprotein convertase subtilisin/kexin type 9 (PCSK9): a randomized, placebo-controlled Phase 2 study", European Heart Journal, vol. 37(17), pp. 1360-1369, 2016. [10 pages].
Pharmaceutics, edited by Cui Fude et al., China Medical Science and Technology Press (ISBN 7-5067-2557-6), published in Aug. 2002, Chapter 19, New Dosage Forms of Drugs, p. 582.

* cited by examiner

| IgG ADI name | VH germline | VH FR1 | VH CDR1 | VH FR2 | VH CDR2 | VH FR3 | VH CDR3 | VH FR4 |
|---|---|---|---|---|---|---|---|---|
| ADI- 023 96 | VH 4-3 9 | QLQLQESGPGLVKPSE T LSLTCTVSG(SEQ ID NO:45) | GSISSSSYYW G(SEQ ID NO:1) | WIRQPPGKGLE WIG(SEQ ID NO:46) | SIYYSGSTYYNP SLKS(SEQ ID NO:2) | RVTISVDTSKNQFSLKLS SVTAADTAVYYC(SEQ ID NO:47) | AREGSGVVPAAGP NWFDP(SEQ ID NO:3) | WGQGTLVTVS S(SEQ ID NO:48) |
| ADI- 091 11 | VH 4-3 9 | QLQLQESGPGLVKPSE T LSLTCTVSG(SEQ ID NO:45) | GSISSSSYYW G(SEQ ID NO:1) | WIRQPPGKGLE WIG(SEQ ID NO:46) | SIYYSGSTYYNP SLKS(SEQ ID NO:2) | RVTISVDTSKNQFSLKLS SVTAADTAVYYC(SEQ ID NO:47) | ARENSGVVPAAGP NWFDP(SEQ ID NO:18) | WGQGTLVTVS S(SEQ ID NO:48) |
| ADI- 091 12 | VH 4-3 9 | QLQLQESGPGLVKPSE T LSLTCTVSG(SEQ ID NO:45) | GSISSSSYYW G(SEQ ID NO:1) | WIRQPPGKGLE WIG(SEQ ID NO:46) | SIYYSGSTYYNP FLKS(SEQ ID NO:14) | RVTISVDTSKNQFSLKLS SVTAADTAVYYC(SEQ ID NO:47) | ARENSGVVPAAGP NWFGP(SEQ ID NO:19) | WGQGTLVTVS S(SEQ ID NO:48) |
| ADI- 091 13 | VH 4-3 9 | QLQLQESGPGLVKPSE T LSLTCTVSG(SEQ ID NO:45) | GSVSSSSYYW G(SEQ ID NO:7) | WIRQPPGKGLE WIG(SEQ ID NO:46) | SAYYSGSTYYNP SLKS(SEQ ID NO:15) | RVTISVDTSKNQFSLKLS SVTAADTAVYYC(SEQ ID NO:47) | ARENSGVVPAAGP NWFDP(SEQ ID NO:18) | WGQGTLVTVS S(SEQ ID NO:48) |
| ADI- 100 85 | VH 4-3 9 | QLQLQESGPGLVKPSE T LSLTCTVSG(SEQ ID NO:45) | GSIVSSSYYW A(SEQ ID NO:8) | WIRQPPGKGLE WIG(SEQ ID NO:46) | SINYKGSTYYNP SLKS(SEQ ID NO:16) | RVTISVDTSKNQFSLKLS SVTAADTAVYYC(SEQ ID NO:47) | ARENSGVVPAAGP NWFGP(SEQ ID NO:19) | WGQGTLVTVS S(SEQ ID NO:48) |
| ADI- 100 86 | VH 4-3 9 | QLQLQESGPGLVKPSE T LSLTCTVSG(SEQ ID NO:45) | GSIRSSAYYW G(SEQ ID NO:9) | WIRQPPGKGLE WIG(SEQ ID NO:46) | SINYRGSTYYNP SLKS(SEQ ID NO:17) | RVTISVDTSKNQFSLKLS SVTAADTAVYYC(SEQ ID NO:47) | ARENSGVVPAAGP NWFGP(SEQ ID NO:19) | WGQGTLVTVS S(SEQ ID NO:48) |

FIG. 4A

| IgG ADI name | VH germline | VH FR1 | VH CDR1 | VH FR2 | VH CDR2 | VH FR3 | VH CDR3 | VH FR4 |
|---|---|---|---|---|---|---|---|---|
| ADI-10087 | VH 4-39 | QLQLQESGPGLVKPSET LSLTCTVSG(SEQ ID NO:45) | GSISSASYYWS (SEQ ID NO:10) | WIRQPPGKGLEW IG(SEQ ID NO:46) | SINYRGSTYYNPS LKS(SEQ ID NO:17) | RVTISVDTSKNQFSLKLS SVTAADTAVYYC(SEQ ID NO:47) | ARENSGVVPAAGPN WFGP(SEQ ID NO:19) | WGQGTLVTVS S(SEQ ID NO:48) |
| ADI-10088 | VH 4-39 | QLQLQESGPGLVKPSET LSLTCTVSG(SEQ ID NO:45) | GSIGSSSYYWA (SEQ ID NO:11) | WIRQPPGKGLEW IG(SEQ ID NO:46) | SINYRGSTYYNPS LKS(SEQ ID NO:17) | RVTISVDTSKNQFSLKLS SVTAADTAVYYC(SEQ ID NO:47) | ARENSGVVPAAGPN WFDP(SEQ ID NO:18) | WGQGTLVTVS S(SEQ ID NO:48) |
| ADI-10089 | VH 4-39 | QLQLQESGPGLVKPSET LSLTCTVSG(SEQ ID NO:45) | GSIGSSSYYWT (SEQ ID NO:12) | WIRQPPGKGLEW IG(SEQ ID NO:46) | SINYRGSTYYNPS LKS(SEQ ID NO:17) | RVTISVDTSKNQFSLKLS SVTAADTAVYYC(SEQ ID NO:47) | ARENSGVVPAAGPN WFDP(SEQ ID NO:18) | WGQGTLVTVS S(SEQ ID NO:48) |
| ADI-10090 | VH 4-39 | QLQLQESGPGLVKPSET LSLTCTVSG(SEQ ID NO:45) | GSIWSSSYYWT (SEQ ID NO:13) | WIRQPPGKGLEW IG(SEQ ID NO:46) | SINYRGSTYYNPS LKS(SEQ ID NO:17) | RVTISVDTSKNQFSLKLS SVTAADTAVYYC(SEQ ID NO:47) | ARENSGVVPAAGPN WFDP(SEQ ID NO:18) | WGQGTLVTVS S(SEQ ID NO:48) |
| Consensus | | | GSX1X2SX3 X4YYWX5 (wherein X1 is selected from V and I; X2 is selected from S, V, R, G, and W; X3 is selected from S and A; X4 is selected from S and A; and X5 is selected from G, A, S, and T) (SEQ ID NO: 20) | | SX1X2YX3GSTY YNPX4LKS (wherein X1 is selected from I and A; X2 is selected from Y and N; X3 is selected from S, K and R; and X4 is selected from S and F) (SEQ ID NO: 21) | | AREX1SGVVPAA GPNWFX2P (wherein X1 is selected from G and N; and X2 is selected from D and G) (SEQ ID NO: 22) | |

FIG. 4A
(continued)

| IgG ADI name | VL germline | VL FR1 | VL CDR1 | VL FR2 | VL CDR2 | VL FR3 | VL CDR3 | VL FR4 |
|---|---|---|---|---|---|---|---|---|
| ADI-0 2396 | VK3 -11 | EIVLTQSPATLSLSPG ERATLSC(SEQ ID NO:49) | RASQSVSSY LA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-0 9111 | VK3 -11 | EIVLTQSPATLSLSPG ERATLSC(SEQ ID NO:49) | RASQSVSSY LA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-0 9112 | VK3 -11 | EIVLTQSPATLSLSPG ERATLSC(SEQ ID NO:49) | RASQSVSSY LA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-0 9113 | VK3 -11 | EIVLTQSPATLSLSPG ERATLSC(SEQ ID NO:49) | RASQSVSSY LA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-1 0085 | VK3 -11 | EIVLTQSPATLSLSPG ERATLSC(SEQ ID NO:49) | RASQSVSSY LA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |

FIG. 4B

| IgG ADI name | VL germline | VL FR1 | VL CDR1 | VL FR2 | VL CDR2 | VL FR3 | VL CDR3 | VL FR4 |
|---|---|---|---|---|---|---|---|---|
| ADI-1 0086 | VK3 -11 | EIVLTQSPATLSLSPG ERATLSC(SEQ ID NO:49) | RASQSVSSY LA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-1 0087 | VK3 -11 | EIVLTQSPATLSLSPG ERATLSC(SEQ ID NO:49) | RASQSVSSY LA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-1 0088 | VK3 -11 | EIVLTQSPATLSLSPG ERATLSC(SEQ ID NO:49) | RASQSVSSY LA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-1 0089 | VK3 -11 | EIVLTQSPATLSLSPG ERATLSC(SEQ ID NO:49) | RASQSVSSY LA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-1 0090 | VK3 -11 | EIVLTQSPATLSLSPG ERATLSC(SEQ ID NO:49) | RASQSVSSY LA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |

FIG. 4B

ADI - 02396（SEQ ID NO:23）
QLQLQESGPGLVKPSETLSLTCTVSGGSISSSSYYWGWIRQPPGKGLEWIGSIYYSGSTYYNPSLKSRVTISVDTSKNQFSLKLSSVTAADTAVYYCAREGSGVVPAAGPNWFDP
WGQGTLVTVSS

ADI - 09111（SEQ ID NO:25）
QLQLQESGPGLVKPSETLSLTCTVSGGSISSSSYYWGWIRQPPGKGLEWIGSIYYSGSTYYNPSLKSRVTISVDTSKNQFSLKLSSVTAADTAVYYCARENSGVVPAAGPNW
FDPWGQGTLVTVSS

ADI - 09112（SEQ ID NO:26）
QLQLQESGPGLVKPSETLSLTCTVSGGSISSSSYYWGWIRQPPGKGLEWIGSIYYSGSTYYNPFLKSRVTISVDTSKNQFSLKLSSVTAADTAVYYCARENSGVVPAAGPNW
FGPWGQGTLVTVSS

ADI - 09113（SEQ ID NO:27）
QLQLQESGPGLVKPSETLSLTCTVSGGSVSSSSYYWGWIRQPPGKGLEWIGSAYYSGSTYYNPSLKSRVTISVDTSKNQFSLKLSSVTAADTAVYYCARENSGVVPAAGPN
WFDPWGQGTLVTVSS

ADI - 10085（SEQ ID NO:28）
QLQLQESGPGLVKPSETLSLTCTVSGGSIVSSSYYWAWIRQPPGKGLEWIGSINYKGSTYYNPSLKSRVTISVDTSKNQFSLKLSSVTAADTAVYYCARENSGVVPAAGPN
WFGPWGQGTLVTVSS

ADI - 10086（SEQ ID NO:29）
QLQLQESGPGLVKPSETLSLTCTVSGGSIRSSAYYWGWIRQPPGKGLEWIGSINYRGSTYYNPSLKSRVTISVDTSKNQFSLKLSSVTAADTAVYYCARENSGVVPAAGPN
WFGPWGQGTLVTVSS

ADI - 10087（SEQ ID NO:30）
QLQLQESGPGLVKPSETLSLTCTVSGGSISSASYYWSWIRQPPGKGLEWIGSINYRGSTYYNPSLKSRVTISVDTSKNQFSLKLSSVTAADTAVYYCARENSGVVPAAGPN
WFGPWGQGTLVTVSS

ADI - 10088（SEQ ID NO:31）
QLQLQESGPGLVKPSETLSLTCTVSGGSIGSSSYYWAWIRQPPGKGLEWIGSINYRGSTYYNPSLKSRVTISVDTSKNQFSLKLSSVTAADTAVYYCARENSGVVPAAGPN
WFDPWGQGTLVTVSS

ADI - 10089（SEQ ID NO:32）
QLQLQESGPGLVKPSETLSLTCTVSGGSIGSSSYYWTWIRQPPGKGLEWIGSINYRGSTYYNPSLKSRVTISVDTSKNQFSLKLSSVTAADTAVYYCARENSGVVPAAGPN
WFDPWGQGTLVTVSS

ADI - 10090（SEQ ID NO:33）
QLQLQESGPGLVKPSETLSLTCTVSGGSIWSSSYYWTWIRQPPGKGLEWIGSINYRGSTYYNPSLKSRVTISVDTSKNQFSLKLSSVTAADTAVYYCARENSGVVPAAGPN
WFDPWGQGTLVTVSS

FIG. 5A

SEQ ID NO:24
EIVLTQSPATLSLSPGERATLSCRASQSVSSYLAWYQQKPGQAPRLLIYDASNRATGIPARFSGSGSGTDFTLTISSLEPEDFAVYYCQQRRNWFTFGGGTKVEIK

FIG. 5B

PREPARATION COMPRISING ANTI-PCSK9 ANTIBODY AND USE THEREOF

TECHNICAL FIELD

The present invention relates to the field of antibody preparations, and in particular to a pharmaceutical preparation comprising an antibody specifically binding to proprotein convertase subtilisin/kexin type 9 (PCSK9) (referred to as anti-PCSK9 antibody hereinafter) and/or an antibody fragment thereof. Furthermore, the present invention relates to therapeutic and diagnostic use of the preparation.

SEQUENCE LISTING

The application contains a Sequence Listing which has been submitted electronically in ASCII format and is hereby incorporated by reference in its entirety. Said ASCII copy, created on Mar. 22, 2021, is named 11275-009037-USO_ST25.txt and is 79,062 bytes in size.

BACKGROUND

Elevated cholesterol level in serum is an important risk factor resulting in cardiovascular events. At present, cholesterol-lowering drugs with multiple mechanisms of action have been launched or are under development. Among them, anti-PCSK9 monoclonal antibodies have drawn extensive attention because of their good safety and efficacy (Zhao Shuiping, et al., *Chinese Guideline for the Management of Dyslipidemia in Adults* (2016 Revised Edition). *Chinese Circulation Journal* 31 (10): 937-953, 2016).

With high specificity in action, mild adverse reaction and other advantages, monoclonal antibody drugs have become the mainstream of drug development in many disease fields, and anti-PCSK9 monoclonal antibody drugs that reduce LDL-C by reducing LDLR endocytosis are a current research hotspot. With a remarkable effect in reducing LDL-C, good safety and convenience in administration, anti-PCSK9 monoclonal antibodies are drugs marking a major breakthrough in the field of lipid-lowering treatment.

There is still a demand for alternative anti-PCSK9 antibodies. Specifically, there is a demand for alternative anti-PCSK9 antibodies that have a high affinity for PCSK9, a reliable cell strain source, high stability, and high efficiency in reducing LDL-C. More specifically, there is a demand for alternative anti-PCSK9 antibodies that efficiently reduce LDL-C and provide a long duration of effect (such as long-lasting inhibition for LDL-C level). Such antibodies will also preferably have physical and chemical properties that are favorable for development, manufacturing or preparation. At present, most of the monoclonal antibody drugs on the market are administrated by intravenous injection. However, subcutaneous injection has become a preferred mode of injection because patients with some certain chronic diseases hope to be self-medicated at home. Since the volume for subcutaneous injection is generally limited to 1.0 mL to 1.5 mL, the antibody preparation needs to have a high concentration (≥100 mg/mL) to meet the requirements for clinical dosage. High-concentration antibody preparations, however, also face a great challenge of high viscosity, because high-viscosity preparations will bring great difficulty to the downstream process and subcutaneous administration of drugs with a syringe. Under high concentrations, proteins are often less stable and are likely to aggregate and granulate. Moreover, the instability of protein conformations will also lead to a significant change in chemical stability such as charge heterogeneity.

In addition, as biomacromolecules, monoclonal antibodies have a very complex structure. In the process of production, expressed antibody molecules will undergo various post-translational modification and degradation, such as N-terminus cyclization, glycosylation, deamidization, isomerization, oxidation, fragmentation and disulfide bond mispairing. These quality attributes may affect the safety and effectiveness of final products, so it is also very important to control the correctness and consistency of product quality.

There is a need in the art to provide a liquid preparation comprising an anti-PCSK9 antibody with low viscosity, stability and high concentration.

SUMMARY

PCSK9 is an important and beneficial therapeutic target. The present invention also provides a liquid antibody preparation comprising an anti-PCSK9 antibody or a fragment thereof (such as the anti-PCSK9 antibody defined herein). The present invention also provides an antibody targeting PCSK9.

I. Antibody Preparation Disclosed Herein

In one aspect, the present invention provides a liquid antibody preparation, which comprises:

(i) an anti-PCSK9 antibody or a fragment thereof (such as an antigen-binding fragment);
(ii) a buffer;
(iii) a viscosity inhibitor; and
(iv) a surfactant.

In one embodiment, the concentration of the anti-PCSK9 antibody or the fragment thereof in the liquid antibody preparation disclosed herein is about 50 mg/mL to about 200 mg/mL. In another embodiment, the concentration of the anti-PCSK9 antibody or the fragment thereof in the liquid antibody preparation disclosed herein is about 100 mg/mL to about 200 mg/mL. In another embodiment, the concentration of the anti-PCSK9 antibody or the fragment thereof in the liquid antibody preparation disclosed herein is about 100 mg/mL. In another embodiment, the concentration of the anti-PCSK9 antibody or the fragment thereof in the liquid antibody preparation disclosed herein is about 125 mg/mL. In another embodiment, the concentration of the anti-PCSK9 antibody or the fragment thereof in the liquid antibody preparation disclosed herein is about 150 mg/mL. In another embodiment, the concentration of the anti-PCSK9 antibody or the fragment thereof in the liquid antibody preparation disclosed herein is about 175 mg/mL. In another embodiment, the concentration of the anti-PCSK9 antibody or the fragment thereof in the liquid antibody preparation disclosed herein is about 200 mg/mL.

In one embodiment, the anti-PCSK9 antibody is any antibody binding to PCSK9 proteins (such as human PCSK9), such as a polyclonal antibody, a monoclonal antibody or a combination of the two. Preferably, in one embodiment, the anti-PCSK9 antibody is a monoclonal antibody. In one embodiment, the anti-PCSK9 antibody or the fragment thereof is the anti-PCSK9 antibody or the fragment thereof defined herein.

In one embodiment, the concentration of the buffer in the liquid antibody preparation disclosed herein is about 0.01 mg/mL to 50 mg/mL. In one embodiment, the concentration of the buffer in the liquid antibody preparation disclosed herein is about 0.1 mg/mL to 50 mg/mL. In one embodiment, the concentration of the buffer in the liquid antibody preparation disclosed herein is about 0.2 mg/mL to 10 mg/mL. In one embodiment, the concentration of the buffer in the liquid antibody preparation disclosed herein is about 0.5 mg/mL to 2.5 mg/mL. In one embodiment, the concentration of the buffer in the liquid antibody preparation disclosed herein is about 1.0 mg/ml to 2.0 mg/mL. In one embodiment, the concentration of the buffer in the liquid antibody preparation disclosed herein is about 1.5 mg/mL.

In one embodiment, the buffer is selected from histidine, glutamate, phosphate, acetate, citrate, and tris(hydroxymethyl)aminomethane. In one embodiment, the buffer is histidine.

In one embodiment, the concentration of the viscosity inhibitor in the liquid antibody preparation disclosed herein is about 10 mmol/L to 1000 mmol/L. In one embodiment, the concentration of the viscosity inhibitor in the liquid antibody preparation disclosed herein is about 20 mmol/L to 500 mmol/L. In one embodiment, the concentration of the viscosity inhibitor in the liquid antibody preparation disclosed herein is about 50 mmol/L to 300 mmol/L. In one embodiment, the concentration of the viscosity inhibitor in the liquid antibody preparation disclosed herein is about 50 mmol/L to 200 mmol/L.

In one embodiment, the viscosity inhibitor is selected from sugar alcohols (such as sorbitol), arginine, arginine hydrochloride, sodium thiocyanate, ammonium thiocyanate, ammonium sulfate, ammonium chloride, calcium chloride, zinc chloride, sodium acetate, and combinations thereof. In one embodiment, the viscosity inhibitor is sorbitol. In one embodiment, the viscosity inhibitor is sorbitol with a concentration of about 1% to 6% (w/v). In one embodiment, the viscosity inhibitor is sorbitol with a concentration of about 1% to 6% (w/v), and the liquid preparation does not comprise other viscosity inhibitors. In one embodiment, the viscosity inhibitor is a combination of sorbitol and arginine or arginine salt (preferably arginine hydrochloride). In one embodiment, the viscosity inhibitor is a combination of sorbitol and arginine or arginine salt (preferably arginine hydrochloride), wherein the concentration of sorbitol is about 1% to 6% (w/v), preferably about 2% to 4% (w/v), and more preferably about 3% (w/v), and the concentration of arginine or arginine salt (preferably arginine hydrochloride) is about 50 mmol/L to 180 mmol/L, preferably about 70 mmol/L to 150 mmol/L, and more preferably about 90 mmol/L. In one embodiment, the viscosity inhibitor is a combination of sorbitol and arginine or arginine salt (preferably arginine hydrochloride), wherein the concentration of sorbitol is about 1% to 6% (w/v), preferably about 2% to 4% (w/v), and more preferably about 3% (w/v), and the concentration of arginine or arginine salt is about 50 mmol/L to 180 mmol/L, preferably about 70 mmol/L to 150 mmol/L, and more preferably about 90 mmol/L, and the liquid preparation does not comprise other viscosity inhibitors. In one embodiment, the concentration of the surfactant is about 0.01 mg/mL to 5 mg/mL. In one embodiment, the concentration of the surfactant is about 0.05 mg/mL to 1 mg/mL. In one embodiment, the concentration of the surfactant is about 0.1 mg/mL to 0.5 mg/mL. In one embodiment, the concentration of the surfactant is about 0.3 mg/mL.

In one embodiment, the surfactant is a nonionic surfactant. In one embodiment, the surfactant is, for example, Pluronics® (poloxamers), polysorbate-80, polysorbate-60, polysorbate-40, or polysorbate-20.

In one embodiment, the liquid preparation disclosed herein comprises a solvent, and preferably, the solvent is selected from water for injection, organic solvents for injection (including but not limited to oil for injection, ethanol, and propylene glycol), and combinations thereof.

In one embodiment, the pH of the liquid preparation is about 5.0 to 6.0. In one embodiment, the pH of the liquid preparation is about 5.2 to 5.8. In one embodiment, the pH of the liquid preparation is about 5.4 to 5.6. In one embodiment, the pH of the liquid preparation is about 5.5.

In one embodiment, the viscosity of the liquid preparation at 25° C. is about 1.0 to 20 centipoises. In one embodiment, the viscosity of the liquid preparation at 25° C. is about 1.0 to 10 centipoises. In one embodiment, the viscosity of the liquid preparation at 25° C. is about 1.0, 2.0, 3.0, 4.0, 5.0, 6.0, 7.0, 8.0, 9.0, or 10.0 centipoises. In one embodiment, the viscosity of the liquid preparation at 25° C. is about 5.0 to 7.0 centipoises. In one embodiment, the viscosity of the liquid preparation at 25° C. is about 5.2 centipoises. In one embodiment, the viscosity of the liquid preparation at 25° C. is about 6.0 centipoises.

In one embodiment, the liquid preparation is a pharmaceutical preparation, preferably an injection, more preferably a subcutaneous injection.

In one preferred embodiment, the liquid antibody preparation disclosed herein comprises:

(i) about 100 mg/mL to 200 mg/mL of an anti-PCSK9 antibody or a fragment thereof;
(ii) about 0.2 mg/mL to 10 mg/mL of histidine;
(iii) about 1% to 6% (w/v) of sorbitol; and
(iv) about 0.05 mg/mL to 1 mg/mL of polysorbate-80 or polysorbate-20;

wherein the pH of the liquid preparation is about 5.0 to 6.0.

In one more preferred embodiment, the liquid antibody preparation disclosed herein also comprises water for injection.

In one preferred embodiment, the liquid antibody preparation disclosed herein comprises:

(i) about 100 mg/mL to 200 mg/mL of an anti-PCSK9 antibody or a fragment thereof;
(ii) about 0.2 mg/mL to 10 mg/mL of histidine;
(iii) about 1% to 6% of sorbitol and about 50 mmol/L to 180 mmol/L of arginine or arginine salt; and
(iv) about 0.05 mg/mL to 1 mg/mL of polysorbate-80 or polysorbate-20;

wherein the pH of the liquid preparation is about 5.0 to 6.0.

In one more preferred embodiment, the liquid antibody preparation disclosed herein also comprises water for injection.

In one embodiment, after the liquid preparation comprising an anti-PCSK9 antibody disclosed herein is stored at about −80° C. to about 45° C., such as −80° C., about −30° C., about −20° C., about 0° C., about 5° C., about 25° C., about 35° C., about 37° C., about 42° C. or about 45° C., for at least 14 days, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, at least 36 months, or longer, the purity of the anti-PCSK9 antibody or a fragment thereof decreases by no more than 10%, for example, no more than 5%, 4%, 3%, 2%, 1%, 0.5%, or 0.1%, as detected by SEC-HPLC.

In one embodiment, after the liquid preparation comprising an anti-PCSK9 antibody disclosed herein is stored at about −80° C. to about 45° C., such as −80° C., about −30° C., about −20° C., about 0° C., about 5° C., about 25° C., about 35° C., about 37° C., about 42° C. or about 45° C., for at least 14 days, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, at least 36 months, or longer, the purity of the anti-PCSK9 antibody or a fragment thereof decreases by no more than 10%, for example, no more than 5%, 4%, 3%, 2%, 1%, 0.5%, or 0.1%, as detected by non-reduced CE-SDS.

In one embodiment, after the liquid preparation comprising an anti-PCSK9 antibody disclosed herein is stored at about −80° C. to about 45° C., such as −80° C., about −30° C., about −20° C., about 0° C., about 5° C., about 25° C., about 35° C., about 37° C., about 42° C., or about 45° C., for at least 14 days, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, at least 36 months, or longer, the charge heterogeneity of the anti-PCSK9 antibody or a fragment thereof changes by no more than 10%, for example, no more than 5%, 4%, 3%, 2%, 1%, 0.5%, or 0.1%, as detected by CEX-HPLC.

The preparation disclosed herein has a high antibody concentration, a low viscosity suitable for administration (particularly subcutaneous administration), and a high physical and chemical stability, and is less prone to aggregate and granulate and exhibit heterogeneity change when stored. These advantages are very beneficial to the production of complete, effective, and highly consistent clinical drugs.

The inventors surprisingly found that sorbitol can be used as a viscosity inhibitor for the liquid preparation comprising an anti-PCSK9 antibody, in which case a liquid preparation comprising an anti-PCSK9 antibody or a fragment thereof having low viscosity and high concentration can be obtained without adding other viscosity inhibitors, and the liquid preparation has high stability. In addition, the inventors surprisingly found that a combination of sorbitol and arginine as a viscosity inhibitor can better reduce the viscosity of the liquid preparation comprising an anti-PCSK9 antibody and enable a high-concentration liquid preparation comprising an anti-PCSK9 antibody or a fragment thereof to have lower viscosity suitable for subcutaneous injection lower viscosity suitable for subcutaneous injection, and the liquid preparation comprising an anti-PCSK9 antibody has higher stability (see examples 10-12).

Therefore, in another aspect, the present invention provides use of sugar alcohol as a viscosity inhibitor for the liquid preparation comprising an anti-PCSK9 antibody.

In one embodiment, the concentration of the sugar alcohol in the liquid preparation comprising an anti-PCSK9 antibody is about 1% to 6% (w/v), preferably about 2% to 4% (w/v), and more preferably about 3% (w/v). In one embodiment, the sugar alcohol is preferably sorbitol.

In another aspect, the present invention provides use of sugar alcohol as a viscosity inhibitor in preparing the liquid preparation comprising an anti-PCSK9 antibody.

In one embodiment, the present invention provides use of sugar alcohol as the only viscosity inhibitor in preparing the liquid preparation comprising an anti-PCSK9 antibody.

In one embodiment, the concentration of the sugar alcohol in the liquid preparation comprising an anti-PCSK9 antibody is about 1% to 6% (w/v), preferably about 2% to 4% (w/v), and more preferably about 3% (w/v). In one embodiment, the sugar alcohol is preferably sorbitol.

In another aspect, the present invention provides use of a combination of sugar alcohol and arginine (or arginine salt, preferably arginine hydrochloride) as a viscosity inhibitor for the liquid preparation comprising an anti-PCSK9 antibody.

In one embodiment, the concentration of the sugar alcohol in the liquid preparation comprising an anti-PCSK9 antibody is about 1% to 6% (w/v), preferably about 2% to 4% (w/v), and more preferably about 3% (w/v); and the concentration of arginine or arginine salt (preferably arginine hydrochloride) is about 50 mmol/L to 180 mmol/L, preferably about 70 mmol/L to 150 mmol/L, and more preferably about 90 mmol/L. In one embodiment, the sugar alcohol is preferably sorbitol. In another aspect, the present invention provides use of a combination of sugar alcohol and arginine (or arginine salt, preferably arginine hydrochloride) as a viscosity inhibitor in preparing the liquid preparation comprising an anti-PCSK9 antibody.

In one embodiment, the present invention provides use of a combination of sugar alcohol and arginine (or arginine salt, preferably arginine hydrochloride) as the only viscosity inhibitor in preparing the liquid preparation comprising an anti-PCSK9 antibody.

In one embodiment, the concentration of the sugar alcohol in the liquid preparation comprising an anti-PCSK9 antibody is about 1% to 6% (w/v), preferably about 2% to 4% (w/v), and more preferably about 3% (w/v); and the concentration of arginine or arginine salt (preferably arginine hydrochloride) is about 50 mmol/L to 180 mmol/L, preferably about 70 mmol/L to 150 mmol/L, and more preferably about 90 mmol/L. In one embodiment, the sugar alcohol is preferably sorbitol.

In another aspect, the present invention provides a solid preparation obtained by lyophilizing the aforementioned liquid preparation. Before use, the solid preparation can be reconstituted in a suitable solvent to give the liquid preparation disclosed herein.

In another aspect, the present invention provides a method for preparing the liquid preparation disclosed herein, which comprises the following steps:

a. providing an anti-PCSK9 antibody or a fragment thereof;
b. adding a buffer and a viscosity inhibitor;
c. adding a surfactant; and
d. optionally conducting sterile filtration to give the liquid preparation disclosed herein.

In one embodiment, the anti-PCSK9 antibody or the fragment thereof in step a is a separated and purified anti-PCSK9 antibody.

In one embodiment, the anti-PCSK9 antibody or the fragment thereof in step a is provided in the form of a solution, preferably an aqueous solution.

In one embodiment, before step b, the anti-PCSK9 antibody or the fragment thereof is concentrated by being centrifuged using an ultrafiltration centrifuge tube having a molecular weight cutoff of, for example, about 30 KD.

In one embodiment, the buffer and the viscosity inhibitor in step b are provided in the form of a solution, preferably an aqueous solution.

In one embodiment, after step b, the anti-PCSK9 antibody or the fragment thereof is concentrated by ultrafiltration and centrifugation and then diluted with the solutions, preferably aqueous solutions, of the buffer and the viscosity inhibitor, and this is repeated until the replacement is completed.

In one embodiment, before step c, the concentration of the anti-PCSK9 antibody or the fragment thereof is adjusted.

The anti-PCSK9 antibody or the fragment thereof, the buffer, the viscosity inhibitor, and the surfactant are as described herein, and doses and/or concentrations thereof are as described for, or can be appropriately determined by, the liquid preparation disclosed herein.

In one embodiment, the method for preparing the liquid preparation disclosed herein comprises the following steps:

i. providing a separated and purified anti-PCSK9 antibody, optionally adding the antibody to an ultrafiltration centrifuge tube with a molecular weight cutoff of about 30 KD, and concentrating the antibody by centrifugation;
ii. diluting the anti-PCSK9 antibody with solutions, preferably aqueous solutions, of a buffer and a viscosity inhibitor (preferably, the variety, concentration, and solution pH of the buffer and the viscosity inhibitor are as defined above and as defined for the liquid preparation disclosed herein in the definition section, and more preferably, the buffer is histidine and the viscosity inhibitor is arginine and/or sorbitol) and then concentrating, and repeating this until the replacement is completed;
iii. adjusting the concentration of replaced protein to a concentration defined for the liquid preparation disclosed herein;
iv. adding a surfactant or a solution thereof, preferably an aqueous solution, and adjusting the final concentration of the surfactant to a concentration defined for the liquid preparation disclosed herein;
v. optionally aseptically filtering the solution in step iv; and
vi. optionally aliquoting the solution into vials and capping the vials with rubber stoppers and aluminum-plastic caps to give the product.

In the embodiment, the anti-PCSK9 antibody is the anti-PCSK9 antibody defined herein.

II. Anti-PCSK9 Antibody Disclosed Herein

In some embodiments, an anti-PCSK9 antibody or an antibody fragment (preferably an antigen-binding fragment) binding to PCSK9 or a fragment thereof (preferably human PCSK9 protein) is provided.

In one aspect of the present invention, an anti-PCSK9 antibody and a fragment thereof (such as an antigen-binding fragment) are provided herein. In some embodiments, the anti-PCSK9 antibody inhibits or blocks the activity of PCSK9. In some embodiments, the anti-PCSK9 antibody disclosed herein has one or more of the following properties:

(1) binding to PCSK9 (preferably human PCSK9 protein), preferably with an equilibrium dissociation constant ($K_D$) less than or equal to about 1 μM, about 100 nM, about 10 nM, about 1 nM, about 0.1 nM, about 0.01 nM, or about 0.001 nM (e.g., $10^{-8}$ M or less, e.g., $10^{-8}$ M to $10^{-13}$ M, e.g., $10^{-9}$ M to $10^{-13}$ M);
(2) blocking the binding of PCSK9 (such as human PCSK9) to LDLR (such as human LDLR);
(3) enhancing the capability of restoring LDLR and/or inhibiting the decrease of LDL-C uptake induced by PCSK9, thus increasing the uptake of LDL-C by cells (such as hepatocytes); preferably, the antibody concentration is about 10 nM, 15 nM, 20 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM or more, e.g., about 10-100 nM and 15-70 nM; preferably, the capability of the antibody in increasing the uptake of LDL-C by cells is at least 2 times higher than that of a control antibody; and preferably, the control antibody is IgG or an antibody known in the art, such as Alirocumab, Evolocumab or Lodelcizumab;
(4) effectively preventing the internalization of LDLR in cells;
(5) (dose-dependently) lowering the level of LDL-C and/or the level of total cholesterol (TC) in serum;
(6) significantly lowering the level of LDL-C in serum over a long period of time, for example, a duration of response of more than 15, 16, 17, 18, 19, 20, or 21 days.

In some embodiments, the anti-PCSK9 antibody disclosed herein or the antigen-binding fragment thereof comprises a heavy chain variable region (VH), wherein the VH comprises:

(i) three complementarity determining regions (CDRs) contained in a VH of any of the antibodies listed in Table II, or
(ii) relative to the sequence of (i), a sequence comprising a total of at least one and no more than 5, 4, 3, 2, or 1 amino acid alteration (preferably amino acid replacement, and more preferably conservative replacement) in the three CDRs.

In some embodiments, the anti-PCSK9 antibody or the antigen-binding fragment thereof disclosed herein comprises a light chain variable region (VL), wherein the VL comprises:

(i) three complementarity determining regions (CDRs) contained in a VL set forth in SEQ ID NO: 24; or
(ii) relative to the sequence of (i), a sequence comprising a total of at least one and no more than 5, 4, 3, 2, or 1 amino acid alteration (preferably amino acid replacement, and more preferably conservative replacement) in the three CDRs.

In some embodiments, the anti-PCSK9 antibody or the antigen-binding fragment thereof disclosed herein comprises a heavy chain variable region VH and a light chain variable region VL, wherein, (a) the VH comprises:
(i) three complementarity determining regions (CDRs) contained in a VH of any of the antibodies listed in Table II, or
(ii) relative to the sequence of (i), a sequence comprising a total of at least one and no more than 5, 4, 3, 2, or 1 amino acid alteration (preferably amino acid replacement, and more preferably conservative replacement) in the three CDRs; and/or
(b) the VL comprises:
(i) three complementarity determining regions (CDRs) contained in a VL set forth in SEQ ID NO: 24; or
(ii) relative to the sequence of (i), a sequence comprising a total of at least one and no more than 5, 4, 3, 2, or 1 amino acid alteration (preferably amino acid replacement, and more preferably conservative replacement) in the three CDRs.

In a preferred embodiment, the VH comprises or consists of an amino acid sequence selected from SEQ ID NOs: 23, 25, 26, 27, 28, 29, 30, 31, 32, and 33.

In a preferred embodiment, the VL comprises or consists of an amino acid sequence set forth in SEQ ID NO: 24.

In a preferred embodiment, the anti-PCSK9 antibody or the antigen-binding fragment thereof disclosed herein comprises:

(a) three complementarity determining regions of a heavy chain variable region (HCDRs) set forth in SEQ ID NO: 23, 25, 26, 27, 28, 29, 30, 31, 32, or 33, and/or
(b) three complementarity determining regions of a light chain variable region (LCDRs) set forth in SEQ ID NO:24.

In a preferred embodiment, the anti-PCSK9 antibody or the antigen-binding fragment thereof disclosed herein comprises:

(a) three complementarity determining regions of a heavy chain variable region (HCDRs) set forth in SEQ ID NO: 23, 25, 26, 27, 28, 29, 30, 31, 32, or 33, and (b) three complementarity determining regions of a light chain variable region (LCDRs) set forth in SEQ ID NO:24.

In some embodiments, the anti-PCSK9 antibody or the antigen-binding fragment thereof disclosed herein comprises a heavy chain variable region (VH) and/or a light chain variable region (VL), wherein (i) the VH comprises complementarity determining regions (CDRs) HCDR1, HCDR2, and HCDR3, wherein the HCDR1 comprises or consists of an amino acid sequence selected from SEQ ID NOs: 1, 7, 8, 9, 10, 11, 12, 13, and 20, or the HCDR1 comprises an amino acid sequence having one, two, or three alterations (preferably amino acid replacements, and more preferably conservative replacements) compared with the amino acid sequence selected from SEQ ID NOs: 1, 7, 8, 9, 10, 11, 12, 13, and 20; the HCDR2 comprises or consists of an amino acid sequence selected from SEQ ID NOs: 2, 14, 15, 16, 17, and 21, or the HCDR2 comprises an amino acid sequence having one, two, or three alterations (preferably amino acid replacements, and more preferably conservative replacements) compared with the amino acid sequence selected from SEQ ID NOs: 2, 14, 15, 16, 17, and 21; and the HCDR3 comprises or consists of an amino acid sequence selected from SEQ ID NOs: 3, 18, 19, and 22, or the HCDR3 comprises an amino acid sequence having one, two, or three alterations (preferably amino acid replacements, and more preferably conservative replacements) compared with the amino acid sequence selected from SEQ ID NOs: 3, 18, 19, and 22;

and/or (ii) the VL comprises complementarity determining regions (CDRs) LCDR1, LCDR2, and LCDR3, wherein the LCDR1 comprises or consists of an amino acid sequence set forth in SEQ ID NO: 4, or the LCDR1 comprises an amino acid sequence having one, two, or three alterations (preferably amino acid replacements, and more preferably conservative replacements) compared with the amino acid sequence set forth in SEQ ID NO: 4; the LCDR2 comprises or consists of an amino acid sequence set forth in SEQ ID NO: 5, or the LCDR2 comprises an amino acid sequence having one, two, or three alterations (preferably amino acid replacements, and more preferably conservative replacements) compared with the amino acid sequence set forth in SEQ ID NO: 5; and the LCDR3 comprises or consists of an amino acid sequence set forth in SEQ ID NO: 6, or the LCDR3 comprises an amino acid sequence having one, two, or three alterations (preferably amino acid replacements, and more preferably conservative replacements) compared with the amino acid sequence set forth in SEQ ID NO: 6.

In a preferred embodiment, the present invention provides an anti-PCSK9 antibody or an antigen-binding fragment thereof comprising a heavy chain variable region (VH) and/or a light chain variable region (VL), wherein (a) the VH comprises:

(i) a combination of the HCDR1, HCDR2, and HCDR3 shown in Table I; or (ii) a variant of the HCDR combination in (i), comprising a total of at least one and no more than 5, 4, 3, 2, or 1 amino acid alteration (preferably amino acid replacement, and more preferably conservative replacement) in the three CDRs;

and/or (ii) the VL comprises:

(i) a combination of an LCDR1, an LCDR2, and an LCDR3 respectively comprising or consisting of amino acid sequences set forth in SEQ ID NOs: 4, 5, and 6; or (ii) a variant of the LCDR combination of (i), comprising a total of at least one and no more than 5, 4, 3, 2, or 1 amino acid alteration (preferably amino acid replacement, and more preferably conservative replacement) in the three CDRs.

In a preferred embodiment, the present invention provides an anti-PCSK9 antibody or an antigen-binding fragment thereof, comprising a heavy chain variable region (VH) and/or a light chain variable region (VL), wherein the VH comprises complementarity determining regions (CDRs) HCDR1, HCDR2, and HCDR3, and the VL comprises (CDRs) LCDR1, LCDR2, and LCDR3; and combinations of the HCDR1, HCDR2, HCDR3, LCDR1, LCDR2, and LCDR3 contained in the antibody or the antigen-binding fragment thereof are shown in the following table (Table I):

TABLE I

Exemplary combinations of the HCDR1, HCDR2, HCDR3, LCDR1, LCDR2, and LCDR3 in the antibody or the antigen-binding fragment thereof disclosed herein

| Combinations | HCDR1, which comprises or consists of an amino acid sequence set forth in the following SEQ ID Nos | HCDR2, which comprises or consists of an amino acid sequence set forth in the following SEQ ID Nos | HCDR3, which comprises or consists of an amino acid sequence set forth in the following SEQ ID Nos | LCDR1, which comprises or consists of an amino acid sequence set forth in the following SEQ ID Nos | LCDR2, which comprises or consists of an amino acid sequence set forth in the following SEQ ID Nos | LCDR3, which comprises or consists of an amino acid sequence set forth in the following SEQ ID Nos |
|---|---|---|---|---|---|---|
| (1) | SEQ ID NO: 1 | SEQ ID NO: 2 | SEQ ID NO: 3 | SEQ ID NO: 4 | SEQ ID NO: 5 | SEQ ID NO: 6 |
| (2) | SEQ ID NO: 1 | SEQ ID NO: 2 | SEQ ID NO: 18 | SEQ ID NO: 4 | SEQ ID NO: 5 | SEQ ID NO: 6 |
| (3) | SEQ ID NO: 1 | SEQ ID NO: 14 | SEQ ID NO: 19 | SEQ ID NO: 4 | SEQ ID NO: 5 | SEQ ID NO: 6 |
| (4) | SEQ ID NO: 7 | SEQ ID NO: 15 | SEQ ID NO: 18 | SEQ ID NO: 4 | SEQ ID NO: 5 | SEQ ID NO: 6 |

TABLE I-continued

Exemplary combinations of the HCDR1, HCDR2, HCDR3, LCDR1, LCDR2, and LCDR3 in the antibody or the antigen-binding fragment thereof disclosed herein

| Combinations | HCDR1, which comprises or consists of an amino acid sequence set forth in the following SEQ ID Nos | HCDR2, which comprises or consists of an amino acid sequence set forth in the following SEQ ID Nos | HCDR3, which comprises or consists of an amino acid sequence set forth in the following SEQ ID Nos | LCDR1, which comprises or consists of an amino acid sequence set forth in the following SEQ ID Nos | LCDR2, which comprises or consists of an amino acid sequence set forth in the following SEQ ID Nos | LCDR3, which comprises or consists of an amino acid sequence set forth in the following SEQ ID Nos |
|---|---|---|---|---|---|---|
| (5) | SEQ ID NO: 8 | SEQ ID NO: 16 | SEQ ID NO: 19 | SEQ ID NO: 4 | SEQ ID NO: 5 | SEQ ID NO: 6 |
| (6) | SEQ ID NO: 9 | SEQ ID NO: 17 | SEQ ID NO: 19 | SEQ ID NO: 4 | SEQ ID NO: 5 | SEQ ID NO: 6 |
| (7) | SEQ ID NO: 10 | SEQ ID NO: 17 | SEQ ID NO: 19 | SEQ ID NO: 4 | SEQ ID NO: 5 | SEQ ID NO: 6 |
| (8) | SEQ ID NO: 11 | SEQ ID NO: 17 | SEQ ID NO: 18 | SEQ ID NO: 4 | SEQ ID NO: 5 | SEQ ID NO: 6 |
| (9) | SEQ ID NO: 12 | SEQ ID NO: 17 | SEQ ID NO: 18 | SEQ ID NO: 4 | SEQ ID NO: 5 | SEQ ID NO: 6 |
| (10) | SEQ ID NO: 13 | SEQ ID NO: 17 | SEQ ID NO: 18 | SEQ ID NO: 4 | SEQ ID NO: 5 | SEQ ID NO: 6 |
| (11) | SEQ ID NO: 20 | SEQ ID NO: 21 | SEQ ID NO: 22 | SEQ ID NO: 4 | SEQ ID NO: 5 | SEQ ID NO: 6 |

In a preferred embodiment, the present invention provides an anti-PCSK9 antibody or an antigen-binding fragment thereof comprising a combination of the HCDR1, HCDR2, HCDR3, LCDR1, LCDR2, and LCDR3 shown in Table I.

In some embodiments, the anti-PCSK9 antibody or the antigen-binding fragment thereof disclosed herein comprises a heavy chain variable region (VH) and/or a light chain variable region (VL), wherein, (a) the heavy chain variable region VH (i) comprises or consists of an amino acid sequence having at least 90%, 91%, 92%, 93%, 94%, 95%, 96%, 97%, 98%, or 99% identity to an amino acid sequence selected from SEQ ID NOs: 23, 25, 26, 27, 28, 29, 30, 31, 32, and 33; or (ii) comprises or consists of an amino acid sequence selected from SEQ ID NO: 23, 25, 26, 27, 28, 29, 30, 31, 32, and 33; or (iii) comprises an amino acid sequence having one or more (preferably no more than 10, and more preferably no more than 5, 4, 3, 2, or 1) amino acid alterations (preferably amino acid replacements, and more preferably conservative amino acid replacements) compared with an amino acid sequence selected from SEQ ID NOs: 23, 25, 26, 27, 28, 29, 30, 31, 32, and 33, wherein preferably, the amino acid alterations do not occur in the CDRs;

and/or (b) the light chain variable region VL (i) comprises or consists of an amino acid sequence having at least 90%, 91%, 92%, 93%, 94%, 95%, 96%, 97%, 98%, or 99% identity to an amino acid sequence set forth in SEQ ID NO: 24;

(ii) comprises or consists of an amino acid sequence set forth in SEQ ID NO: 24; or (iii) comprises an amino acid sequence having one or more (preferably no more than 10, and more preferably no more than 5, 4, 3, 2, or 1) amino acid alterations (preferably amino acid replacements, and more preferably conservative amino acid replacements) compared with an amino acid sequence set forth in SEQ ID NO: 24, wherein preferably, the amino acid alterations do not occur in the CDRs.

In a preferred embodiment, the present invention provides an anti-PCSK9 antibody or an antigen-binding fragment thereof comprising a heavy chain variable region (VH) and a light chain variable region (VL), wherein combinations of the heavy chain variable region (VH) and the light chain variable region (VL) contained in the antibody or the antigen-binding fragment thereof are shown in the following table (Table II):

TABLE II

Exemplary combinations of the heavy chain variable region VH and light chain variable region VL in the antibody or the antigen-binding fragment thereof disclosed herein

| Combinations | VH, which comprises or consists of an amino acid sequence set forth in the following SEQ ID NOS | VL, which comprises or consists of an amino acid sequence set forth in the following SEQ ID NOS |
|---|---|---|
| (1) | SEQ ID NO:23 | SEQ ID NO:24 |
| (2) | SEQ ID NO:25 | SEQ ID NO:24 |
| (3) | SEQ ID NO:26 | SEQ ID NO:24 |
| (4) | SEQ ID NO:27 | SEQ ID NO:24 |
| (5) | SEQ ID NO:28 | SEQ ID NO:24 |
| (6) | SEQ ID NO:29 | SEQ ID NO:24 |
| (7) | SEQ ID NO:30 | SEQ ID NO:24 |
| (8) | SEQ ID NO:31 | SEQ ID NO:24 |
| (9) | SEQ ID NO:32 | SEQ ID NO:24 |
| (10) | SEQ ID NO:33 | SEQ ID NO:24 |

In some embodiments, the anti-PCSK9 antibody or the antigen-binding fragment thereof disclosed herein comprises a heavy chain and/or a light chain, wherein (a) the heavy chain (i) comprises or consists of an amino acid sequence having at least 85%, 90%, 91%, 92%, 93%, 94%, 95%, 96%, 97%, 98%, or 99% identity to an amino acid sequence selected from SEQ ID NOs: 34, 36, 37, 38, 39, 40, 41, 42, 43, and 44;

(ii) comprises or consists of an amino acid sequence selected from SEQ ID NO: 34, 36, 37, 38, 39, 40, 41, 42, 43, and 44; or (iii) comprises an amino acid sequence having one or more (preferably no more than 20 or 10, and more preferably no more than 5, 4, 3, 2, or 1) amino acid alterations (preferably amino acid replacements, and more preferably conservative amino acid replacements) compared with an amino acid sequence selected from SEQ ID NOs: 34, 36, 37, 38, 39, 40, 41, 42, 43, and 44, wherein preferably, the amino acid alterations do not occur in the CDRs of the heavy chain, and more preferably, the amino acid alterations do not occur in the heavy chain variable region; and/or (b) the light chain (i) comprises or consists of an amino acid sequence having at least 85%, 90%, 91%, 92%, 93%, 94%, 95%, 96%, 97%, 98%, or 99% identity to an amino acid sequence set forth in SEQ ID NO: 35;

(ii) comprises or consists of an amino acid sequence set forth in SEQ ID NO: 35; or (iii) comprises an amino acid sequence having one or more (preferably no more than 20 or 10, and more preferably no more than 5, 4, 3, 2, or 1) amino acid alterations (preferably amino acid replacements, and more preferably conservative amino acid replacements) compared with an amino acid sequence set forth in SEQ ID NO: 35, wherein preferably, the amino acid alterations do not occur in the CDRs of the light chain, and more preferably, the amino acid alterations do not occur in the light chain variable region.

In a preferred embodiment, the present invention provides an anti-PCSK9 antibody or an antigen-binding fragment thereof comprising a heavy chain and a light chain, wherein combinations of the heavy chain and the light chain contained in the antibody or the antigen-binding fragment thereof are shown in the following table (Table III):

TABLE III

Exemplary combinations of the heavy chain and light chain in the antibody or the antigen-binding fragment thereof disclosed herein

| Combinations | Heavy chain, which comprises or consists of an amino acid sequence set forth in the following SEQ ID NOS | Light chain, which comprises or consists of an amino acid sequence set forth in the following SEQ ID NOS |
|---|---|---|
| (1) | SEQ ID NO:34 | SEQ ID NO:35 |
| (2) | SEQ ID NO:36 | SEQ ID NO:35 |
| (3) | SEQ ID NO:37 | SEQ ID NO:35 |
| (4) | SEQ ID NO:38 | SEQ ID NO:35 |
| (5) | SEQ ID NO:39 | SEQ ID NO:35 |
| (6) | SEQ ID NO:40 | SEQ ID NO:35 |
| (7) | SEQ ID NO:41 | SEQ ID NO:35 |
| (8) | SEQ ID NO:42 | SEQ ID NO:35 |
| (9) | SEQ ID NO:43 | SEQ ID NO:35 |
| (10) | SEQ ID NO:44 | SEQ ID NO:35 |

In some embodiments, the antibody disclosed herein also encompasses a variant of the amino acid sequence of an anti-PCSK9 antibody, as well as an antibody that binds to the same epitope as any of the antibodies described above.

In certain embodiments, an antibody or an antibody fragment (preferably an antigen-binding fragment) that binds to PCSK9 or a fragment thereof is provided, wherein the antibody binds to an epitope within the fragment of PCSK9. In certain embodiments, an antibody or an antibody fragment that binds to PCSK9 or a fragment thereof is provided, wherein the antibody binds to an epitope within an amino acid fragment comprising human PCSK9 amino acid sequence set forth in SEQ ID NO: 53.

In some embodiments, the heavy chain and/or light chain of the anti-PCSK9 antibody or the fragment thereof disclosed herein further comprises a signal peptide sequence, such as METDTLLLWVLLLWVPGSTG.

In one embodiment of the present invention, the amino acid alteration described herein includes amino acid replacement, insertion or deletion. Preferably, the amino acid alteration described herein is an amino acid replacement, preferably a conservative replacement.

In a preferred embodiment, the amino acid alteration described herein occurs in a region outside the CDR (e.g., in FR). More preferably, the amino acid alteration described herein occurs in a region outside the heavy chain variable region and/or outside the light chain variable region.

In some embodiments, the replacement is a conservative replacement. A conservative replacement refers to the replacement of an amino acid by another amino acid of the same class, e.g., the replacement of an acidic amino acid by another acidic amino acid, the replacement of a basic amino acid by another basic amino acid, or the replacement of a neutral amino acid by another neutral amino acid. Exemplary replacements are shown in Table IV below:

TABLE IV

| Primitive residue | Exemplary replacement | Preferred conservative amino acid replacement |
|---|---|---|
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, Nle | Leu |
| Leu (L) | Nle, Ile, Val, Met, Ala, Phe | Ile |
| Lys (K) | Arg, Gln, Asn | Arg |
| Met (M) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Nle | Leu |

In certain embodiments, the replacement occurs in the CDRs of the antibody. Generally, an obtained variant has modifications (e.g., improvements) in certain biological properties (e.g., increased affinity) relative to the parent antibody, and/or will substantially retain certain biological properties of the parent antibody. Exemplary replacement variants are affinity mature antibodies.

In certain embodiments, the antibody disclosed herein is altered to increase or decrease the extent to which the antibody is glycosylated. Addition or deletion of glycosylation sites to an antibody can be conveniently achieved by altering the amino acid sequence such that one or more glycosylation sites are created or removed. When the antibody comprises an Fc region, carbohydrate attached thereto can be altered. In some applications, modifications that remove undesired glycosylation sites may be useful, for example, removing fucose modules to enhance antibody-dependent cellular cytotoxicity (ADCC) function (see Shield, et al. (2002) JBC277:26733). In other applications, galactosidylation modification can be carried out to modify complement-dependent cytotoxicity (CDC).

In certain embodiments, one or more amino acid modifications can be introduced into an Fc region of the antibody disclosed herein, thereby producing an Fc region variant, such that, for example, the efficacy of the antibody in treating diseases is enhanced. The Fc region variant may comprise a human Fc region sequence (such as human IgG1, IgG2, IgG3, or IgG4 Fc region) comprising an amino acid modification (such as replacement) at one or more amino acid positions. For examples of the Fc variant, see U.S. Pat. Nos. 7,332,581, 6,737,056, 6,737,056; WO 2004/056312 and Shields, et al., *J. Biol. Chem.* 9 (2): 6591-6604 (2001), U.S. Pat. No. 6,194,551, WO 99/51642 and Idusogie, et al., *J. Immunol.* 164:4178-4184 (2000), U.S. Pat. No. 7,371,826, Duncan & Winter, *Nature* 322:738-40 (1988); U.S. Pat. Nos. 5,648,260; 5,624,821; and WO 94/29351.

In certain embodiments, antibodies modified by cysteine engineering may need to be produced, such as "sulfo-MAb", wherein one or more residues of the antibodies are replaced by cysteine residues. A cysteine-modified antibody can be produced as described, for example, in U.S. Pat. No. 7,521, 541.

In certain embodiments, the antibody disclosed herein can be further modified to comprise other non-protein portions known in the art and readily available. Suitable portions for antibody derivatization include, but are not limited to, water-soluble polymers. Non-limiting examples of water-soluble polymers include, but are not limited to, polyethylene glycol (PEG), ethylene glycol/propylene glycol copolymer, carboxymethyl cellulose, glucan, polyvinyl alcohol, polyvinylpyrrolidone, poly-1,3-dioxane, poly-1,3,6-trioxane, ethylene/maleic anhydride copolymer, polyamino acid (homopolymer or random copolymer), and glucan or poly(n-vinylpyrrolidone), polyethylene glycol, propylene glycol homopolymer, polypropylene oxide/ethylene oxide copolymer, polyoxyethylated polyol (such as glycerol), polyvinyl alcohol, and mixtures thereof.

In some embodiments, the anti-PCSK9 antibody or the antigen-binding fragment thereof disclosed herein has one or more of the following properties:

(i) exhibiting binding affinity and/or specificity for PCSK9 (such as human PCSK9, preferably having an amino acid sequence set forth in SEQ ID NO: 53) identical with or similar to that of any one of the antibodies listed in Table C;

(ii) inhibiting (e.g., competitively inhibiting) binding of any one of the antibodies listed in Table C to PCSK9 (such as human PCSK9, preferably having the amino acid sequence set forth in SEQ ID NO: 53);

(iii) binding to an identical or overlapping epitope as any one of the antibodies listed in Table C;

(iv) competing with any one of the antibodies listed in Table C for binding to PCSK9 (such as human PCSK9, preferably having the amino acid sequence set forth in SEQ ID NO: 53);

(v) having one or more biological properties of any one of the antibodies listed in Table C.

In some embodiments, the anti-PCSK9 antibody disclosed herein is an IgG1 antibody, an IgG2 antibody, or an IgG4 antibody.

In some embodiments, the anti-PCSK9 antibody disclosed herein is a monoclonal antibody. In some embodiments, the anti-PCSK9 antibody disclosed herein is humanized. In some embodiments, the anti-PCSK9 antibody disclosed herein is a human antibody. In some embodiments, at least a portion of the framework sequence of the anti-PCSK9 antibody disclosed herein is a human consensus framework sequence. In one embodiment, the anti-PCSK9 antibody disclosed herein also encompasses an antibody fragment thereof. Examples of the antibody fragment include, but are not limited to, Fv, Fab, Fab', Fab'-SH, $F(ab')_2$, a diabody, a linear antibody, a single-chain antibody molecule (e.g., scFv), and a multispecific antibody formed from the antibody fragment.

An antibody is digested by papain to produce two identical antigen-binding fragments called "Fab" fragments, each having a single antigen-binding site, and a residual "Fc" fragment, the name of which reflects its ability to crystallize easily. An $F(ab')_2$ fragment having two antigen-binding sites and still being capable of being cross-linked with an antigen is produced by treatment of pepsin.

In some embodiments, the anti-PCSK9 antibody disclosed herein is a humanized antibody. Different methods for humanizing antibodies are known to those skilled, as summarized by Almagro & Fransson, the content of which is incorporated in its entirety herein by reference (Almagro J. C. and Fransson J (2008) *Frontiers in Bioscience* 13:1619-1633). Almagro & Fransson distinguish between rational approach and empirical approach. The rational approach is characterized by generating a few engineered antibody variants and assessing their binding or any other property of interest. If the designed variants do not produce expected results, a new round of design and evaluation will be launched. The rational approach includes CDR grafting, resurfacing, superhumanization, and human string content optimization. In contrast, the empirical approach is based on generating large humanized variant libraries, and selects the best clones using enrichment techniques or high-throughput screening. Thus, the empirical approach depends on a reliable selection and/or screening system capable of searching for a large number of antibody variants. In vitro display technologies such as phage display and ribosome display meet these requirements and are well known to those skilled. The empirical approach includes FR library construction, guided selection, framework-shuffling, and humaneering.

In some embodiments, the anti-PCSK9 antibody disclosed herein is a human antibody. The human antibody can be prepared using a variety of techniques known in the art. The human antibody is generally described in van Dijk and van de Winkel, *Curr. Opin. Pharmacol* 5:368-74 (2001) and Lonberg, *Curr. Opin. Immunol* 20:450-459 (2008).

In some embodiments, the anti-PCSK9 antibody disclosed herein is a chimeric antibody.

The antibody disclosed herein can be isolated by screening antibodies having desired activity in a combinatorial library. For example, various methods for generating phage display libraries and screening antibodies with desired binding characteristics in the libraries are known in the art. The methods are reviewed in, for example, Hoogenboom et al., *Methods in Molecular Biology* 178:1-37 (edited by O'Brien et al., Human Press, Totowa, NJ, 2001), and further described in, for example, McCafferty et al., *Nature* 348: 552-554; Clackso et al., *Nature* 352:624-628 (1991); Marks et al., *J. Mol. Biol.* 222:581-597 (1992); Marks and Bradbury, *Methods in Molecular Biology* 248:161-175 (edited by Lo, Human Press, Totowa, NJ, 2003); Sidhu et al., *J. Mol. Biol.* 338 (2): 299-310 (2004); Lee et al., *J. Mol. Biol* 340 (5): 1073-1093 (2004); Fellouse, *Proc. Natl. Acad. Sci. USA* 101 (34): 12467-12472 (2004); and Lee et al., *J. Immunol. Methods* 284 (1-2): 119-132 (2004).

In some embodiments, the present invention also encompasses an anti-PCSK9 monoclonal antibody ("conjugate or immunoconjugate") conjugated to other substances, such as a detectable label (such as fluorescent dye, enzyme, substrate, bioluminescent substance, radioactive substance, and chemiluminescent portion), a cytotoxic agent or an immunosuppressant. The cytotoxic agent includes any agent that is harmful to cells. Examples of the cytotoxic agent (such as a chemotherapeutic agent) suitable for forming the immunoconjugate are known in the art, see, for example, WO 05/103081.

In some embodiments, the antibody disclosed herein may be monospecific, bispecific, or multispecific. The multispecific monoclonal antibody may be specific to different epitopes of a target polypeptide or may comprise antigen-binding domains specific to more than one target polypeptide. See, for example, Tutt et al. (1991) *J. Immunol.* 147:60-69. The anti-PCSK9 monoclonal antibody may be linked to or co-expressed with another functional molecule (such as another peptide or protein). For example, the antibody or a fragment thereof may be functionally linked to one or more other molecules, such as another antibody or antibody fragment (for example, by chemical coupling, genetic fusion, non-covalent association, or other methods), to produce a bispecific or multispecific antibody having a second or more binding specificities.

In some embodiments, the antibody disclosed herein binds to human PCSK9 protein, such as human PCSK9 protein set forth in SEQ ID NO: 53.

III. Therapeutic Method and Use of the Antibody Disclosed Herein or Preparation Thereof In another aspect, the present invention relates to a method for inhibiting the binding of PCSK9 to LDL-receptor (LDLR) in a subject, wherein the method comprises administering to the subject an effective amount of any of the anti-PCSK9 antibody preparations described herein or the anti-PCSK9 antibody disclosed herein. The present invention also relates to use of any of the anti-PCSK9 antibody preparations described herein or the anti-PCSK9 antibody disclosed herein in preparing a drug for inhibiting the binding of PCSK9 to LDL-receptor (LDLR) in a subject.

In another aspect, the present invention relates to a method for lowering the cholesterol level of a subject, wherein the method comprises administering to the subject an effective amount of any of the anti-PCSK9 antibody preparations described herein or the anti-PCSK9 antibody disclosed herein. In one embodiment, cholesterol is LDL-cholesterol, preferably serum cholesterol. In another aspect, the present invention relates to a method for lowering the LDL-cholesterol level of a subject, comprising administering to the subject an effective amount of any of the anti-PCSK9 antibody preparations described herein or the anti-PCSK9 antibody disclosed herein. In some embodiments, the present invention relates to a method for lowering the LDL-cholesterol level in the serum of a subject, wherein the method comprises administering to the subject an effective amount of any of the anti-PCSK9 antibody preparations described herein or the anti-PCSK9 antibody disclosed herein. In another aspect, the present invention also relates to use of any of the anti-PCSK9 antibody preparations described herein or the anti-PCSK9 antibody disclosed herein in preparing a drug for lowering the cholesterol level (LDL-cholesterol level or serum LDL-cholesterol level in one embodiment) in a subject.

In another aspect, the present invention relates to a method for preventing or treating a disorder associated with increased LDL-cholesterol level in a subject, wherein the method comprises administering to the subject an effective amount of any of the anti-PCSK9 antibody preparations described herein or the anti-PCSK9 antibody disclosed herein. The present invention also relates to use of any of the anti-PCSK9 antibody preparations described herein or the anti-PCSK9 antibody disclosed herein in preparing a drug for treating a disorder associated with increased LDL-cholesterol level in a subject.

In one aspect, the present invention relates to a method for preventing or treating a cholesterol-related disease, wherein the method comprises administering to the subject an effective amount of any of the anti-PCSK9 antibody preparations described herein or the anti-PCSK9 antibody disclosed herein. The present invention also relates to use of any of the anti-PCSK9 antibody preparations described herein or the anti-PCSK9 antibody disclosed herein in preparing a drug for treating a cholesterol-related disease. Exemplary and non-limiting examples of the cholesterol-related disease will be provided hereinafter. In some embodiments, the cholesterol-related disease is hypercholesterolemia or hyperlipidaemia. In some embodiments, the present invention relates to a method for treating hypercholesterolemia and/or hyperlipidaemia, wherein the method comprises administering to the subject an effective amount of any of the anti-PCSK9 antibody preparations described herein or the anti-PCSK9 antibody disclosed herein. In some embodiments, the present invention also relates to use of any of the anti-PCSK9 antibody preparations described herein or the anti-PCSK9 antibody disclosed herein in preparing a drug for treating hypercholesterolemia and/or hyperlipidaemia.

In one aspect, the present invention relates to a method for preventing or treating any disease or disorder capable of being improved, alleviated, inhibited or prevented by eliminating, inhibiting, or reducing the activity of PCSK9. In some embodiments, diseases or disorders that can be treated or prevented by using statins can also be treated or prevented by using any of the anti-PCSK9 antibody preparations described herein or the anti-PCSK9 antibody disclosed herein. In some embodiments, diseases or disorders that can benefit from the prevention of cholesterol synthesis or the increase of LDLR expression can also be treated by using any of the anti-PCSK9 antibody preparations described herein or the anti-PCSK9 antibody disclosed herein.

In some embodiments, the method described herein also comprises administering to the subject an effective amount of an additional therapeutic agent in a combination therapy. In one embodiment, the present invention also relates to a combination product that comprises the antibody preparation or the antibody described herein and the additional therapeutic agent. In one embodiment, the additional therapeutic agent can increase the level of LDLR protein. In another embodiment, the additional therapeutic agent can decrease the level of LDL-cholesterol. In another embodiment, the additional therapeutic agent comprises statins. In another embodiment, the additional therapeutic agent is a statin. In some embodiments, the statin is selected from atorvastatin, fluvastatin, lovastatin, mevastatin, pitavastatin, pravastatin, rosuvastatin, simvastatin, and any combination thereof. In certain embodiments, the additional therapeutic agent is used to prevent and/or treat atherosclerosis and/or cardiovascular diseases. In certain embodiments, the additional therapeutic agent is used to lower the risk of cardiovascular event recurrence. In certain embodiments, the additional therapeutic agent is used to increase the level of HDL-cholesterol in a subject. In some embodiments, the subject or individual is a mammal, preferably a human.

The aforementioned combination therapy includes combined administration (wherein two or more therapeutic agents are contained in one preparation or separate preparations) and separate administration, wherein any of the anti-PCSK9 antibody preparations or the anti-PCSK9 antibody disclosed herein can be administered before, concurrently with, and/or after the administration of an additional therapeutic agent and/or an adjuvant.

In order to prevent or treat diseases, the appropriate dosage of the preparation or antibody disclosed herein (used alone or in combination with one or more other additional therapeutic agents) will depend on the type of the disease to be treated, the type of the antibody, the severity and progression of the disease, the purpose for which the antibody is administered (prophylactic or therapeutic), previous treatments, the clinical history of the patient, responses to the preparation or antibody, and the discretion of the attending physician. The antibody is suitably administered to a patient through a single treatment or through a series of treatments. The exemplary dosage range of the antibody includes 3 mg/kg to 30 mg/kg.

In other aspects, the present invention provides use of any of the anti-PCSK9 antibody preparations or the anti-PCSK9 antibody disclosed herein in the production or preparation of a drug used to treat the aforementioned related diseases or disorders.

In certain embodiments, any anti-PCSK9 antibody preparation disclosed herein or the anti-PCSK9 antibody disclosed herein can be prophylactically administered to prevent or alleviate the onset of hypercholesterolemia, hyperlipidemia, cardiovascular diseases, and/or any cholesterol-related disease. In certain embodiments, any anti-PCSK9 antibody preparation disclosed herein or the anti-PCSK9 antibody disclosed herein can be administered to treat existing hypercholesterolemia and/or hyperlipidemia and/or cardiovascular diseases and/or any cholesterol-related disease. In some embodiments, any anti-PCSK9 antibody preparation disclosed herein or the anti-PCSK9 antibody disclosed herein will delay the onset of a disorder and/or symptoms associated with the disorder.

IV. Others

In one aspect, the present invention provides a nucleic acid encoding any aforementioned anti-PCSK9 antibody or a fragment thereof. In one embodiment, a vector comprising the nucleic acid is provided. In one embodiment, the vector is an expression vector. In one embodiment, a host cell comprising the vector is provided. In one embodiment, the host cell is eukaryotic. In another embodiment, the host cell is selected from a yeast cell, a mammalian cell, or other cells suitable for preparing an antibody or an antigen-binding fragment thereof. In another embodiment, the host cell is prokaryotic.

In one embodiment, the present invention provides a method for preparing an anti-PCSK9 antibody or a fragment thereof (preferably an antigen binding fragment), wherein the method comprises culturing the host cell under conditions suitable for the expression of the nucleic acid encoding the antibody or the fragment thereof (preferably the antigen-binding fragment), and optionally isolating the antibody or the fragment thereof (preferably the antigen-binding fragment). In a certain embodiment, the method further comprises isolating the anti-PCSK9 antibody or the fragment thereof (preferably the antigen-binding fragment) from the host cell.

In one aspect, the present invention relates to a method for detecting PCSK9 protein in a sample, wherein the method comprises (a) contacting the sample with any of the anti-PCSK9 antibody preparations described herein or the antibody disclosed herein; and (b) detecting the formation of a complex between the anti-PCSK9 antibody or fragment thereof and the PCSK9 protein. In one embodiment, the anti-PCSK9 antibody is detectably labeled.

The present invention also encompasses any combination of the embodiments described herein. Any of the embodiments described herein or any combination thereof is applicable to any and all of the preparations or anti-PCSK9 antibodies or fragments thereof, the methods and the use described herein.

BRIEF DESCRIPTION OF THE DRAWINGS

FIG. 4A shows the sequence information of FRs and CDRs of heavy chains of exemplary antibodies of the present invention, and FIG. 4B shows the sequence information of FRs and CDRs of light chains of exemplary antibodies of the present invention.

FIG. 5A shows the sequence information of heavy chain variable regions of exemplary antibodies of the present invention, and FIG. 5B shows the sequence information of a light chain variable region of an exemplary antibody of the present invention.

DEFINITIONS

Figure 1:
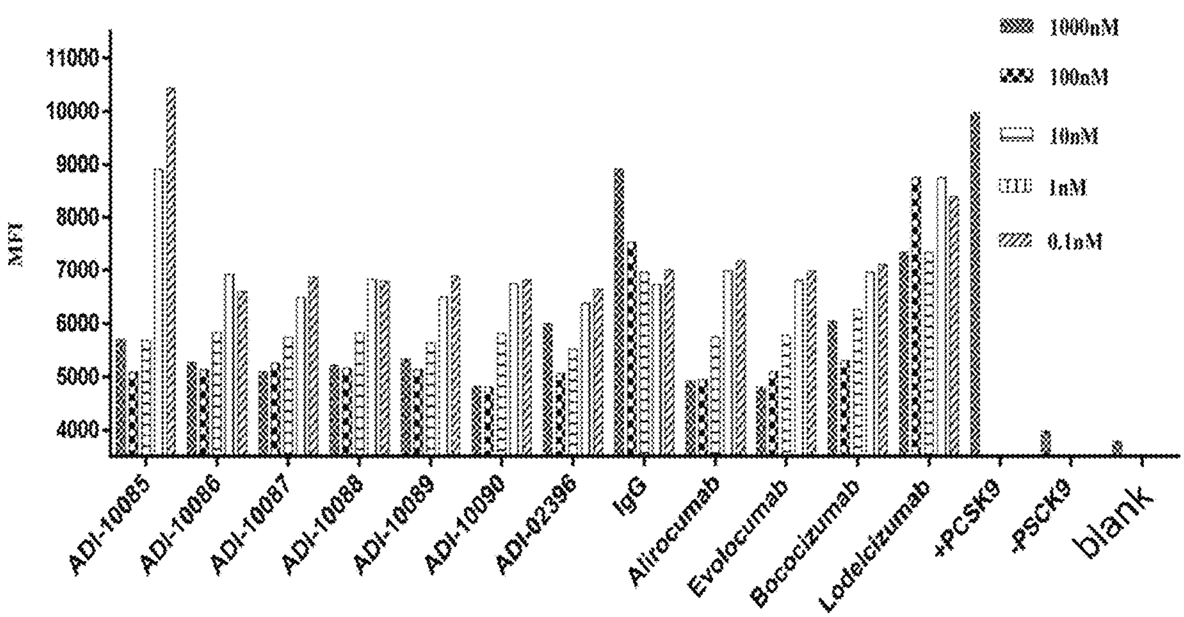
FIG. 1 shows the capability of anti-PCSK9 antibodies at different concentrations in blocking the binding of PCSK9 to LDLR.

The terms used in the present invention have the following definitions. If no definitions are given herein, the terms used in the present invention have the meanings commonly understood in the art. For the purpose of explaining this specification, the following definitions will be used, and wherever appropriate, terms used in the singular form may also include the plural form, and vice versa. It should be understood that the terminology used herein is for the purpose of describing specific embodiments only, and is not intended to be limiting.

As used herein, the term "and/or" refers to any one of the options or two or more of the options.

As used herein, the term "comprise" or "include" is intended to mean that the described elements, integers or steps are included, but not to the exclusion of any other elements, integers or steps. The term "comprise" or "include" used herein, unless otherwise specified, also encompasses the situation where the entirety consists of the described elements, integers or steps. For example, when referring to "comprise" an antibody variable region of a particular sequence, it is also intended to encompass an antibody variable region consisting of the specific sequence.

Unless otherwise stated, the term "proprotein convertase subtilisin/kexin type 9 (PCSK9)", "PCSK9", or "NARC-1" used herein refers to any natural PCSK9, preferably any natural PCSK9 from any vertebrate (including mammals, such as primates (e.g., humans) and rodents (e.g., mice and rats)). This term encompasses "full-length" unprocessed PCSK9 and PCSK9 in any form resulting from intracellular processing or any fragment thereof. This term also includes variants of naturally existing PCSK9, such as splice variants or allelic variants.

The term "activity of PCSK9" or "bioactivity of PCSK9" used herein includes any biological effect of PCSK9. In some embodiments, the activity of PCSK9 includes the ability of PCSK9 to interact with or bind to a substrate or a receptor. In some embodiments, the bioactivity of PCSK9 is the ability of PCSK9 to bind to LDL-receptor (LDLR). In some embodiments, PCSK9 binds to LDLR and catalyzes a reaction involving LDLR. In some embodiments, the activity of PCSK9 includes the ability of PCSK9 to decrease or reduce the availability of LDLR. In some embodiments, the bioactivity of PCSK9 includes the ability of PCSK9 to increase the amount of LDL in a subject. In some embodiments, the bioactivity of PCSK9 includes the ability of PCSK9 to reduce the amount of LDLR capable of binding to LDL in a subject. In some embodiments, the bioactivity of PCSK9 includes the ability of PCSK9 to reduce the amount of LDLR capable of binding to LDL. In some embodiments, the bioactivity of PCSK9 includes any bioactivity caused by PCSK9 signaling.

The term "anti-PCSK9 antibody", "anti-PCSK9", "PCSK9 antibody" or "antibody binding to PCSK9" refers to an antibody capable of binding to a PCSK9 protein or a fragment thereof with sufficient affinity so as to serve as a diagnostic agent and/or a therapeutic agent in targeting PCSK9. In one embodiment, an anti-PCSK9 antibody binds to an unrelated, non-PCSK9 protein to an extent less than about 10% of the extent to which the antibody binds to PCSK9, as measured, for example, by radioimmunoassay (RIA). In some embodiments, the equilibrium dissociation constant ($K_D$) of an anti-PCSK9 antibody is less than or equal to 1 μM, 100 nM, 10 nM, 1 nM, 0.1 nM, 0.01 nM, or 0.001 nM (e.g., $10^{-8}$ M or less, e.g., $10^{-8}$ M to $10^{-13}$ M, e.g., $10^{-9}$ M to $10^{-13}$ M).

"Antibody fragment" refers to a molecule different from an intact antibody, which comprises a portion of the intact antibody and binds to an antigen to which the intact antibody binds. Examples of the antibody fragment include, but are not limited to, Fv, Fab, Fab', Fab'-SH, $F(ab')_2$; a diabody; a linear antibody; a single-chain variable fragment (e.g., scFv); a single-domain antibody; a bivalent or bispecific antibody or a fragment thereof; a Camelidae antibody; and a bispecific antibody or multispecific antibody formed from antibody fragments.

As used herein, the term "epitope" refers to a moiety of an antigen (e.g., PCSK9) that specifically interacts with an antibody molecule.

An "antibody that binds to the same or overlapping epitope" as a reference antibody refers to an antibody that blocks 50% or more of the binding of the reference antibody to its antigen in a competition assay. Conversely, the reference antibody blocks 50% or more of the binding of the antibody to its antigen in a competition assay.

An antibody that competes with a reference antibody to bind to its antigen refers to an antibody that blocks more than 50%, 60%, 70%, 80%, 90%, or 95% of the binding of the reference antibody to its antigen in a competition assay. Conversely, the reference antibody blocks more than 50%, 60%, 70%, 80%, 90%, or 95% of the binding of the antibody to its antigen in a competition assay. Numerous types of competitive binding assays can be used to determine whether an antibody competes with another, such as direct or indirect solid-phase radioimmunoassay (RIA), direct or indirect solid-phase enzyme immunoassay (EIA), and sandwich competition assay (see, e.g., Stahli et al., 1983, *Methods in Enzymology* 9:242-253).

An antibody that inhibits (e.g., competitively inhibits) the binding of a reference antibody to its antigen refers to an antibody that inhibits more than 50%, 60%, 70%, 80%, 90%, or 95% of the binding of the reference antibody to its antigen. Conversely, the reference antibody inhibits more than 50%, 60%, 70%, 80%, 90%, or 95% of the binding of the antibody to its antigen. The binding of an antibody to its antigen can be measured by affinity (e.g., equilibrium dissociation constant). Methods for determining affinity are known in the art.

An antibody that shows the same or similar binding affinity and/or specificity as a reference antibody refers to an antibody that is capable of having at least more than 50%, 60%, 70%, 80%, 90%, or 95% of the binding affinity and/or specificity of the reference antibody. This can be determined by any method known in the art for determining binding affinity and/or specificity. "Complementarity determining region" or "CDR region" or "CDR" is a region in an antibody variable domain that is highly variable in sequence and forms a structurally defined loop ("hypervariable loop") and/or comprises antigen-contacting residues ("antigen contact site"). CDRs are primarily responsible for binding to antigen epitopes. The CDRs of heavy and light chains are generally referred to as CDR1, CDR2, and CDR3, which are numbered sequentially from N-terminus. The CDRs located in a heavy chain variable domain of an antibody are referred to as HCDR1, HCDR2, and HCDR3, whereas the CDRs located in a light chain variable domain of an antibody are referred to as LCDR1, LCDR2, and LCDR3. In a given amino acid sequence of a light chain variable region or a heavy chain variable region, the exact amino acid sequence boundary of each CDR can be determined using any one or a combination of many well-known antibody CDR assignment systems including, e.g., Chothia based on the three-dimensional structure of antibodies and the topology of the CDR loops (Chothia et al. (1989) *Nature* 342:877-883; Al-Lazikani et al., *Standard conformations for the canonical structures of immunoglobulins, Journal of Molecular Biology,* 273:927-948 (1997)), Kabat based on antibody sequence variability (Kabat et al., *Sequences of Proteins of Immunological Interest,* 4th edition, U.S. Department of Health and Human Services, National Institutes of Health (1987)), AbM (University of Bath), Contact (11275/009037-360154.1126 (University College London), International ImMunoGeneTics database (IMGT) (imgt.cines.fr/on the World Wide Web), and North CDR definition based on the affinity propagation clustering using a large number of crystal structures.

However, it should be noted that boundaries of CDRs of variable regions of an antibody based on different assignment systems may differ. That is, CDR sequences of variable regions of an antibody defined by different assignment systems differ. Therefore, when it comes to defining an antibody with specific CDR sequences defined in the present invention, the scope of antibody also encompasses such antibodies whose variable region sequences comprise the specific CDR sequences, but having claimed CDR boundaries different from the specific CDR boundaries defined by the present invention due to a different protocol (e.g., different assignment system rules or their combinations) applied.

Antibodies with different specificities (i.e., different binding sites for different antigens) have different CDRs. However, although CDRs differ from antibody to antibody, only a limited number of amino acid positions within the CDRs are directly involved in antigen binding. The smallest overlapping region can be determined using at least two of the Kabat, Chothia, AbM, Contact, and North methods, thereby providing a "minimal binding unit" for antigen binding. The minimal binding unit may be a sub-portion of the CDR. As will be clear to those skilled in the art, residues of the rest CDR sequences can be determined via antibody structure and protein folding. Therefore, any variants of the CDRs given herein are also considered in the present invention. For example, in a CDR variant, the amino acid residues in the minimal binding unit may remain unchanged, while the other CDR residues defined by Kabat or Chothia may be substituted by conservative amino acid residues.

"Functional Fc region" possesses the "effector functions" of Fc regions of native sequences. Exemplary "effector functions" include C1q binding, CDC, Fc receptor binding, ADCC, phagocytosis, cell surface receptor (e.g., B cell receptor, or BCR) down-regulation, and the like. Such effector functions generally require that the Fc region is associated with a binding domain (e.g., an antibody variable domain) and can be assessed using a variety of assays, such as those disclosed herein.

The term "Fc region" is used herein to define a C-terminus region of an immunoglobulin heavy chain, which comprises at least one portion of a constant region. The term includes Fc regions of native sequences and variant Fc regions. In certain embodiments, a human IgG heavy chain Fc region extends from Cys226 or Pro230 to the carbonyl end of the heavy chain. However, the C-terminal lysine (Lys447) of the Fc region may or may not be present. Unless otherwise stated, the numbering of amino acid residues in the Fc region or constant region is based on an EU numbering system, which is also called EU index as described in Kabat et al., *Sequences of Proteins of Immunological Interest,* $5^{th}$ Ed. Public Health Service, National Institutes of Health, Bethesda, MD, 1991.

"Antibodies and antigen-binding fragments thereof" applicable to the present invention include but are not limited to polyclonal, monoclonal, monovalent, bispecific, isoconjugate, multispecific, recombinant, heterogenous, heterogenous hybrid, chimeric, humanized (particularly CDR-grafted), deimmunized or human antibodies, Fab fragments, Fab' fragments, $F(ab')_2$ fragments, fragments produced by an Fab expression library, Fd, Fv, disulphide-linked Fv (dsFv), single-chain antibodies (such as scFv), diabodies or tetrabodies (Holliger P. et al. (1993) *Proc. Natl. Acad. Sci. U.S.A.* 90 (14), 6444-6448), nanobodies (also referred to as single-domain antibodies), anti-idiotype (anti-Id) antibodies (including, for example, anti-Id antibodies against the antibody disclosed herein), and an epitope-binding fragment of any of the above.

"Human consensus framework" refers to a framework which represents the most common amino acid residues in the selection of human immunoglobulin VL or VH framework sequences. Generally, the selection of human immunoglobulin VL or VH sequences is a selection from subtypes of variable domain sequences.

"Antibody in IgG form" refers to the heavy chain constant region of the antibody belonging to the IgG form. Heavy chain constant regions of all antibodies of the same type are identical, and heavy chain constant regions of antibodies of different types are different. For example, an antibody in the form of IgG1 refers to the Ig domain of its heavy chain constant region being an Ig domain of an IgG1.

The term "therapeutic agent" described herein encompasses any substance that is effective in preventing or treating cholesterol-related diseases, including cytotoxic agents, other antibodies, small molecule drugs, or immunomodulatory agents, etc.

"Human antibody" refers to an antibody having an amino acid sequence which corresponds to the amino acid sequence of an antibody generated by a human or human cell or derived from a non-human source that utilizes human antibody libraries or other human antibody encoding sequences. This definition of a human antibody explicitly excludes humanized antibodies comprising non-human antigen-binding residues.

"Humanized" antibody refers to a chimeric antibody comprising amino acid residues from non-human CDRs and amino acid residues from human FRs. In some embodiments, a humanized antibody will comprise substantially all of at least one, typically two variable domains, wherein all or substantially all CDRs correspond to those of a non-human antibody, and all or substantially all FRs correspond to those of a human antibody. A humanized antibody may optionally comprise at least a portion of an antibody constant region derived from a human antibody. The "humanized form" of an antibody (such as a non-human antibody) refers to an antibody that has been humanized.

"Individual" or "subject" includes mammals. The mammals include, but are not limited to, domestic animals (e.g., cattle, goats, cats, dogs, and horses), primates (e.g., human and non-human primates such as monkeys), rabbits, and rodents (e.g., mice and rats). In some embodiments, the individual or subject is a human.

An "isolated" antibody is an antibody which has been separated from components of its natural environment. In some embodiments, the antibody is purified to a purity greater than 95% or 99% as determined by, e.g., electrophoresis (e.g., SDS-PAGE, isoelectric focusing (IEF) and capillary electrophoresis) or chromatography (e.g., ion exchange or reverse-phase HPLC). For a review of methods for assessing antibody purity, see, for example, Flatman et al., *J. Chromatogr.*, B848: 79-87 (2007).

The "percent (%) amino acid sequence identity" relative to a reference polypeptide sequence is defined as the percentage of amino acid residues in a candidate sequence that are identical to those in a reference polypeptide sequence after aligning the sequences (with gaps introduced if necessary) to achieve maximum percent sequence identity without considering any conservative replacement as part of sequence identity. Various methods in the art can be employed to perform sequence alignment so as to determine the percent amino acid sequence identity, for example, using computer software available to the public, such as BLAST, BLAST-2, ALIGN, or MEGALIGN (DNASTAR) software. Those skilled in the art can determine suitable parameters for measuring alignment, including any algorithm required to obtain maximum alignment for the full length of the aligned sequences.

Additionally or alternatively, the nucleic acid sequences and protein sequences described herein can be further used as "query sequences" to perform searches against public databases to, e.g., identify other family member sequences or related sequences.

The term "combination product" refers to a kit with a fixed combination, a non-fixed combination, or a part for combined administration in the form of a dose unit, wherein two or more therapeutic agents can be independently administered simultaneously or separately administered at intervals of time, especially when these intervals allow combination partners to exhibit collaboration, such as synergistic effect. The term "fixed combination" means that the antibody disclosed herein and a combination partner (e.g., other therapeutic agents, such as statin drugs) are simultaneously administered to a patient in the form of a single entity or dose. The term "non-fixed combination" means that the antibody disclosed herein and a combination partner (e.g., other therapeutic agents, such as statins) are simultaneously, concurrently, or sequentially administered to a patient as separate entities, without specific time limitation, wherein such administration provides therapeutically effective levels of the two compounds in the patient. The latter is also applicable to a cocktail therapy, e.g., administration of three or more therapeutic agents. In one preferred embodiment, the drug combination is a non-fixed combination.

The term "combination therapy" means that two or more therapeutic agents are administered to treat cholesterol-related diseases as described herein. Such administration includes co-administration of these therapeutic agents in a substantially simultaneous manner, for example, in a single capsule with a fixed proportion of active ingredients. Alternatively, such administration includes co-administration of each active ingredient in a variety of or separate containers (such as tablets, capsules, powder and liquid). The powder and/or liquid can be reconstituted or diluted to a desired dosage before administration. In addition, such administration also includes using each type of therapeutic agents in a sequential manner at approximately the same time or at different times. In any case, the therapeutic regimen will provide the beneficial effect of the drug combination in the treatment of disorders or symptoms described herein.

As used herein, "treatment" (or "treat" or "treating") refers to slowing, interrupting, arresting, alleviating, stopping, reducing, or reversing the progression or severity of an existing symptom, disorder, condition, or disease.

As used herein, "prevention" (or "prevent" or "preventing") includes the inhibition of the onset or progression of a disease or disorder or a symptom of a specific disease or disorder. In some embodiments, subjects with family histories are candidates for prophylactic regimens. Generally, the term "prevention" (or "prevent" or "preventing") refers to the administration of a drug prior to the onset of disorders or symptoms, particularly in subjects at risk.

The term "cholesterol-related disease" includes any one or more of the following: hypercholesterolemia, hyperlipidaemia, heart disease, metabolic syndrome, diabetes mellitus, coronary heart disease, stroke, cardiovascular diseases, Alzheimers disease, and general dyslipidemia (shown as, for example, increased total serum cholesterol, increased LDL, increased triglyceride, increased VLDL, and/or low HDL). Some non-limiting examples of primary and secondary dyslipidemias that can be treated with an anti-PCSK9 antibody (alone or in combination with one or more other drugs) include metabolic syndrome, diabetes mellitus, familial combined hyperlipidemia, familial hypertriglyceridemia, familial hypercholesterolemias, including heterozygous hypercholesterolemia, homozygous hypercholesterolemia, and familial defective apolipoprotein B-100; polygenic hypercholesterolemia; remnant removal disease; hepatic lipase deficiency; dyslipidemia secondary to any of the following: dietary indiscretion, hypothyroidism, drugs (including estrogen and progesterone therapies, β blockers and thiazide diuretics); nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia.

The term "hypercholesterolemia" used herein refers to a disorder in which the cholesterol level rises to above a certain level. In some embodiments, the LDL-cholesterol level rises to above a certain level. In some embodiments, the serum LDL-cholesterol level rises to above a certain level.

The term "vector" used herein refers to a nucleic acid molecule capable of proliferating another nucleic acid to which it is linked. The term includes vectors that serve as self-replicating nucleic acid structures as well as vectors binding to the genome of a host cell into which they have been introduced. Some vectors are capable of directing the expression of a nucleic acid to which they are operably linked. Such vectors are called "expression vectors" herein.

"Subject/patient sample" refers to a collection of cells or fluids obtained from a patient or a subject. The source of tissue or cell samples can be solid tissues, e.g., from fresh, frozen and/or preserved organ or tissue samples or biopsy samples or puncture samples; blood or any blood component; body fluids such as cerebrospinal fluids, amniotic fluids, peritoneal fluids, or interstitial fluids; and cells from a subject at any time during pregnancy or development. Tissue samples may comprise compounds which are naturally not mixed with tissues, such as preservatives, anticoagulants, buffers, fixatives, nutrients, antibiotics, and the like.

The term "effective amount" refers to an amount or a dosage of the preparation, antibody, or fragment described herein which generates an expected effect in a treated patient after the administration of a single or multiple doses. The effective amount can be easily determined by an attending physician as a person skilled in the art by considering a variety of factors as follows: species such as mammals; its size, age, and general health condition; the specific disease involved; the extent or severity of the disease; response in an individual patient; specific antibody administered; route of administration; bioavailability characteristics of the administered preparation; selected dosage regimen; and use of any concomitant therapy.

The "therapeutically effective amount" refers to an amount effective to achieve a desired therapeutic result at a necessary dosage for a necessary period of time. The therapeutically effective amount of the preparation, antibody or antibody fragment described herein, or conjugate or composition thereof can vary depending on a variety of factors such as disease state, age, sex and weight of an individual, and the ability of the antibody or antibody portion to elicit a desired response in the individual. The therapeutically effective amount is also such an amount in which any toxic or undesired effect of the preparation, antibody or antibody fragment or conjugate or composition thereof is inferior to the therapeutically beneficial effect.

The "prophylactically effective amount" refers to an amount effective to achieve a desired prophylactic result at a necessary dosage for a necessary period of time. Generally, since a prophylactic dose is administered in a subject before or at an earlier stage of a disease, a prophylactically effective amount will be less than a therapeutically effective amount.

The terms "host cell", "host cell line" and "host cell culture" are used interchangeably and refer to cells into which exogenous nucleic acids are introduced, including progenies of such cells. Host cells include "transformants" and "transformed cells", which include primary transformed cells and progenies derived therefrom, regardless of the number of passages. A generation may not be completely identical in nucleic acid content to the parent cell, but may contain mutations. Mutant generations having the same function or bioactivity that are screened or selected from the initially transformed cells are included herein.

As used herein, the term "preparation" refers to a composition which is suitably administered to animals, preferably mammals (including humans) and comprises at least one active ingredient and at least one non-active ingredient. "Liquid preparation" refers to a preparation in the form of liquid. The liquid preparation disclosed herein comprises (i) an anti-PCSK9 antibody or a fragment thereof; (ii) a buffer; (iii) a viscosity inhibitor; (iv) a surfactant; and (v) a solvent. The composition of the preparation disclosed herein may be as shown in the aforementioned liquid preparation embodiments. The liquid preparation disclosed herein is preferably an injection, more preferably a subcutaneous injection.

As used herein, the "buffer" refers to a pH buffer. Preferably, the buffer can keep pH of the liquid preparation disclosed herein at about 5.0 to 6.0, preferably about 5.2 to 5.8, more preferably about 5.4 to 5.6, and most preferably about 5.5. The concentration of the buffer in the liquid preparation is, for example, about 0.01 mg/mL to 50 mg/mL, about 0.1 mg/mL to 50 mg/mL, about 0.2 mg/mL to 10 mg/mL, about 0.5 mg/mL to 2.5 mg/mL, about 1.0 mg/mL to 2.0 mg/mL, or about 1.5 mg/mL. Preferably, the buffer is selected from histidine, glutamate, phosphate, acetate, citrate and tris(hydroxymethyl)aminomethane.

As used herein, the "viscosity inhibitor" refers to a substance that can reduce the viscosity of the liquid preparation comprising an anti-PCSK9 antibody. The concentration of the viscosity inhibitor in the liquid preparation is, for example, about 10 mmol/L to 1000 mmol/L, about 20 mmol/L to 500 mmol/L, about 50 mmol/L to 300 mmol/L, or about 50 mmol/L to 200 mmol/L. Preferably, the viscosity inhibitor is selected from sugar alcohol, arginine, arginine hydrochloride, sodium thiocyanate, ammonium thiocyanate, ammonium sulfate, ammonium chloride, calcium chloride, zinc chloride, sodium acetate, and combinations thereof. More preferably, the viscosity inhibitor is sorbitol or a combination of sorbitol and arginine or arginine salt (preferably arginine hydrochloride). Preferably, the concentration of sorbitol in the liquid preparation is about 1% to 6% (w/v); and the concentration of arginine or arginine salt (preferably arginine hydrochloride) in the liquid preparation is about 50 mmol/L to 180 mmol/L, preferably about 70 mmol/L to 150 mmol/L, and more preferably about 90 mmol/L.

As described herein, the "surfactant" refers to a substance which can significantly change the interface state of a solution system after being added in a small amount. The concentration of the surfactant in the liquid preparation is, for example, about 0.01 mg/mL to 5 mg/mL, about 0.05 mg/mL to 1 mg/mL, or about 0.1 mg/mL to 0.5 mg/mL, and more preferably about 0.3 mg/mL. Preferably, the surfactant is a nonionic surfactant, such as Pluronics® (poloxamers), polysorbate-80, polysorbate-60, polysorbate-40, or polysorbate-20.

As used herein, the term "solvent" refers to a liquid that is used to dissolve or suspend active ingredients and non-active ingredients to form a liquid preparation. Solvents that can be used in the present invention include, but are not limited to, water for injection, organic solvents for injection (including but not limited to oil for injection, ethanol, and propylene glycol), and combinations thereof.

As used herein, the term "sugar alcohol" refers to a corresponding polyol which is obtained by reduction reaction, such as catalytic hydrogenation, of monosaccharide. Sugar alcohols include, but are not limited to, sorbitol, mannitol, erythritol, maltitol, lactitol, xylitol, etc.

The term "about" used in combination with a numerical value is intended to encompass the numerical values in a range from a lower limit less than the specified numerical value by 10% to an upper limit greater than the specified numerical value by 10%.

As used herein, "w/v" refers to "weight/volume", for example, "1% w/v" means 1 g/100 mL=0.01 g/mL=10 mg/mL.

DETAILED DESCRIPTION

The present invention will be further illustrated below with reference to examples, and the following examples should not be construed as limiting the present invention.

Abbreviations:

SEC-HPLC: size exclusion chromatography-high performance liquid chromatography

CE-SDS: capillary electrophoresis-sodium dodecyl sulfate

CZE: capillary zone electrophoresis

Example 1. Determination of Parent Antibody by Screening of Anti-PCSK9 Antibodies Antigen Biotin Label According to the instructions of the manufacturer, PCSK9 antigen (SEQ ID NO: 53) was labeled with biotin using the sulfosuccinimidylbiotin labeling kit from Pierce. The FITC-labeled goat anti-human immunoglobulin F(ab') kappa chain antibody (LC-FITC) was purchased from Southern Biotech, polyethylene avidin (SA-PE) was purchased from Sigma, and streptavidin-633 (SA-633) was purchased from Molecular Probes. Streptomycin microbeads and a cellular immunomagnetic bead separation column were purchased from Miltenyi LS.

Preliminary Screening

Eight synthetic yeast-based antibody presentation libraries (from Adimab) were amplified according to an existing method (Xu, et al., 2013; WO 2009036379; WO 2010105256; WO 2012009568), with the diversity of each library reaching $1\times10^9$. Briefly, the first two rounds of screening employed magnetic-activated cell sorting using the MACS system available from Miltenyi. First, yeast cells (approximately $1\times10^{10}$ cells/library) from each library were incubated in FACS buffer (phosphate buffer, containing 0.1% bovine serum albumin) for 15 min at room temperature, and the buffer contained 100 nM biotin-labeled PCSK9 antigen as prepared above. The cells were washed once with 50 mL of pre-cooled FACS buffer and resuspended in 40 mL of the same buffer, followed by addition of 500 μL of streptomycin microbeads and incubation at 4° C. for 15 min. The mixture was centrifuged at 1000 rpm for 5 min. After discarding the supernatant, the cells were resuspended in 5 mL of FACS buffer. The resulting cell suspension was loaded on a Miltenyi LS column. After loading, the column was washed three times with FACS buffer, 3 mL each time. The Miltenyi LS column was removed from the magnetic field and eluted with 5 mL of growth medium. The eluted yeast cells were collected and incubated overnight at 37° C.

The next round of sorting was performed using a flow cytometer, wherein approximately $1\times10^8$ yeast cells screened by the MACS system were washed three times with FACS buffer and cultured in PCSK9 antigens or PCSK9-Fc fusion antigens labeled by a low concentration of biotin (100-1 nM) at room temperature. The culture media were discarded. After the cells were washed twice with FACS buffer, the cells were mixed with LC-FITC (1:100 dilution) and SA-633 (1:500 dilution) or EA-PE (1:50 dilution) and cultured at 4° C. for 15 min. The cells were washed twice with pre-cooled FACS buffer, resuspended in 0.4 mL of buffer and transferred into a separator tube with a filter. The cells were sorted using FACS ARIA (BD Biosciences).

Several rounds of screening were then performed to give competitive ligands and remove nonspecific conjugates (such as the membrane protein of CHO cells). After the last several rounds of sorting, the collected yeast cells were plated and cultured at 37° C. overnight, and target monoclonal antibodies were picked out. Sanger sequencing was employed to sequence variable regions of the obtained antibodies. About 310 antibodies with unique variable region sequences were obtained and identified one by one.

These anti-PCSK9 antibody proteins were obtained by yeast expression and protein A affinity chromatography purification.

Production and Purification of Antibodies

The yeast cells expressing the anti-PCSK9 antibodies obtained by screening were induced by shaking at 30° C. for 48 h to express the anti-PCSK9 antibodies. After the induction, the yeast cells were centrifuged at 1300 rpm for 10 min, and the supernatant was collected. The anti-PCSK9 antibodies in the supernatant were purified with Protein A and eluted with acetic acid buffer at pH 2.0, and the anti-PCSK9 antibodies were harvested. The antibodies were digested with papain and purified with KappaSelect (GE Healthcare) to produce corresponding Fab fragments.

According to a conventional method in the art, a gene DNA encoding the anti-PCSK9 antibodies was obtained from the aforementioned yeast cells expressing the anti-PCSK9 antibodies and, based on the conventional method, the gene DNA was cloned to a new expression vector (pCDNA3.1).

The aforementioned expression vector containing a target antibody gene and a transfection reagent Lipofectamine TM2000 (purchased from Invitrogen) was transiently transfected into cultured human embryonic kidney cells 293 according to a scheme provided by the manufacturer. The medium was discarded, and the cells were diluted to $4\times10^6$/mL with fresh medium. The cells were cultured at 37° C., 5% $CO_2$ for 7 days, with fresh medium fed every 48 h. After 7 days, the cells were centrifuged at 13000 rpm for 20 min. The supernatant was purified with Protein A to achieve an antibody purity of greater than 95%.

ForteBio KD Assay (Bio-Layer Interferometry)

The ForteBio affinity assay was performed according to the prior art (Estep, P, et al., High throughput solution based measurement of antibody-antigen affinity and epitope binning. MAbs, 2013.5 (2): p. 270-8). Briefly, a sensor was equilibrated offline in assay buffer for 30 min, and was equilibrated online for 60 s to establish a baseline. The purified antibody obtained as described above was loaded on line onto an AHQ sensor. The sensor was then exposed to 100 nM PCSK9 antigens for 5 min, before transferring the sensor to the assay buffer for dissociation for 5 min. The kinetic analysis was performed using a 1:1 binding model.

MSD-SET Kinetic Assay

The assay of equilibrium affinity is as described above (Estep, et al., 2013). The biotin-labeled PCSK9 antigen (b-PCSK9) with a final concentration of 10-100 μM obtained above was added to phosphate-buffered saline (PBSF) containing 0.1% IgG-free BSA, and the anti-PCSK9 Fab or mAb obtained above was serially diluted 3 to 5 folds to give an Fab or mAb solution with a concentration of 5-100 nM. The antibodies (diluted in 20 nM phosphate-buffered saline) were coated on a MSD-ECL plate at 4° C. overnight or at room temperature for 30 min. 3% BSA was added, and the antibodies were immobilized at 700 rpm for 30 min at room temperature, and were then washed 3 times with a washing buffer (PBSF+0.05% Tween 20). The samples were added to the plate, incubated at 700 rpm in a shaker at room temperature for 150 s and then washed once. The plate was added with 250 ng/mL sulfotag-labeled streptomycin (diluted in PBSF) and incubated at room temperature for 3 min. After washing the plate 3 times with the buffer, antigens binding on the plate were identified using MSD Sector Imager 2400. The percentage of unbinding antigens was obtained by the antibody titration method, and it was discovered that the binding of the anti-PCSK9 Fab or mAb to the antigens follows a quadratic equation of pharmacokinetics.

Identification of Epitope Binding by Octet Red384

The identification of epitope binding adopted a standard sandwich interactive blocking analysis method. A target-specific control IgG was fixed on an AHQ sensor, and an irrelevant human IgG1 antibody was used to occupy an empty Fc-binding site on the sensor. The sensor was immersed in 100 nM target antigen PCSK9 solution for 120 s, and was then put into a second 100 nM anti-PCSK9 antibody or ligand solution prepared as above. Data were read and processed by ForteBio data analysis software 7.0 (ForteBio). If the antigen could be bound by a second antibody or ligand after being bound by an antibody, it was suggested that there was an unbound epitope (non-competitive), otherwise epitope blocking (competitive or ligand blocking) was indicated. Through the aforementioned screening and identification, some antibodies that can block the binding of PCSK9 to LDLR and bind to both human and murine PCSK9 were obtained. To obtain an anti-PCSK9 antibody with higher affinity, the antibody ADI-02396 was optimized by the following method.

Example 2. Optimization of Affinity of Anti-PCSK9 Antibody

VHmut Screening

This method was to introduce mutations into antibody heavy chain regions by the conventional mismatched PCR method. In the PCR process, the probability of base pair mismatch was increased to about 0.01 bp by adding 1 μM highly mutated base analogs dPTP and 8-oxo-dGTP.

The resulting mismatched PCR product was constructed into a vector containing a heavy chain constant region by homologous recombination. By this method, a secondary pool with the capacity of $1\times10^7$ was obtained under screening pressure including PCSK9 antigen titer, unlabeled antigen competition, and competition with the parent antibody. Three rounds of screening were successfully performed by FACS.

CDRH1/CDRH2 Screening

CDRH3 genes of progeny antibodies obtained by VHmut were constructed into a CDRH1/CDRH2 gene pool with the diversity of $1\times10^8$, and 3 rounds of screening were carried out for the genes. The first round of screening adopted MACS, while the second and third rounds adopted FACS. Antibody-antigen conjugates were subjected to pressurized screening for screening out antibodies with the highest affinity.

The first round of optimization: The first step was to increase the affinity of the anti-PCSK9 antibody ADI-02396 (named "parent" antibody) with human-murine cross-activity and ligand competition. In short, mutations were introduced into the parent antibody (by employing the "mismatched PCR" method) to establish a secondary yeast-based antibody presentation library. Finally, a secondary library with a size of about $1\times10^7$ was generated for the subsequent enriching of antibodies with higher affinity. Screening pressure included PCSK9 antigen titer, unlabeled antigen competition, and competition with the parent antibody. The FACS technique was also used to screen a target population (see Chao, et al., *Nature Protocols,* 2006). After 2 to 3 rounds of enriching, the obtained yeasts were plated to give monoclonal antibodies. After this, 3 progenies with improved affinity, ADI-09111, ADI-09112 and ADI-09113, were obtained. Assayed by ForteBio Octet, the $K_D$ ranges of the three antibodies were 1 nM to 10 nM. The two progeny antibodies ADI-09112 and ADI-09113 were used in the second round of affinity optimization.

The second round of affinity optimization: The second step was to improve the affinity of the two anti-PCSK9 monoclonal antibodies ADI-09112 and ADI-09113 (named "parent" antibody) with human-murine cross-activity and ligand competition. In short, a secondary yeast-based antibody presentation library was established again for each parent antibody. The CDR-H3 and light chains (LC) of the parent antibodies were combined with CDR-H1 and CDR-H2 of genes in an existing yeast library (named "H1/H2" optimization). Finally, 5 libraries with a size of about $1\times10^8$ were generated for the subsequent enriching of antibodies with higher affinity. The screening method was the same as that in the first round of screening. After 2 to 3 rounds of enriching, the yeasts were plated to give monoclonal antibodies. After this, progeny antibodies with improved affinity were obtained, among which ADI-10085, ADI-10086 and ADI-10087 were variants of CDR-H1 and CDR-H2 regions of ADI-09912, and ADI-10088, ADI-10089 and ADI-10090 were variants of VH regions of ADI-09113. The related sequence information of the antibodies is shown in Tables A-C. The affinity of these antibodies for human PCSK9 was increased by 10 times, and the $K_D$ ranges were between 4-17 μM and 200 μM (Table 1 and Table 2), as detected by the ForteBio method and MSD-SET assay. The affinity of part of the antibodies was about ten times higher than that of control antibodies. The identification of other antibody functions can further reduce the number of antibodies so as to facilitate preclinical development.

The sequence information and number of each anti-PCSK9 antibody involved herein are shown in Tables A-C below:

TABLE A

Sequence number of each CDR of exemplary antibodies disclosed herein

| IgG ADI name | Heavy chain CDR SEQ ID NO | | | Light chain CDR SEQ ID NO | | |
|---|---|---|---|---|---|---|
| | CDR1 | CDR2 | CDR3 | CDR1 | CDR2 | CDR3 |
| ADI-02396 | 1 | 2 | 3 | 4 | 5 | 6 |
| ADI-09111 | 1 | 2 | 18 | 4 | 5 | 6 |
| ADI-09112 | 1 | 14 | 19 | 4 | 5 | 6 |
| ADI-09113 | 7 | 15 | 18 | 4 | 5 | 6 |
| ADI-10085 | 8 | 16 | 19 | 4 | 5 | 6 |
| ADI-10086 | 9 | 17 | 19 | 4 | 5 | 6 |
| ADI-10087 | 10 | 17 | 19 | 4 | 5 | 6 |
| ADI-10088 | 11 | 17 | 18 | 4 | 5 | 6 |
| ADI-10089 | 12 | 17 | 18 | 4 | 5 | 6 |
| ADI-10090 | 13 | 17 | 18 | 4 | 5 | 6 |

TABLE B

Sequence number of each framework region of heavy chain variable regions and light chain variable regions of exemplary antibodies disclosed herein

| IgG ADI | Framework region of heavy chain variable region SEQ ID NO | | | | Framework region of light chain variable region SEQ ID NO | | | |
|---|---|---|---|---|---|---|---|---|
| name | FR1 | FR2 | FR3 | FR4 | FR1 | FR2 | FR3 | FR4 |
| ADI-02396 | 45 | 46 | 47 | 48 | 49 | 50 | 51 | 52 |
| ADI-09111 | 45 | 46 | 47 | 48 | 49 | 50 | 51 | 52 |
| ADI-09112 | 45 | 46 | 47 | 48 | 49 | 50 | 51 | 52 |
| ADI-09113 | 45 | 46 | 47 | 48 | 49 | 50 | 51 | 52 |
| ADI-10085 | 45 | 46 | 47 | 48 | 49 | 50 | 51 | 52 |
| ADI-10086 | 45 | 46 | 47 | 48 | 49 | 50 | 51 | 52 |
| ADI-10087 | 45 | 46 | 47 | 48 | 49 | 50 | 51 | 52 |
| ADI-10088 | 45 | 46 | 47 | 48 | 49 | 50 | 51 | 52 |
| ADI-10089 | 45 | 46 | 47 | 48 | 49 | 50 | 51 | 52 |
| ADI-10090 | 45 | 46 | 47 | 48 | 49 | 50 | 51 | 52 |

TABLE C

Sequence numbers of heavy chain variable regions, light chain variable regions, heavy chain and light chain sequences of exemplary antibodies disclosed herein

| IgG ADI name | Heavy chain variable region SEQ ID NO | Heavy chain SEQ ID NO | Light chain variable region SEQ ID NO | Light Chain SEQ ID NO |
|---|---|---|---|---|
| ADI-02396 | 23 | 34 | 24 | 35 |
| ADI-09111 | 25 | 36 | 24 | 35 |
| ADI-09112 | 26 | 37 | 24 | 35 |
| ADI-09113 | 27 | 38 | 24 | 35 |
| ADI-10085 | 28 | 39 | 24 | 35 |
| ADI-10086 | 29 | 40 | 24 | 35 |
| ADI-10087 | 30 | 41 | 24 | 35 |
| ADI-10088 | 31 | 42 | 24 | 35 |
| ADI-10089 | 32 | 43 | 24 | 35 |
| ADI-10090 | 33 | 44 | 24 | 35 |

TABLE 1

| KD of antibodies measured by ForteBio method | | | |
|---|---|---|---|
| | ForteBio: IgG $K_D$ (M), IgG was fixed on a probe | | |
| Sample ID | Human PCSK-9 | Cynomolgus monkey PCSK-9 | Murine PCSK-9 |
| ADI-02396 | 9.50E−09 | 3.23E−08 | 7.83 E−08 |
| ADI-09111 | 1.17E−09 | 2.61E−09 | 1.05 E−08 |
| ADI-09112 | 4.97E−10 | 9.83E−10 | 3.78E−09 |
| ADI-09113 | 8.04E−10 | 1.12E−09 | 3.10E−09 |
| ADI-10085 | 2.95E−10 | 3.77E−10 | 5.44E−10 |
| ADI-10086 | 3.36E−10 | 4.57E−10 | 6.07E−10 |
| ADI-10087 | 2.96E−10 | 3.96E−10 | 5.58E−10 |
| ADI-10088 | 4.71E−10 | 6.32E−10 | 8.55E−10 |
| ADI-10089 | 3.11E−10 | 4.08E−10 | 5.89E−10 |
| ADI-10090 | 3.52E−10 | 4.69E−10 | 6.74E−10 |
| Alirocumab | 3.01E−11 | 3.83E−10 | 2.66E−09 |
| Evolocumab | 1.03E−09 | 1.30E−09 | 1.14E−07 |
| Bococizumab | 3.86E−10 | 4.76E−10 | 6.63E−10 |
| Lodelcizumab | 1.51E−09 | 2.34E−09 | NB |

TABLE 2

| $K_D$ of antibodies measured kinetically by MSD-SET | | | | |
|---|---|---|---|---|
| | MSD: Fab $K_D$ (M), IgG was fixed on an assay plate | | | |
| Sample ID | Human PCSK-9 (pH 7.4) | Human PCSK-9 (pH 6.0) | Cynomolgus monkey PCSK-9 (pH 7.4) | Murine PCSK-9 (pH 7.4) |
| ADI-02396 | ND | ND | 5.90E−09 | ND |
| ADI-09111 | 7.00E−10 | 1.90 E−9 | 1.20E−09 | 3.50 E−09 |
| ADI-09112 | 2.20E−10 | 4.90E−10 | 3.00E−10 | 1.20E−09 |
| ADI-09113 | 1.70E−10 | 6.50 E−10 | 2.40E−10 | 7.60E−10 |
| ADI-10085 | 4.20E−12 | 5.90E−12 | 1.20E−11 | 4.10E−11 |
| ADI-10086 | 8.60E−12 | 1.30 E−11 | 2.40E−11 | 6.00E−11 |
| ADI-10087 | 5.00E−12 | 9.80E−12 | 1.30E−11 | 4.10E−11 |
| ADI-10088 | 1.00E−11 | 1.60E−11 | 2.20E−11 | 8.70E−11 |
| ADI-10089 | 1.10E−11 | 1.00E−11 | 2.20E−11 | 7.00E−11 |
| ADI-10090 | 1.70E−11 | 2.10 E−11 | 3.80E−11 | 1.20E−10 |
| Alirocumab | 7.20E−11 | 5.10E−11 | 8.20E−11 | 3.00E−10 |
| Evolocumab | 1.60E−11 | ND | 8.20E−12 | ND |
| Bococizumab | 2.10E−11 | 3.80E−11 | 2.60E−11 | 6.50E−11 |
| Lodelcizumab | ND | ND | 1.00E−10 | NB |

Example 3. Experiment on Inhibition of the Binding of PCSK-9 to LDLR by Anti-PCSK9 Antibodies The PCSK9 protein (biotin-labeled PCSK9 protein) described in example 1 was diluted to 400 nmol/L with PBS solution (phosphate-buffered saline solution) to serve as a working solution. The anti-PCSK9 antibodies (ADI-10085, ADI-10086, ADI-10087, ADI-10088, ADI-10089 and ADI-10090) obtained in example 2 were diluted with PBS solution to concentrations of 1000 nmol/L, 100 nmol/L, 10 nmol/L, 1 nmol/L and 0. 1 nmol/L, respectively, and according to the same method, solutions of control antibodies (Alirocumab, Evolocumab, Bococizumab and Lodelcizumab) at each concentration were prepared. The PCSK9 working solution was mixed with an equal volume of each gradiently diluted anti-PCSK9 antibody sample or control sample. CHO cells (CHO-LDLR) overexpressing human LDLR were resuspended in PBS solution and counted. The cell concentration was adjusted to $4\times10^6$ cells/mL with PBS solution. The CHO cells were inoculated into a U-bottom 96-well plate, with 50 μL of cell medium added in each well. 50 μL of a mixed solution of PCSK9 and each anti-PCSK9 antibody was added. Each well contains $2.0\times10^5$ cells. The mixture was centrifuged at 200 g at room temperature for 5 min, and the supernatant was discarded. Anti-His-FITC (R&D Systems) was diluted with PBS solution at a ratio of 1:200 to a final concentration of 2.5 μg/mL, added to a 96-well plate, at 100 μL per well, and put in an ice bath for 30 min. Centrifugation was performed at 200 g at room temperature for 5 min, the supernatant was gently discarded, and 150 μL of PBS solution was added into each well; then centrifugation was performed at 200 g at room temperature for 5 min, and the supernatant was gently discarded. This operation was repeated 3 times. PBS solution was added to each well at 80 μL/well, and the cells were pipetted for several times with a pipette for resuspension. The fluorescence signal value of cells was detected by a flow cytometer.

For the fluorescence signals detected in the experiment, see Table 3 below.

TABLE 3

| Fluorescence signal value | | | | | |
|---|---|---|---|---|---|
| Sample name | 1000 nM | 100 nM | 10 nM | 1 nM | 0.1 nM |
| ADI-10085 | 5700.0 | 5087.0 | 5684.0 | 8914.0 | 10431.0 |
| ADI-10086 | 5269.0 | 5129.0 | 5830.0 | 6919.0 | 6600.0 |
| ADI-10087 | 5094.0 | 5259.0 | 5743.0 | 6483.5 | 6865.0 |
| ADI-10088 | 5216.0 | 5162.0 | 5826.0 | 6827.0 | 6798.0 |
| ADI-10089 | 5331.0 | 5137.0 | 5635.0 | 6500.0 | 6889.5 |
| ADI-10090 | 4822.0 | 4806.0 | 5807.0 | 6750.0 | 6807.0 |
| ADI-02396 | 5993.0 | 5067.0 | 5513.0 | 6375.0 | 6646.0 |
| IgG | 8919.0 | 7523.0 | 6955.0 | 6728.5 | 6998.5 |
| Alirocumab | 4926.0 | 4952.0 | 5748.0 | 6985.0 | 7174.5 |
| Evolocumab | 4805.0 | 5097.0 | 5780.0 | 6807.0 | 6986.0 |
| Bococizumab | 6038.0 | 5307.0 | 6267.5 | 6959.0 | 7096.0 |
| Lodelcizumab | 7330.0 | 8756.0 | 7330.5 | 8756.0 | 8405.0 |
| +PCSK9 | 9977.0 | N/A | N/A | N/A | N/A |
| −PSCK9 | 3985.0 | N/A | N/A | N/A | N/A |
| Blank control | 3782.0 | N/A | N/A | N/A | N/A |

The raw data in Table 3 were analyzed and plotted using GraphPad Prism6, obtaining FIG. 1. According to the results, the anti-PCSK9 antibodies have a capability of blocking the binding of PCSK9 to LDLR equivalent to that of the control antibodies.

Example 4. Analytical Experiment on Uptake of LDL-C by Cells

A HepG2 cell cryopreservation tube was taken out of a liquid nitrogen storage tank and rapidly thawed at 37° C. under a water bath. The cell suspension was transferred into a 15 mL centrifuge tube, and 4 mL of room-temperature growth medium (90% DMEM+10% FBS, both purchased from Gibco) was slowly added. After 5 min of centrifugation at 1000 r/min at room temperature, the deposited cells were resuspended in fresh growth medium, transferred into a culture flask, and cultured at 37° C., 5% $CO_2$. HepG2 cells in the log phase were washed twice with PBS solution and then digested for 3 min with 1 mL of 0.25% trypsin (purchased from Gibco), and the cells were resuspended in 6 mL of growth medium to quench the reaction. After the cell concentration was adjusted to $0.8\times10^6$ cells/mL with the growth medium, the HepG2 cells were inoculated into a black clear-bottom 96-well plate coated with poly-D-lysine (purchased from Nunc) at 100 μL/well, and incubated in an incubator at 37° C., 5% $CO_2$ for 6 to 7 h. The growth medium was discarded and replaced by assay medium (DMEM+5% FBS) at 100 μL/well, and the HepG2 cells were cultured in an incubator at 37° C., 5% $CO_2$ overnight. The antibody samples (ADI-10085, ADI-10087, ADI-10088 and ADI-10089) were diluted to 66.7 nmol/L with the assay medium. With 66.7 nmol/L as the initial concentration, 4-fold gradient dilution was performed in the same manner for both the positive control antibodies (Alirocumab, Evolocumab and Lodelcizumab) and the negative control antibodies (LDL, PCSK9+LDL and IgG). 60 μL of each obtained concentration-gradient sample was mixed with an equal volume (60 μL) of 66.7 nmol/L PCSK9, thus obtaining each mixture. The blank control was 120 μL of assay medium. The liquid in the 96-well plate was pipetted out, and 50 μL of the mixture and blank control was added into each well and incubated in an incubator at 37° C., 5% $CO_2$ for 1 h. The culture plate was taken out, added with 6 μg/mL BODIPY-labeled LDL solution (purchased from life technologies) diluted with the assay medium at 50 μL/well, and cultured at 37° C., 5% $CO_2$ for 4 h. The medium was discarded, and 100 μL of PBS solution was added to each well to wash the plate and then discarded. After washing twice, each well was added with 100 μL of PBS solution. The fluorescence values were read using a Spectra Max 13 microplate reader.

Figure 2:
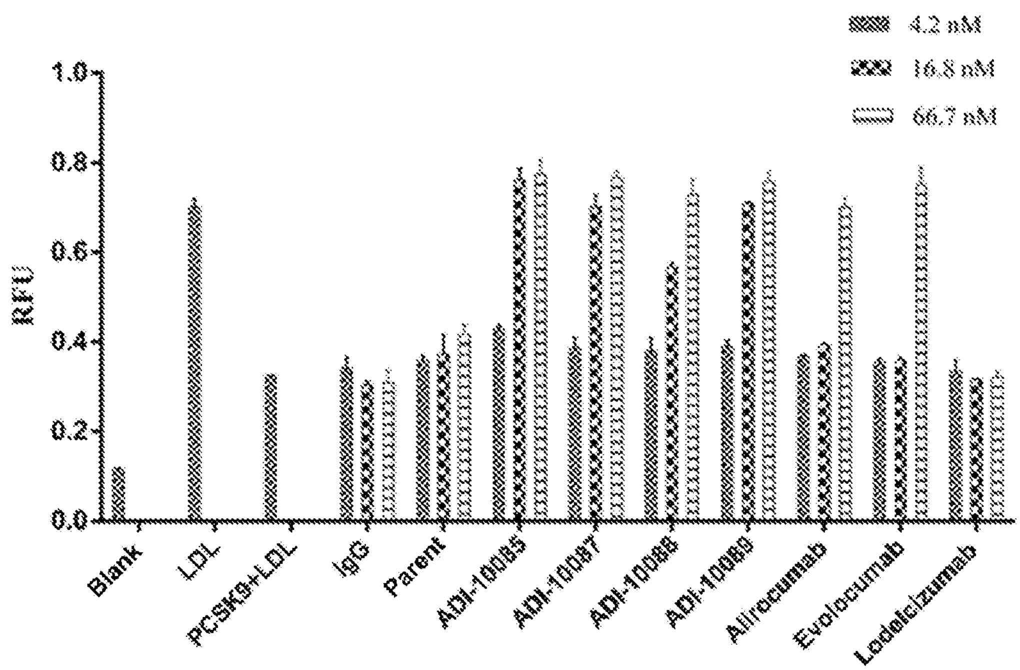
FIG. 2 shows the capability of anti-PCSK9 antibodies at different concentrations in enhancing the restoration of LDLR in HepG2 cells.

The obtained raw fluorescence data are listed in Table 4 below, which were analyzed and plotted using GraphPad Prism6, thus obtaining FIG. 2. It can be seen from the results that the fluorescence values obtained in the case where HepG2 cells were treated with anti-PCSK9 antibodies (ADI-10085, ADI-10087, ADI-10088, and ADI-10089) were enhanced by about two times compared with the fluorescence values obtained in the absence of the anti-PCSK9 antibodies. These data prove that each anti-PCSK9 antibody disclosed herein can enhance the capability of restoring LDLR in HepG2 cells and inhibit the decrease of LDL-C uptake induced by PCSK9, resulting in increased LDL-C uptake in HepG2 cells, which is superior to the positive control antibodies at gradients of 16.8 nM and 66.7 nM.

TABLE 4

| | Fluorescence signal value | | | | | |
|---|---|---|---|---|---|---|
| Sample name | 4.2 nM | | 16.8 nM | | 66.7 nM | |
| Blank control | 0.1179 | 0.1174 | N/A | N/A | N/A | N/A |
| LDL | 0.7139 | 0.6903 | N/A | N/A | N/A | N/A |
| PCSK9 + LDL | 0.3251 | 0.3259 | N/A | N/A | N/A | N/A |
| IgG | 0.3583 | 0.3250 | 0.2973 | 0.3093 | 0.3288 | 0.2881 |
| ADI-02396 | 0.3662 | 0.3522 | 0.4035 | 0.3410 | 0.4319 | 0.4006 |
| ADI-10085 | 0.4228 | 0.4349 | 0.7800 | 0.7423 | 0.7492 | 0.7973 |
| ADI-10087 | 0.3701 | 0.4030 | 0.7198 | 0.6835 | 0.7576 | 0.7755 |
| ADI-10088 | 0.3570 | 0.4005 | 0.5736 | 0.5611 | 0.7059 | 0.7522 |
| ADI-10089 | 0.3803 | 0.3986 | 0.7116 | 0.7064 | 0.7742 | 0.7413 |
| Alirocumab | 0.3636 | 0.3704 | 0.3958 | 0.3919 | 0.6865 | 0.7158 |
| Evolocumab | 0.3506 | 0.3598 | 0.3555 | 0.3630 | 0.7239 | 0.7785 |
| Lodelcizumab | 0.3181 | 0.3523 | 0.3173 | 0.3141 | 0.3296 | 0.3124 |

Example 5. Analytical Experiment on Internalization of LDLR into Cells

PCSK9 can directly bind to LDLR to promote the internalization of LDLR which is transported to lysosomes for degradation after entering hepatocytes, thus reducing LDLR expressed on the surface of cells and increasing the level of LDL-C in serum. Anti-PCSK9 antibodies can block the binding of PCSK9 to LDLR, thus reducing the ability of PCSK9 to consume LDLR. In this experiment, the bioactivity of anti-PCSK9 antibodies against the internalization of LDLR into cells was determined by co-incubating CHO-LDLR cells with the anti-PCSK9 antibodies and a PCSK9 protein solution, detecting the fluorescence values of LDLR with the aforementioned flow cytometer, and comparing the fluorescence values of the anti-PCSK9 antibodies and the positive control antibody (Evolocumab).

Figure 3:
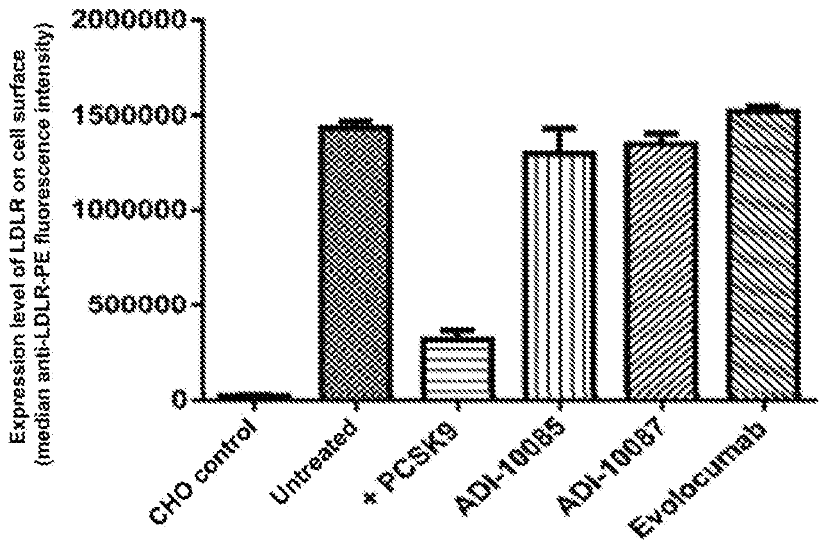
FIG. 3 shows the capability of anti-PCSK9 antibodies at different concentrations in reducing the internalization of LDLR into cells.

RPMI 1640 cell medium (Gibco) was used to prepare the PCSK9 protein described in example 1 into a concentration of 50 μg/mL. 60 μL of 1000 nm anti-PCSK9 antibodies (ADI-10085 and ADI-10087) were uniformly mixed with a solution of PCSK9 (50 g/mL) and then the mixture was incubated for 30 min. The positive control antibody was treated in the same way. CHO cells and CHO-LDLR cells were separately centrifuged at 500 g at room temperature for 3 min. The cells were resuspended in PBS solution with the cell density adjusted to $2\times10^6$ cells/mL. The cell suspensions were added to U-bottom 96-well plates at 100 μL/well. The aforementioned mixed sample was added to the plate at 100 μL/well in quadruplicate, pipetted uniformly, and incubated at 4° C. for 4 h. The mixture was washed 3 times with 200 μL of PBS solution, and centrifuged at 500 g at room temperature for 3 min. 5 μL of anti-LDLR-PE (Sino Biological, Item No. 20131-R301-P) was diluted with 100 μL of PBS solution, and then added to a U-bottom 96-well plate at 100 μL/well and incubated away from light for 30 min. The mixture was washed 3 times with 200 μL of PBS solution, and centrifuged at 500 g for 3 min. The obtained cells were resuspended in cell medium, and the fluorescence signal of the PE fluorescence-labeled LDLR protein on the surface of the CHO-LDLR cells was detected using a flow cytometer. The results are shown in Table 5. The raw data in Table 5 were analyzed and plotted using GraphPad Prism6, obtaining FIG. 3.

It can be seen from the results in Table 5 that the antibodies obtained herein effectively block the internalization of LDLR in cells.

TABLE 5

| | Fluorescence signal value | | | | |
|---|---|---|---|---|---|
| Sample name | 1 | 2 | 3 | 4 | Average |
| CHO control | 26308.5 | 14666.5 | N/A | N/A | 20487.5 |
| Untreated | 1461967 | 1413043 | N/A | N/A | 1437505 |
| + PCSK9 | 267181 | 284270.5 | 353893 | 362791 | 317033.9 |
| ADI-10085 | 1148583 | 1232906 | 1465201 | 1339541 | 1296558 |
| ADI-10087 | 1432592 | 1332187 | 1339160 | 1300079 | 1351005 |
| Evolocumab | 1560702 | 1524849 | 1507073 | 1500379 | 1523251 |

Example 6. Hypolipidemic Effect of Anti-PCSK9 Antibody on Healthy SD Rats

The tested antibody (anti-PCSK9 antibody ADI-10087) was administered to SPF SD rats (Vital River) according to a conventional method in the art, wherein the female rats were about 254 g to 294 g in weight and about 9 to 12 weeks old, and the male rats were about 369 g to 420 g in weight and about 9 to 12 weeks old. The tested antibody was administered to each group once. The dosage regimen is shown in Table 6.

TABLE 6

| Dosage design and administration | | | | | |
|---|---|---|---|---|---|
| Group No. | Group | Dose (mg/kg) | Concentration (mg/mL) | Administration capacity (mL/kg) | Number of animals |
| 1 | Anti-PCSK9 antibody low dose group, single SC administration | 3 | 0.75 | 4 | 6, half female and half male |
| 2 | Anti-PCSK9 antibody medium dose group, single SC administration | 10 | 2.5 | 4 | 6, half female and half male |
| 3 | Anti-PCSK9 antibody high dose group, single SC administration | 30 | 7.5 | 4 | 6, half female and half male |
| 4 | Anti-PCSK9 antibody group, single IV administration | 10 | 2.5 | 4 | 6, half female and half male |
| 5 | Evolocumab control group, single SC administration | 10 | 2.5 | 4 | 6, half female and half male |

Figure 6:
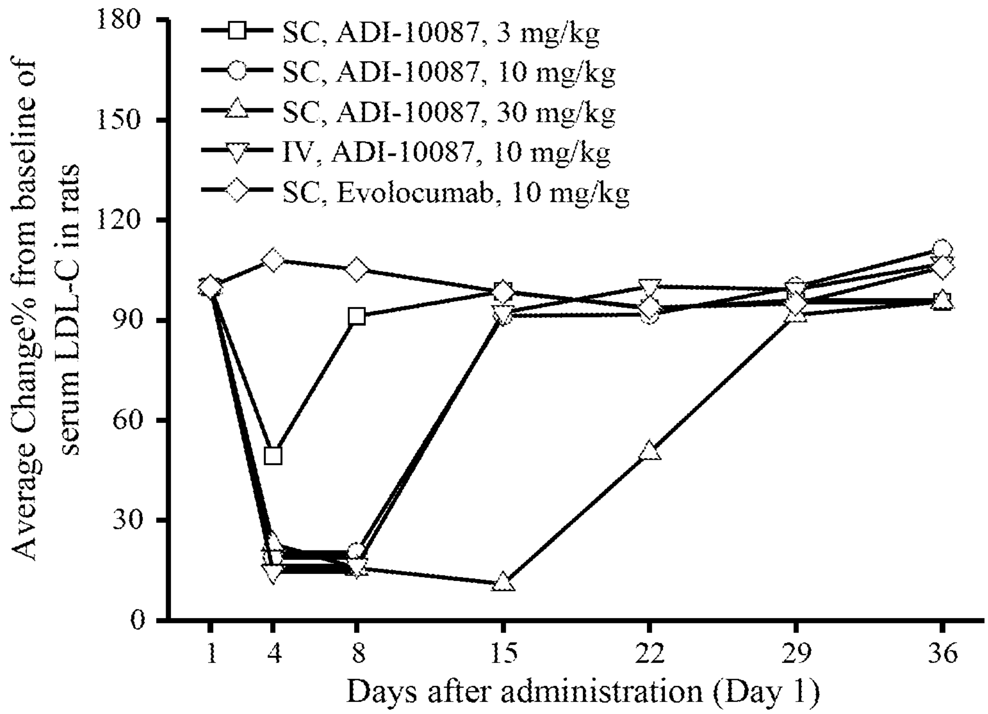
FIG. 6 shows a graph of the % change rate (average) of LDL-C in serum relative to a pre-administration level (before D1 administration, baseline) after subcutaneous or intravenous administration of an anti-PCSK9 antibody or Evolocumab to rats plotted against time.
Figure 7:
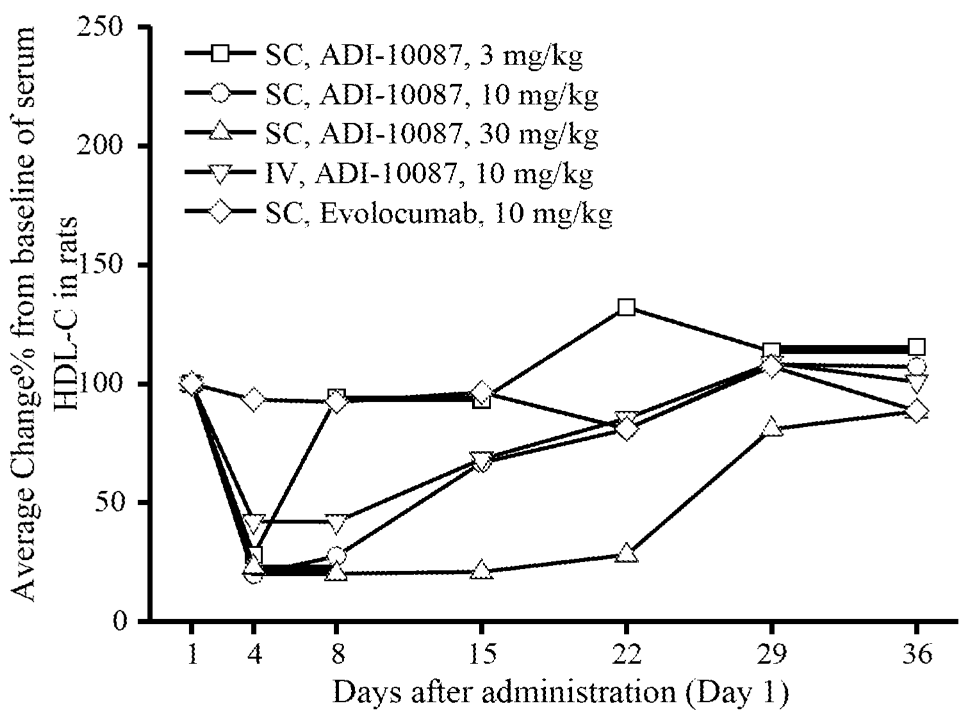
FIG. 7 shows a graph of the % change rate (average) of % HDL-C in serum relative to a pre-administration level (before D1 administration, baseline) after subcutaneous or intravenous administration of the anti-PCSK9 antibody or Evolocumab to rats plotted against time.

The blood of each group of animals was collected via the jugular vein according to a conventional method at the following time points: 0 h before administration (D1) and 72 h (D4), 168 h (D8), 336 h (D15), 504 h (D22), 672 h (D29), and 840 h (D36) after administration. The blood samples were collected into anticoagulant-free tubes, coagulated on ice and then centrifuged at 2-8° C. at 5000 rpm/min for 10 min, and serum was collected and assayed for LDL-C and HDL-C using a Hitachi-7060 automatic biochemical analyzer. According to the data of blood lipid analysis, the change rate of LDL-C and HDL-C (% LDL-C and % HDL-C) relative to those before administration (baselines) at each time point were calculated. According to the results, it was found that after 3-30 mg/kg of the anti-PCSK9 antibody disclosed herein was subcutaneously administered to the rats once, the LDL-C and HDL-C levels in serum decreased dose-dependently (FIG. 6 and FIG. 7). For example, 3 days, 7 days, 14 days and 21 days after administration, the LDL-C and HDL-C levels significantly decreased in comparison with the baseline levels. In addition, it was also found that after 10 mg/kg of Evolocumab was subcutaneously administered to the rats once, the LDL-C and HDL-C levels in serum did not significantly decrease.

For other antibodies disclosed herein, the same method can also be applied for the above assay.

Example 7. Hypolipidemic Effect of Anti-PCSK9 Antibody on Healthy Cynomolgus Monkeys The tested antibody (anti-PCSK9 antibody ADI-10087) was administered to cynomolgus monkeys (Guangdong Blooming-Spring Biological Technology Development Co., Ltd.) according to a conventional method in the art, wherein the female animals were about 2 kg to 4 kg in weight and about 3 to 5 years old, and the male animals were about 3 kg to 5 kg in weight and about 3 to 5 years old. The dosage regimen is shown in Table 7, wherein the tested antibody was administered to groups 1-5 once and group 6 once a week, 4 times in total.

TABLE 7

| Dosage design and administration | | | | | |
|---|---|---|---|---|---|
| Group No. | Group | Dose (mg/kg) | Concentration (mg/mL) | Administration capacity (mL/kg) | Number of animals |
| 1 | Anti-PCSK9 antibody low dose group, single SC administration | 3 | 6 | 0.5 | 6, half female and half male |
| 2 | Anti-PCSK9 antibody medium dose group, single SC administration | 10 | 20 | 0.5 | 6, half female and half male |
| 3 | Anti-PCSK9 antibody high dose group, single SC administration | 30 | 60 | 0.5 | 6, half female and half male |
| 4 | Anti-PCSK9 antibody group, single IV administration | 10 | 1 | 10 | 6, half female and half male |
| 5 | Evolocumab control group, single SC administration | 10 | 20 | 0.5 | 6, half female and half male |
| 6 | Anti-PCSK9 antibody group, repeated SC administration | 10 | 20 | 0.5 | 6, half female and half male |

For groups 1-5, blood was collected from the subcutaneous vein or the inguinal femoral artery/inguinal vein in the contralateral forelimb or hind limb of the limb on which the drug was administered according to a conventional method at the following time points: 0 h before administration and 24 h (D2), 72 h (D4), 120 h (D6), 168 h (D8), 336 h (D15), 504 h (D22), 672 h (D29), 840 h (D36), 1008 h (D43), 1176 h (D50) and 1344 h (D57) after administration. With regard to group 6, blood was collected at the following time points according to the aforementioned method: 0 h before the first administration and 24 h (D2), 72 h (D4), 120 h (D6), 168 h (D8, before the second administration) and 336 h (D15, before the third administration) after administration. For the last administration, blood was collected 0 h before administration and 24 h (D2), 72 h (D4), 120 h (D6), 168 h (D8), 336 h (D15), 504 h (D22), 672 h (D29), 840 h (D36), 1008 h (D43), 1176 h (D50) and 1344 h (D57) after administration.

Figure 8:
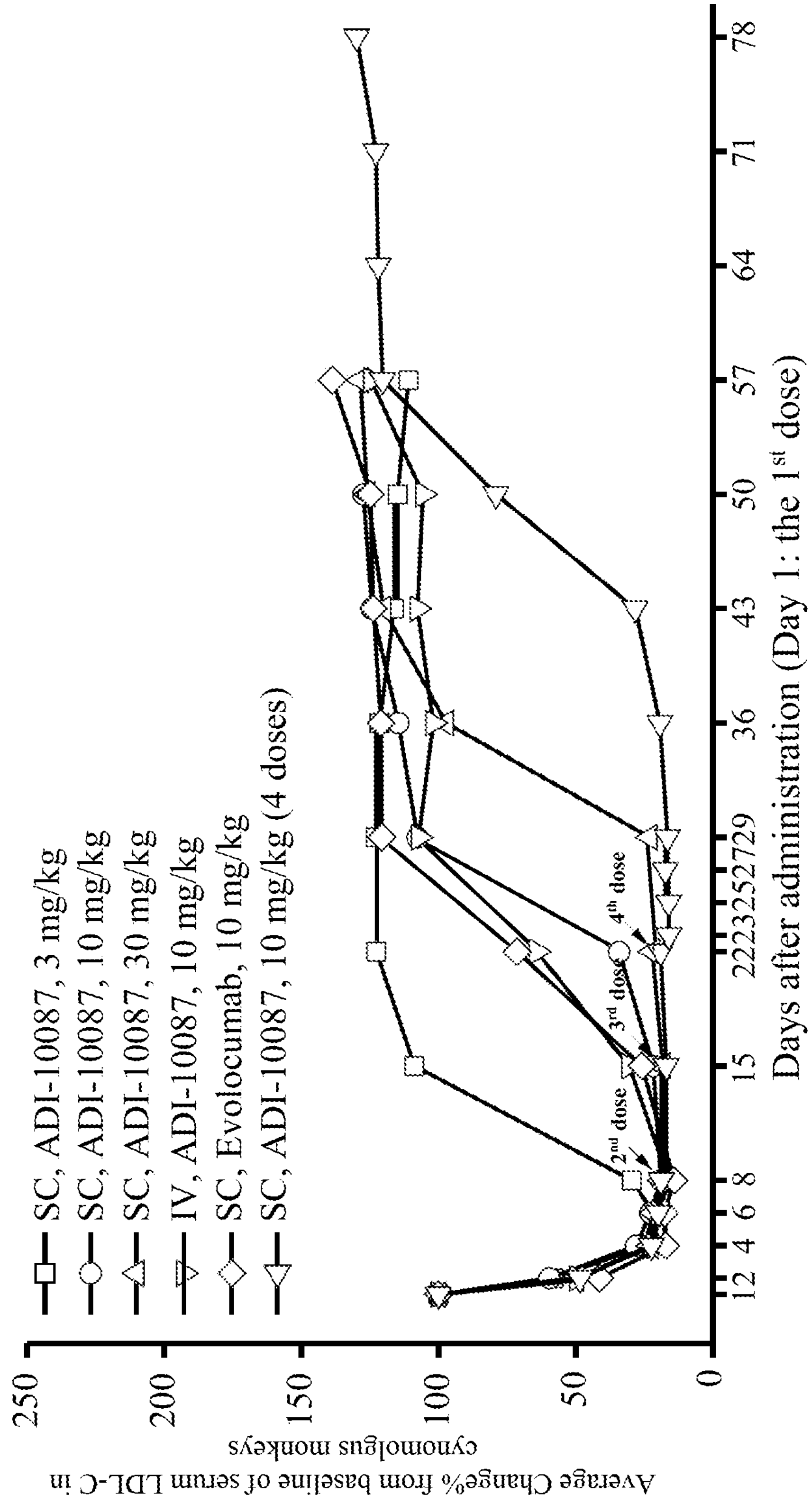
FIG. 8 shows a graph of the % change rate (average) of LDL-C in serum relative to a pre-administration level (before D1 administration, baseline) after administration of the anti-PCSK9 antibody or Evolocumab to cynomolgus monkeys plotted against time.
Figure 10:
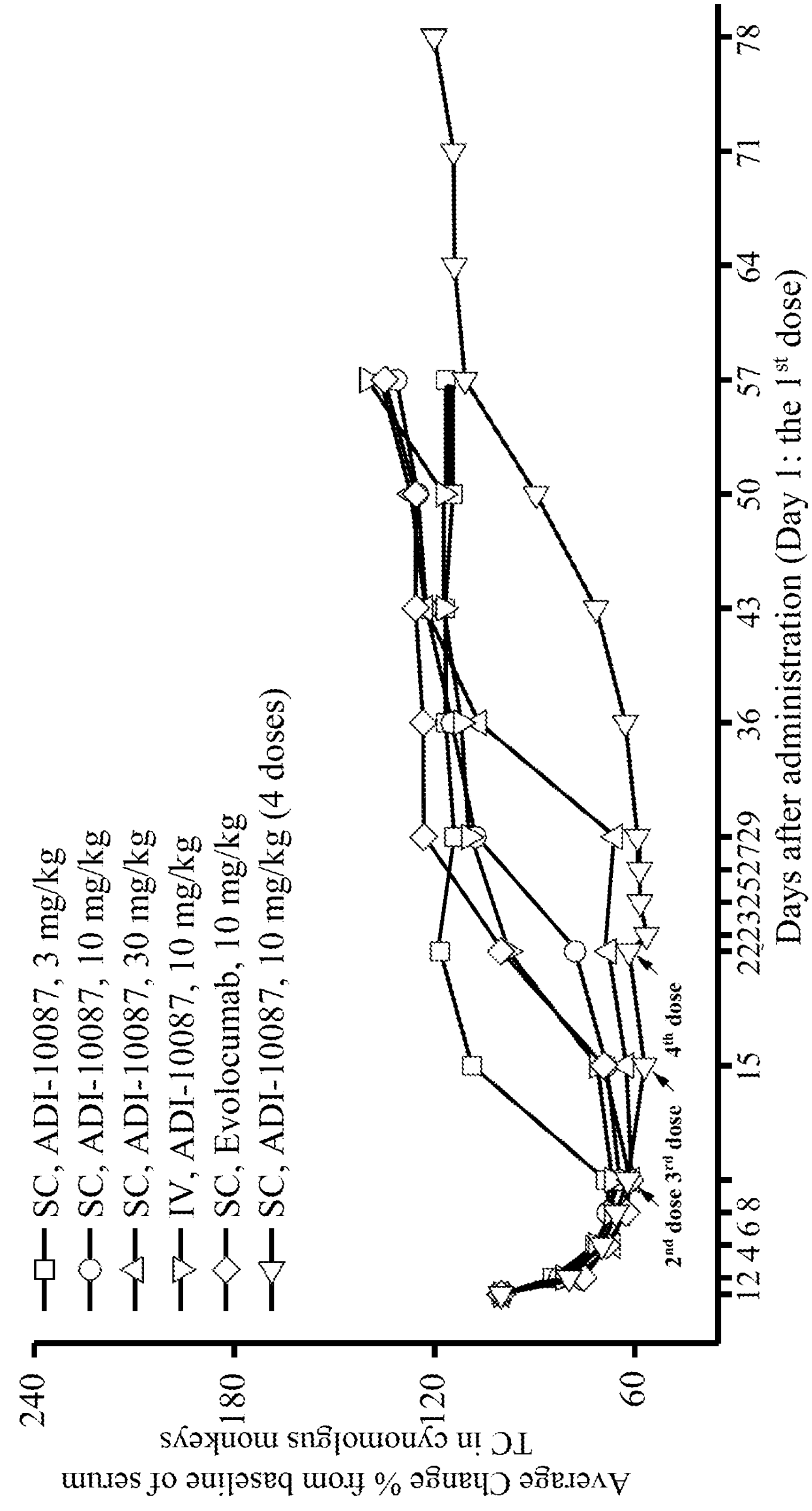
FIG. 10 shows a graph of the % change rate (average) of serum TC relative to a pre-administration level (before D1 administration, baseline) after administration of the anti-PCSK9 antibody or Evolocumab to cynomolgus monkeys plotted against time.

Whole blood was collected into tubes containing coagulant and separation gel, placed on ice for coagulation, and then centrifuged at 2-8° C. at 5000 rpm/min for 10 min, and serum was collected. After all blood samples were collected, total cholesterol (TC), LDL-C and HDL-C were assayed. According to the data of blood lipid analysis, the change rate of LDL-C and HDL-C (% LDL-C and % HDL-C) relative to those before administration (baselines) at each time point were calculated. According to the results, it was found that after a single subcutaneous administration of the anti-PCSK9 antibody (ADI-10087) disclosed herein to the cynomolgus monkeys at 3 mg/kg, 10 mg/kg and 30 mg/kg, both the LDL-C (FIG. 8) and TC (FIG. 10) levels in serum significantly decreased in an obvious dose-effect manner, and were significantly lower than the baseline levels 3 to 28 days after the administration. This indicates that the antibody disclosed herein can effectively alleviate conditions and/or disorders related to LDL-C and TC, such as lowering blood lipid level.

Figure 9:
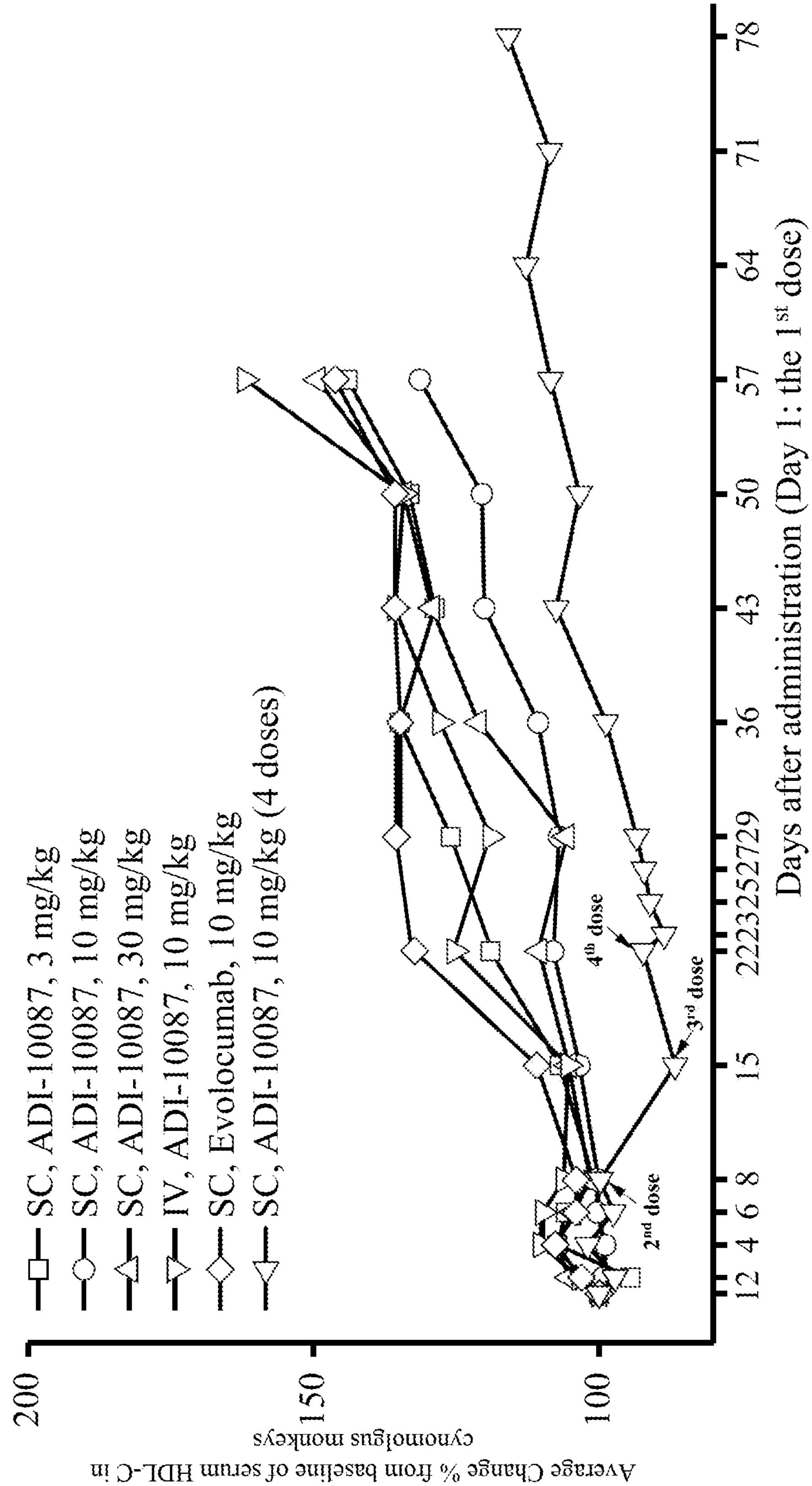
FIG. 9 shows a graph of the % change rate (average) of HDL-C in serum relative to a pre-administration level (before D1 administration, baseline) after administration of the anti-PCSK9 antibody or Evolocumab to cynomolgus monkeys plotted against time.

The administration of the anti-PCSK9 antibody had no significant influence on the HDL-C level in the serum of the cynomolgus monkeys on the whole (FIG. 9).

However, it was surprisingly found that after separate single subcutaneous administration of the anti-PCSK9 antibody disclosed herein and Evolocumab to the cynomolgus monkeys at 10 mg/kg, Evolocumab only significantly lowered LDL-C in comparison with the baseline level in 14 days after the administration, shorter than 21 days after the administration achieved by the same dose of the antibody disclosed herein. That is, the anti-PCSK9 antibody disclosed herein significantly lowered LDL-C for a longer period than Evolocumab.

For other antibodies disclosed herein, the same method can also be applied for the above assay.

Example 8. Preparation of the Liquid Preparation Comprising Anti-PCSK9 Antibody (Preparation A) Disclosed Herein A liquid preparation comprising an anti-PCSK9 antibody with a concentration of 150 mg/mL prepared according to formula A Formula A

- Anti-PCSK9 antibody 150 mg/mL (ADI-10087)
- Histidine 1.5 g/L
- Arginine 90 mmol/L
- Sorbitol 3%
- Polysorbate 80 0.3 g/L
- pH 5.5

The anti-PCSK9 antibody (ADI-10087) obtained in example 2 was added to an ultrafiltration centrifuge tube (molecular weight cutoff: 30 KD), after concentration by centrifugation, the anti-PCSK9 antibody was diluted with an aqueous solution of formula A without polysorbate 80 and the anti-PCSK9 antibody (1.5 g/L histidine, 90 mmol/L arginine, 3% sorbitol, pH 5.5) and then concentrated; and this operation was repeated until the replacement was completed. The concentration of the replaced protein was adjusted to 150 mg/mL. Then an aqueous solution of polysorbate 80 (30 g/L, 1/100 by volume) was added to adjust the final concentration of polysorbate 80 to 0.3 g/L. After being aseptically filtered, the semi-finished product was aliquoted into vials and the vials were then capped with rubber stoppers and aluminum-plastic caps, and the product was obtained.

Example 9. Preparation of Comparative Example (Preparation B) of the Liquid Preparation Comprising Anti-PCSK9 Antibody Disclosed Herein Comparative example: An preparation comprising anti-PCSK9 antibody liquid with a concentration of 150 mg/mL prepared according to formula B Formula B

- Anti-PCSK9 antibody 150 mg/mL (ADI-10087)
- Histidine 1.5 g/L
- Arginine 180 mmol/L
- Polysorbate 80 0.3 g/L
- pH 5.5

The anti-PCSK9 antibody (ADI-10087) obtained in example 2 was added to an ultrafiltration centrifuge tube (molecular weight cutoff: 30 KD), after concentration by centrifugation, the anti-PCSK9 antibody was diluted with an aqueous solution of formula B without polysorbate 80 and the anti-PCSK9 antibody (1.5 g/L histidine, 180 mmol/L arginine, pH 5.5) and then concentrated; and this operation was repeated until the replacement was completed. The concentration of the replaced protein was adjusted to 150 mg/mL. Then an aqueous solution of polysorbate 80 (30 g/L, 1/100 by volume) was added to adjust the final concentration of polysorbate 80 to 0.3 g/L. After being aseptically filtered, the semi-finished product was aliquoted into vials and the vials were then capped with rubber stoppers and aluminum-plastic caps, and the product was obtained.

Example 10. Measurement of Viscosity of the Liquid Preparation Comprising Anti-PCSK9 Antibody The viscosity was measured with a cone-and-plate viscometer (Brookfield, CAP1000+/2000+. For details, visit http://www.sinoinstrument.com/product_details-4-83-401-60.html) at room temperature of 20-25° C. A rotor and a rotational speed were selected (rotor: cp-40; rotational speed: 25 rpm). The rotor was connected to a connecting nut, with the position adjusted, and samples were added. The Run button was pushed to start the measurement of the viscosity of the samples. According to the above experiment, the viscosity of preparation A was 5.2 centipoises, and the viscosity of preparation B was 6.0 centipoises. Surprisingly, the viscosity of preparation A was significantly lower than that of preparation B, indicating that the combination of arginine and sorbitol is more beneficial to reduce the viscosity of a high-concentration antibody preparation.

Example 11. Change in Protein Purity of the Liquid Preparation Comprising Anti-PCSK9 Antibody In order to inspect the stability of preparation A and preparation B, an accelerated stability test was carried out. The product of preparation A and preparation B aliquoted in the plugged and capped vials were examined for accelerated stability at 40° C.±2° C./60% RH±5% RH for 2 months. Meanwhile, the change in protein purity was assayed by SEC-HPLC and non-reduced CE-SDS as follows.

SEC-HPLC:

The sample was diluted to a concentration of 2 mg/mL; a hydrophilic silica gel size exclusion chromatography column TSKG 3000 SW×1 was used; the amount of injected protein was 100 μg; the mobile phases were 20 mmol/L $Na_2HPO_4$•12 $H_2O$, 150 mmol/L NaCl, and 200 mmol/L arginine; the pH was 6.8; the flow velocity was 0.5 mL/min; the detection wavelength was 280 nm; the column temperature was 25° C.; and the area normalization method was used for calculation.

CE-SDS:

About 100 μg of sample was taken and added with a sample buffer (pH 7.0) to adjust the total volume to 95 μL. The reduced sample was added with 5 μL of β-mercaptoethanol, and the non-reduced sample was added with 5 μL of 250 mmol/L NEM. After mixing, the mixture was heated at 70° C. for 10 min and detected.

By SEC-HPLC, based on the percentage decrease of an SEC main peak, the changes in protein purity were assayed to be a decrease by 2.6% after 1 month and a decrease by 3.7% after 2 months for preparation A; and a decrease by 4.1% after 1 month and a decrease by 7.0% after 2 months for preparation B. Based on the percentage decrease of non-reduced CE-SDS, the changes in protein purity were assayed to be a decrease by 0.4% after 2 weeks and a decrease by 2.0% after 1 month for preparation A; and a decrease by 2.5% after 2 weeks and a decrease by 7.3% after 1 month for preparation B. It can be seen that the purity change rate of preparation A is significantly slower than that of preparation B. Relative to preparation B, preparation A has higher stability.

Example 12. Assay of Charge Heterogeneity of the Liquid Preparation Comprising Anti-PCSK9 Antibody At different time points, preparation A and preparation B which had undergone the accelerated stability test in example 11 were sampled for charge heterogeneity assay. Beckman uncoated capillaries and a Beckman PA800 plus capillary electrophoresis apparatus were adopted; the sampling voltage was 0.5 psi; the sampling time was 10.0 s; the separation voltage was 30 kV; and the analysis time was 30 min. The area normalization method was used to calculate the peak area of acidic components, basic components, and the main peak as a percentage of the total peak area. The CZE main peak of preparation A dropped by 0% after 2 weeks and by 2.9% after 1 month. The CZE main peak of preparation B dropped by 2.0% after 2 weeks and by 7.6% after 1 month. It can be seen that the charge heterogeneity change rate of preparation A is significantly slower than that of preparation B, thus the combination of arginine and sorbitol contributes to less charge heterogeneity change of the preparation.

The exemplary embodiments of the present invention have been described above. It should be understood by those skilled in the art that these contents are merely exemplary, and various other replacements, adaptations and modifications can be made within the scope of the present invention. Therefore, the present invention is not limited to the specific embodiments listed herein.

The invention claimed is:

1. A liquid antibody preparation, comprising:

(i) an anti-proprotein convertase subtilisin/kexin type 9 (anti-PCSK9) antibody or an antigen-binding fragment thereof;

(ii) a buffer, wherein the buffer is selected from the group consisting of histidine buffer, glutamate buffer, phosphate buffer, acetate buffer, citrate buffer, and tris (hydroxymethyl)aminomethane buffer;

(iii) a viscosity inhibitor, wherein the viscosity inhibitor is a combination of (a) sorbitol, and (b) arginine or an arginine salt; and (iv) a surfactant, wherein said anti-PCSK9 antibody or an antigen-binding fragment thereof comprises a heavy chain variable region (VH) and a light chain variable region (VL), wherein said VH comprises complementary determinant regions (CDRs) HCDR1, HCDR2 and HCDR3 and said VL comprises CDRs LCDR1, LCDR2 and LCDR3:

(a) HCDR1 comprising the amino acid sequence of SEQ ID NO: 20, HCDR2 comprising the amino acid sequence of SEQ ID NO: 21, and HCDR3 comprising the amino acid sequence of SEQ ID NO: 22; and LCDR1 comprising the amino acid sequence of SEQ ID NO: 4, LCDR2 comprising the amino acid sequence of SEQ ID NO: 5, and LCDR3 comprising the amino acid sequence of SEQ ID NO: 6;

(b) HCDR1 comprising the amino acid sequence of SEQ ID NO: 1, HCDR2 comprising the amino acid sequence of SEQ ID NO: 2, and HCDR3 comprising the amino acid sequence of SEQ ID NO: 3; and LCDR1 comprising the amino acid sequence of SEQ ID NO: 4, LCDR2 comprising the amino acid sequence of SEQ ID NO: 5, and LCDR3 comprising the amino acid sequence of SEQ ID NO: 6;

(c) HCDR1 comprising the amino acid sequence of SEQ ID NO: 1, HCDR2 comprising the amino acid sequence of SEQ ID NO: 2, and HCDR3 comprising the amino acid sequence of SEQ ID NO: 18; and LCDR1 comprising the amino acid sequence of SEQ ID NO: 4, LCDR2 comprising the amino acid sequence of SEQ ID NO: 5, and LCDR3 comprising the amino acid sequence of SEQ ID NO: 6;

(d) HCDR1 comprising the amino acid sequence of SEQ ID NO: 1, HCDR2 comprising the amino acid sequence of SEQ ID NO: 14, and HCDR3 comprising the amino acid sequence of SEQ ID NO: 19; and LCDR1 comprising the amino acid sequence of SEQ ID NO: 4, LCDR2 comprising the amino acid sequence of SEQ ID NO: 5, and LCDR3 comprising the amino acid sequence of SEQ ID NO: 6;

(e) HCDR1 comprising the amino acid sequence of SEQ ID NO: 7, HCDR2 comprising the amino acid sequence of SEQ ID NO: 15, and HCDR3 comprising the amino acid sequence of SEQ ID NO: 18; and LCDR1 comprising the amino acid sequence of SEQ ID NO: 4, LCDR2 comprising the amino acid sequence of SEQ ID NO: 5, and LCDR3 comprising the amino acid sequence of SEQ ID NO: 6;

(f) HCDR1 comprising the amino acid sequence of SEQ ID NO: 8, HCDR2 comprising the amino acid sequence of SEQ ID NO: 16, and HCDR3 comprising the amino acid sequence of SEQ ID NO: 19; and LCDR1 comprising the amino acid sequence of SEQ ID NO: 4, LCDR2 comprising the amino acid sequence of SEQ ID NO: 5, and LCDR3 comprising the amino acid sequence of SEQ ID NO: 6;

(g) HCDR1 comprising the amino acid sequence of SEQ ID NO: 9, HCDR2 comprising the amino acid sequence of SEQ ID NO: 17, and HCDR3 comprising the amino acid sequence of SEQ ID NO: 19; and LCDR1 comprising the amino acid sequence of SEQ ID NO: 4, LCDR2 comprising the amino acid sequence of SEQ ID NO: 5, and LCDR3 comprising the amino acid sequence of SEQ ID NO: 6;

(h) HCDR1 comprising the amino acid sequence of SEQ ID NO: 10, HCDR2 comprising the amino acid sequence of SEQ ID NO: 17, and HCDR3 comprising the amino acid sequence of SEQ ID NO: 19; and LCDR1 comprising the amino acid sequence of SEQ ID NO: 4, LCDR2 comprising the amino acid sequence of SEQ ID NO: 5, and LCDR3 comprising the amino acid sequence of SEQ ID NO: 6;

(i) HCDR1 comprising the amino acid sequence of SEQ ID NO: 11, HCDR2 comprising the amino acid sequence of SEQ ID NO: 17, and HCDR3 comprising the amino acid sequence of SEQ ID NO: 18; and LCDR1 comprising the amino acid sequence of SEQ ID NO: 4, LCDR2 comprising the amino acid sequence of SEQ ID NO: 5, and LCDR3 comprising the amino acid sequence of SEQ ID NO: 6;

(j) HCDR1 comprising the amino acid sequence of SEQ ID NO: 12, HCDR2 comprising the amino acid sequence of SEQ ID NO: 17, and HCDR3 comprising the amino acid sequence of SEQ ID NO: 18; and LCDR1 comprising the amino acid sequence of SEQ ID NO: 4, LCDR2 comprising the amino acid sequence of SEQ ID NO: 5, and LCDR3 comprising the amino acid sequence of SEQ ID NO: 6; or (k) HCDR1 comprising the amino acid sequence of SEQ ID NO: 13, HCDR2 comprising the amino acid sequence of SEQ ID NO: 17, and HCDR3 comprising the amino acid sequence of SEQ ID NO: 18; and LCDR1 comprising the amino acid sequence of SEQ ID NO: 4, LCDR2 comprising the amino acid sequence of SEQ ID NO: 5, and LCDR3 comprising the amino acid sequence of SEQ ID NO: 6;

wherein the concentration of the anti-PCSK9 antibody or the antigen-binding fragment thereof in the liquid antibody preparation is about 50 mg/mL to about 200 mg/ml;

wherein the concentration of the buffer in the liquid antibody preparation is about 0.1-50 mg/mL;

wherein the concentration of the sorbitol is about 1% to 6% (w/v), and the concentration of the arginine or arginine salt is about 50 mmol/L to 180 mmol/L;

wherein the concentration of the surfactant is about 0.01 mg/mL to 5 mg/ml; and wherein the pH of the liquid preparation is about 5.0 to 6.0.

2. The liquid antibody preparation according to claim 1, wherein the surfactant is a nonionic surfactant selected from the group consisting of poloxamers, polysorbate-80, polysorbate-60, polysorbate-40, and polysorbate-20.

3. The liquid antibody preparation according to claim 1, wherein the viscosity of the liquid preparation at 25° C. is about 1.0 to 20 centipoises.

4. The liquid antibody preparation according to claim 1, wherein the liquid preparation is a pharmaceutical preparation.

5. The liquid antibody preparation according to claim 1, wherein the anti-PCSK9 antibody or the antigen-binding fragment thereof comprises a heavy chain variable region (VH) and a light chain variable region (VL), (a) the heavy chain variable region VH comprising the amino acid sequence of SEQ ID NO: 23; and the light chain variable region VL comprising the amino acid sequence of SEQ ID NO: 24;

(b) the heavy chain variable region VH comprising the amino acid sequence of SEQ ID NO: 25; and the light chain variable region VL comprising the amino acid sequence of SEQ ID NO: 24;

(c) the heavy chain variable region VH comprising the amino acid sequence of SEQ ID NO: 26; and the light chain variable region VL comprising the amino acid sequence of SEQ ID NO: 24;

(d) the heavy chain variable region VH comprising the amino acid sequence of SEQ ID NO: 27; and the light chain variable region VL comprising the amino acid sequence of SEQ ID NO: 24;

(e) the heavy chain variable region VH comprising the amino acid sequence of SEQ ID NO: 28; and the light chain variable region VL comprising the amino acid sequence of SEQ ID NO: 24;

(f) the heavy chain variable region VH comprising the amino acid sequence of SEQ ID NO: 29; and the light chain variable region VL comprising the amino acid sequence of SEQ ID NO: 24;

(g) the heavy chain variable region VH comprising the amino acid sequence of SEQ ID NO: 30; and the light chain variable region VL comprising the amino acid sequence of SEQ ID NO: 24;

(h) the heavy chain variable region VH comprising the amino acid sequence of SEQ ID NO: 31; and the light chain variable region VL comprising the amino acid sequence of SEQ ID NO: 24;

(i) the heavy chain variable region VH comprising the amino acid sequence of SEQ ID NO: 32; and the light chain variable region VL comprising the amino acid sequence of SEQ ID NO: 24; or (j) the heavy chain variable region VH comprising the amino acid sequence of SEQ ID NO: 33; and the light chain variable region VL comprising the amino acid sequence of SEQ ID NO: 24.

6. The liquid antibody preparation according to claim 1, wherein the anti-PCSK9 antibody or the antigen-binding fragment thereof comprises a heavy chain and a light chain, (a) the heavy chain comprising the amino acid sequence of SEQ ID NO: 34; and the light chain comprising the amino acid sequence of SEQ ID NO:35;

(b) the heavy chain comprising the amino acid sequence of SEQ ID NO: 36; and the light chain comprising the amino acid sequence of SEQ ID NO:35;

(c) the heavy chain comprising the amino acid sequence of SEQ ID NO: 37; and the light chain comprising the amino acid sequence of SEQ ID NO:35;

(d) the heavy chain comprising the amino acid sequence of SEQ ID NO: 38; and the light chain comprising the amino acid sequence of SEQ ID NO:35;

(e) the heavy chain comprising the amino acid sequence of SEQ ID NO: 39; and the light chain comprising the amino acid sequence of SEQ ID NO:35;

(f) the heavy chain comprising the amino acid sequence of SEQ ID NO: 40; and the light chain comprising the amino acid sequence of SEQ ID NO:35;

(g) the heavy chain comprising the amino acid sequence of SEQ ID NO: 41; and the light chain comprising the amino acid sequence of SEQ ID NO:35;

(h) the heavy chain comprising the amino acid sequence of SEQ ID NO: 42; and the light chain comprising the amino acid sequence of SEQ ID NO:35;

(i) the heavy chain comprising the amino acid sequence of SEQ ID NO: 43; and the light chain comprising the amino acid sequence of SEQ ID NO:35; or (j) the heavy chain comprising the amino acid sequence of SEQ ID NO: 44; and the light chain comprising the amino acid sequence of SEQ ID NO:35.

7. A method for preparing the liquid antibody preparation of claim 1, the method comprising mixing a combination of sugar alcohol and arginine or arginine salt as a viscosity inhibitor with an anti-PCSK9 antibody.

8. A solid preparation, obtained by lyophilizing the liquid antibody preparation according to claim 1.

9. A method for lowering the cholesterol level in a subject, the method comprising administering to the subject the liquid antibody preparation according to claim 1.

10. A method for treating a cholesterol-related disease in a subject, the method comprising administering to the subject the liquid antibody preparation according to claim 1.

11. The liquid antibody preparation according to claim 1, wherein the concentration of the anti-PCSK9 antibody or the antigen-binding fragment thereof in the liquid antibody preparation is about 100 mg/mL to about 200 mg/mL.

12. The liquid antibody preparation according to claim 1, wherein the buffer is histidine buffer.

13. The liquid antibody preparation according to claim 1, wherein the arginine salt is arginine hydrochloride.

14. The liquid antibody preparation according to claim 1, wherein the concentration of the sorbitol is about 2% to 4% (w/v), and the concentration of the arginine or an arginine salt is about 70 mmol/L to 150 mmol/L.

15. The liquid antibody preparation according to claim 1, wherein the concentration of the sorbitol is about 3% (w/v), and the concentration of the arginine or an arginine salt is about 90 mmol/L.

16. The liquid antibody preparation according to claim 1, wherein the concentration of the surfactant is about 0.05 mg/mL to 1 mg/mL.

17. The liquid antibody preparation according to claim 2, wherein the nonionic surfactant is poloxamers.

18. The liquid antibody preparation according to claim 1, wherein the pH of the liquid preparation is about 5.2 to 5.8.

19. The liquid antibody preparation according to claim 1, wherein the viscosity of the liquid preparation at 25° C. is about 1.0 to 10 centipoises.

20. The liquid antibody preparation according to claim 4, wherein the liquid preparation is an injection.

21. The liquid antibody preparation according to claim 4, wherein the injection is a subcutaneous injection.

* * * * *

SEQUENCE LISTING

```
<160> NUMBER OF SEQ ID NOS: 53

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 1

Gly Ser Ile Ser Ser Ser Ser Tyr Tyr Trp Gly
1               5                   10


<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR2

<400> SEQUENCE: 2

Ser Ile Tyr Tyr Ser Gly Ser Thr Tyr Tyr Asn Pro Ser Leu Lys Ser
1               5                   10                  15


<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<223> OTHER INFORMATION: heavy chain variable region CDR3

<400> SEQUENCE: 3

Ala Arg Glu Gly Ser Gly Val Val Pro Ala Ala Gly Pro Asn Trp Phe
1 5 10 15

Asp Pro

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: light chain variable region CDR1

<400> SEQUENCE: 4

Arg Ala Ser Gln Ser Val Ser Ser Tyr Leu Ala
1 5 10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: light chain variable region CDR2

<400> SEQUENCE: 5

Asp Ala Ser Asn Arg Ala Thr
1 5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: light chain variable region CDR3

<400> SEQUENCE: 6

Gln Gln Arg Arg Asn Trp Phe Thr
1 5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: heavy chain variable region CDR1

<400> SEQUENCE: 7

Gly Ser Val Ser Ser Ser Ser Tyr Tyr Trp Gly
1 5 10

<210> SEQ ID NO 8
<211> LENGTH: 11
<212> TYPE: PRT
<213> ORGANISM: Artificial Sequence -continued

```
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 8

Gly Ser Ile Val Ser Ser Ser Tyr Tyr Trp Ala
1               5                   10


<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 9

Gly Ser Ile Arg Ser Ser Ala Tyr Tyr Trp Gly
1               5                   10


<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 10

Gly Ser Ile Ser Ser Ala Ser Tyr Tyr Trp Ser
1               5                   10


<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 11

Gly Ser Ile Gly Ser Ser Ser Tyr Tyr Trp Ala
1               5                   10


<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 12

Gly Ser Ile Gly Ser Ser Ser Tyr Tyr Trp Thr
1               5                   10


<210> SEQ ID NO 13
<211> LENGTH: 11
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 13

Gly Ser Ile Trp Ser Ser Ser Tyr Tyr Trp Thr
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR2

<400> SEQUENCE: 14

Ser Ile Tyr Tyr Ser Gly Ser Thr Tyr Tyr Asn Pro Phe Leu Lys Ser
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR2

<400> SEQUENCE: 15

Ser Ala Tyr Tyr Ser Gly Ser Thr Tyr Tyr Asn Pro Ser Leu Lys Ser
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR2

<400> SEQUENCE: 16

Ser Ile Asn Tyr Lys Gly Ser Thr Tyr Tyr Asn Pro Ser Leu Lys Ser
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR2

<400> SEQUENCE: 17

Ser Ile Asn Tyr Arg Gly Ser Thr Tyr Tyr Asn Pro Ser Leu Lys Ser
1               5                   10                  15

<210> SEQ ID NO 18
<211> LENGTH: 18

<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: heavy chain variable region CDR3

<400> SEQUENCE: 18

Ala Arg Glu Asn Ser Gly Val Val Pro Ala Ala Gly Pro Asn Trp Phe
1 5 10 15

Asp Pro

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: heavy chain variable region CDR3

<400> SEQUENCE: 19

Ala Arg Glu Asn Ser Gly Val Val Pro Ala Ala Gly Pro Asn Trp Phe
1 5 10 15

Gly Pro

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: heavy chain variable region CDR1
<220> FEATURE:
<221> NAME/KEY: MOD_RES
<222> LOCATION: (3)..(3)
<223> OTHER INFORMATION: Xaa is selected from V and I
<220> FEATURE:
<221> NAME/KEY: MOD_RES
<222> LOCATION: (4)..(4)
<223> OTHER INFORMATION: Xaa is selected from S, V, R, G or W
<220> FEATURE:
<221> NAME/KEY: MOD_RES
<222> LOCATION: (6)..(6)
<223> OTHER INFORMATION: Xaa is selected from S or A
<220> FEATURE:
<221> NAME/KEY: MOD_RES
<222> LOCATION: (7)..(7)
<223> OTHER INFORMATION: Xaa is selected from S or A
<220> FEATURE:
<221> NAME/KEY: MOD_RES
<222> LOCATION: (11)..(11)
<223> OTHER INFORMATION: Xaa is selected from G, A, S or T

<400> SEQUENCE: 20

Gly Ser Xaa Xaa Ser Xaa Xaa Tyr Tyr Trp Xaa
1 5 10

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: heavy chain variable region CDR2

<220> FEATURE:
<221> NAME/KEY: MOD_RES
<222> LOCATION: (2)..(2)
<223> OTHER INFORMATION: Xaa is selected from I or A
<220> FEATURE:
<221> NAME/KEY: MOD_RES
<222> LOCATION: (3)..(3)
<223> OTHER INFORMATION: Xaa is selected from Y or N
<220> FEATURE:
<221> NAME/KEY: MOD_RES
<222> LOCATION: (5)..(5)
<223> OTHER INFORMATION: Xaa is selected from S, K or R
<220> FEATURE:
<221> NAME/KEY: MOD_RES
<222> LOCATION: (13)..(13)
<223> OTHER INFORMATION: Xaa is selected from S or F

<400> SEQUENCE: 21

```
Ser Xaa Xaa Tyr Xaa Gly Ser Thr Tyr Tyr Asn Pro Xaa Leu Lys Ser
1               5                   10                  15
```

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: heavy chain variable region CDR3
<220> FEATURE:
<221> NAME/KEY: MOD_RES
<222> LOCATION: (4)..(4)
<223> OTHER INFORMATION: Xaa is selected from G or N
<220> FEATURE:
<221> NAME/KEY: MOD_RES
<222> LOCATION: (17)..(17)
<223> OTHER INFORMATION: Xaa is selected from D or G

<400> SEQUENCE: 22

```
Ala Arg Glu Xaa Ser Gly Val Val Pro Ala Ala Gly Pro Asn Trp Phe
1               5                   10                  15

Xaa Pro
```

<210> SEQ ID NO 23
<211> LENGTH: 126
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: ADI-02396: heavy chain variable region

<400> SEQUENCE: 23

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

-continued

```
Cys Ala Arg Glu Gly Ser Gly Val Val Pro Ala Ala Gly Pro Asn Trp
            100                 105                 110

Phe Asp Pro Trp Gly Gln Gly Thr Leu Val Thr Val Ser Ser
        115                 120                 125
```

<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: light chain variable region

<400> SEQUENCE: 24

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Asn Trp Phe Thr
                85                  90                  95

Phe Gly Gly Gly Thr Lys Val Glu Ile Lys
            100                 105
```

<210> SEQ ID NO 25
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: ADI-09111: heavy chain variable region

<400> SEQUENCE: 25

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser
        115                 120                 125
```

<210> SEQ ID NO 26

-continued

```
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-09112: heavy chain variable region

<400> SEQUENCE: 26

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Phe
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Gly Pro Trp Gly Gln Gly Thr Leu Val Thr Val Ser Ser
        115                 120                 125


<210> SEQ ID NO 27
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-09113: heavy chain variable region

<400> SEQUENCE: 27

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ala Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser
        115                 120                 125


<210> SEQ ID NO 28
<211> LENGTH: 126
<212> TYPE: PRT
<213> ORGANISM: Artificial Sequence
<220> FEATURE:
<223> OTHER INFORMATION: Description of Artificial Sequence: Synthetic
```

polypeptide
<220> FEATURE:
<223> OTHER INFORMATION: ADI-10085: heavy chain variable region

<400> SEQUENCE: 28

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Val Ser Ser
20 25 30

Ser Tyr Tyr Trp Ala Trp Ile Arg Gln Pro Pro Gly Lys Gly Leu Glu
35 40 45

Trp Ile Gly Ser Ile Asn Tyr Lys Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Glu Asn Ser Gly Val Val Pro Ala Ala Gly Pro Asn Trp
100 105 110

Phe Gly Pro Trp Gly Gln Gly Thr Leu Val Thr Val Ser Ser
115 120 125

<210> SEQ ID NO 29
<211> LENGTH: 126
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: ADI-10086: heavy chain variable region

<400> SEQUENCE: 29

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Arg Ser Ser
20 25 30

Ala Tyr Tyr Trp Gly Trp Ile Arg Gln Pro Pro Gly Lys Gly Leu Glu
35 40 45

Trp Ile Gly Ser Ile Asn Tyr Arg Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Glu Asn Ser Gly Val Val Pro Ala Ala Gly Pro Asn Trp
100 105 110

Phe Gly Pro Trp Gly Gln Gly Thr Leu Val Thr Val Ser Ser
115 120 125

<210> SEQ ID NO 30
<211> LENGTH: 126
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: ADI-10087: heavy chain variable region

<400> SEQUENCE: 30

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ala
            20                  25                  30

Ser Tyr Tyr Trp Ser Trp Ile Arg Gln Pro Pro Gly Lys Gly Leu Glu
        35                  40                  45

Trp Ile Gly Ser Ile Asn Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Gly Pro Trp Gly Gln Gly Thr Leu Val Thr Val Ser Ser
        115                 120                 125


<210> SEQ ID NO 31
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10088: heavy chain variable region

<400> SEQUENCE: 31

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Ser Ser
            20                  25                  30

Ser Tyr Tyr Trp Ala Trp Ile Arg Gln Pro Pro Gly Lys Gly Leu Glu
        35                  40                  45

Trp Ile Gly Ser Ile Asn Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser
        115                 120                 125


<210> SEQ ID NO 32
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10089: heavy chain variable region

<400> SEQUENCE: 32

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Ser Ser
```

```
            20                  25                  30

Ser Tyr Tyr Trp Thr Trp Ile Arg Gln Pro Pro Gly Lys Gly Leu Glu
        35                  40                  45

Trp Ile Gly Ser Ile Asn Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser
        115                 120                 125


<210> SEQ ID NO 33
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10090: heavy chain variable region

<400> SEQUENCE: 33

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Trp Ser Ser
            20                  25                  30

Ser Tyr Tyr Trp Thr Trp Ile Arg Gln Pro Pro Gly Lys Gly Leu Glu
        35                  40                  45

Trp Ile Gly Ser Ile Asn Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser
        115                 120                 125


<210> SEQ ID NO 34
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-02396: heavy chain

<400> SEQUENCE: 34

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45
```

-continued

```
Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Gly Val Val Pro Ala Ala Gly Pro Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450
```

<210> SEQ ID NO 35
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: light chain

<400> SEQUENCE: 35

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Asn Trp Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 36
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: ADI-09111: heavy chain

<400> SEQUENCE: 36

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60
```

-continued

```
Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450
```

<210> SEQ ID NO 37
<211> LENGTH: 451
<212> TYPE: PRT

<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: ADI-09112: heavy chain

<400> SEQUENCE: 37

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Ser Tyr Tyr Trp Gly Trp Ile Arg Gln Pro Pro Gly Lys Gly Leu Glu
35 40 45

Trp Ile Gly Ser Ile Tyr Tyr Ser Gly Ser Thr Tyr Tyr Asn Pro Phe
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Glu Asn Ser Gly Val Val Pro Ala Ala Gly Pro Asn Trp
100 105 110

Phe Gly Pro Trp Gly Gln Gly Thr Leu Val Thr Val Ser Ser Ala Ser
115 120 125

Thr Lys Gly Pro Ser Val Phe Pro Leu Ala Pro Cys Ser Arg Ser Thr
130 135 140

Ser Glu Ser Thr Ala Ala Leu Gly Cys Leu Val Lys Asp Tyr Phe Pro
145 150 155 160

Glu Pro Val Thr Val Ser Trp Asn Ser Gly Ala Leu Thr Ser Gly Val
165 170 175

His Thr Phe Pro Ala Val Leu Gln Ser Ser Gly Leu Tyr Ser Leu Ser
180 185 190

Ser Val Val Thr Val Pro Ser Ser Asn Phe Gly Thr Gln Thr Tyr Thr
195 200 205

Cys Asn Val Asp His Lys Pro Ser Asn Thr Lys Val Asp Lys Thr Val
210 215 220

Glu Arg Lys Cys Cys Val Glu Cys Pro Pro Cys Pro Ala Pro Pro Val
225 230 235 240

Ala Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Gln Phe Asn Trp Tyr Val Asp Gly Val Glu
275 280 285

Val His Asn Ala Lys Thr Lys Pro Arg Glu Glu Gln Phe Asn Ser Thr
290 295 300

Phe Arg Val Val Ser Val Leu Thr Val Val His Gln Asp Trp Leu Asn
305 310 315 320

Gly Lys Glu Tyr Lys Cys Lys Val Ser Asn Lys Gly Leu Pro Ala Pro
325 330 335

Ile Glu Lys Thr Ile Ser Lys Thr Lys Gly Gln Pro Arg Glu Pro Gln
340 345 350

Val Tyr Thr Leu Pro Pro Ser Arg Glu Glu Met Thr Lys Asn Gln Val
355 360 365

Ser Leu Thr Cys Leu Val Lys Gly Phe Tyr Pro Ser Asp Ile Ala Val 370 375 380

Glu Trp Glu Ser Asn Gly Gln Pro Glu Asn Asn Tyr Lys Thr Thr Pro
385 390 395 400

Pro Met Leu Asp Ser Asp Gly Ser Phe Phe Leu Tyr Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro Gly
450

<210> SEQ ID NO 38
<211> LENGTH: 451
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: ADI-09113: heavy chain

<400> SEQUENCE: 38

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Val Ser Ser Ser
20 25 30

Ser Tyr Tyr Trp Gly Trp Ile Arg Gln Pro Pro Gly Lys Gly Leu Glu
35 40 45

Trp Ile Gly Ser Ala Tyr Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Glu Asn Ser Gly Val Val Pro Ala Ala Gly Pro Asn Trp
100 105 110

Phe Asp Pro Trp Gly Gln Gly Thr Leu Val Thr Val Ser Ser Ala Ser
115 120 125

Thr Lys Gly Pro Ser Val Phe Pro Leu Ala Pro Cys Ser Arg Ser Thr
130 135 140

Ser Glu Ser Thr Ala Ala Leu Gly Cys Leu Val Lys Asp Tyr Phe Pro
145 150 155 160

Glu Pro Val Thr Val Ser Trp Asn Ser Gly Ala Leu Thr Ser Gly Val
165 170 175

His Thr Phe Pro Ala Val Leu Gln Ser Ser Gly Leu Tyr Ser Leu Ser
180 185 190

Ser Val Val Thr Val Pro Ser Ser Asn Phe Gly Thr Gln Thr Tyr Thr
195 200 205

Cys Asn Val Asp His Lys Pro Ser Asn Thr Lys Val Asp Lys Thr Val
210 215 220

Glu Arg Lys Cys Cys Val Glu Cys Pro Pro Cys Pro Ala Pro Pro Val
225 230 235 240

Ala Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser

-continued

```
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450


<210> SEQ ID NO 39
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10085: heavy chain

<400> SEQUENCE: 39

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Val Ser Ser
            20                  25                  30

Ser Tyr Tyr Trp Ala Trp Ile Arg Gln Pro Pro Gly Lys Gly Leu Glu
        35                  40                  45

Trp Ile Gly Ser Ile Asn Tyr Lys Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Gly Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
```

-continued

```
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450


<210> SEQ ID NO 40
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10086: heavy chain

<400> SEQUENCE: 40

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ala Tyr Tyr Trp Gly Trp Ile Arg Gln Pro Pro Gly Lys Gly Leu Glu
```

-continued

```
        35                  40                  45

Trp Ile Gly Ser Ile Asn Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Gly Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450
```

<210> SEQ ID NO 41
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: ADI-10087: heavy chain

<400> SEQUENCE: 41

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ala
            20                  25                  30

Ser Tyr Tyr Trp Ser Trp Ile Arg Gln Pro Pro Gly Lys Gly Leu Glu
        35                  40                  45

Trp Ile Gly Ser Ile Asn Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Gly Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350
```

-continued

```
Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450


<210> SEQ ID NO 42
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10088: heavy chain

<400> SEQUENCE: 42

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Ser Ser
            20                  25                  30

Ser Tyr Tyr Trp Ala Trp Ile Arg Gln Pro Pro Gly Lys Gly Leu Glu
        35                  40                  45

Trp Ile Gly Ser Ile Asn Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240
```

Ala Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Gln Phe Asn Trp Tyr Val Asp Gly Val Glu
275 280 285

Val His Asn Ala Lys Thr Lys Pro Arg Glu Glu Gln Phe Asn Ser Thr
290 295 300

Phe Arg Val Val Ser Val Leu Thr Val Val His Gln Asp Trp Leu Asn
305 310 315 320

Gly Lys Glu Tyr Lys Cys Lys Val Ser Asn Lys Gly Leu Pro Ala Pro
325 330 335

Ile Glu Lys Thr Ile Ser Lys Thr Lys Gly Gln Pro Arg Glu Pro Gln
340 345 350

Val Tyr Thr Leu Pro Pro Ser Arg Glu Glu Met Thr Lys Asn Gln Val
355 360 365

Ser Leu Thr Cys Leu Val Lys Gly Phe Tyr Pro Ser Asp Ile Ala Val
370 375 380

Glu Trp Glu Ser Asn Gly Gln Pro Glu Asn Asn Tyr Lys Thr Thr Pro
385 390 395 400

Pro Met Leu Asp Ser Asp Gly Ser Phe Phe Leu Tyr Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro Gly
450

<210> SEQ ID NO 43
<211> LENGTH: 451
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: ADI-10089: heavy chain

<400> SEQUENCE: 43

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Gly Ser Ser
20 25 30

Ser Tyr Tyr Trp Thr Trp Ile Arg Gln Pro Pro Gly Lys Gly Leu Glu
35 40 45

Trp Ile Gly Ser Ile Asn Tyr Arg Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Glu Asn Ser Gly Val Val Pro Ala Ala Gly Pro Asn Trp
100 105 110

Phe Asp Pro Trp Gly Gln Gly Thr Leu Val Thr Val Ser Ser Ala Ser
115 120 125

```
Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450


<210> SEQ ID NO 44
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10090: heavy chain

<400> SEQUENCE: 44

Gln Leu Gln Leu Gln Glu Ser Gly Pro Gly Leu Val Lys Pro Ser Glu
1               5                   10                  15
```

-continued

```
Thr Leu Ser Leu Thr Cys Thr Val Ser Gly Gly Ser Ile Trp Ser Ser
            20                  25                  30

Ser Tyr Tyr Trp Thr Trp Ile Arg Gln Pro Pro Gly Lys Gly Leu Glu
        35                  40                  45

Trp Ile Gly Ser Ile Asn Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430
```

-continued

```
Met His Glu Ala Leu His Asn His Tyr Thr Gln Lys Ser Leu Ser Leu
        435                 440                 445

Ser Pro Gly
    450


<210> SEQ ID NO 45
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region FR1

<400> SEQUENCE: 45

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25


<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region FR2

<400> SEQUENCE: 46

Trp Ile Arg Gln Pro Pro Gly Lys Gly Leu Glu Trp Ile Gly
1               5                   10


<210> SEQ ID NO 47
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: heavy chain variable region FR3

<400> SEQUENCE: 47

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30


<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region FR4

<400> SEQUENCE: 48

Trp Gly Gln Gly Thr Leu Val Thr Val Ser Ser
1               5                   10


<210> SEQ ID NO 49
<211> LENGTH: 23
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain variable region FR1

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys
            20


<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain variable region FR2

<400> SEQUENCE: 50

Trp Tyr Gln Gln Lys Pro Gly Gln Ala Pro Arg Leu Leu Ile Tyr
1               5                   10                  15


<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: light chain variable region FR3

<400> SEQUENCE: 51

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30


<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain variable region FR4

<400> SEQUENCE: 52

Phe Gly Gly Gly Thr Lys Val Glu Ile Lys
1               5                   10


<210> SEQ ID NO 53
<211> LENGTH: 692
<212> TYPE: PRT
<213> ORGANISM: Homo sapiens
<220> FEATURE:
<223> OTHER INFORMATION: amino acid sequence of PCSK9 antigen

<400> SEQUENCE: 53

Met Gly Thr Val Ser Ser Arg Arg Ser Trp Trp Pro Leu Pro Leu Leu
1               5                   10                  15
```

-continued

```
Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430
```

-continued

```
Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690
```